(12) United States Patent
Scharf et al.

(10) Patent No.: US 9,441,256 B2
(45) Date of Patent: Sep. 13, 2016

(54) LIGNASES AND ALDO-KETO REDUCTASES FOR CONVERSION OF LIGNIN-CONTAINING MATERIALS TO FERMENTABLE PRODUCTS

(71) Applicant: PURDUE RESEARCH FOUNDATION, West Lafayette, IN (US)

(72) Inventors: Michael Scharf, Battle Ground, IN (US); Amit Sethi, Johnston, IA (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 14/379,990

(22) PCT Filed: Feb. 11, 2013

(86) PCT No.: PCT/US2013/025515
§ 371 (c)(1),
(2) Date: Aug. 20, 2014

(87) PCT Pub. No.: WO2013/126230
PCT Pub. Date: Aug. 29, 2013

(65) Prior Publication Data
US 2015/0184211 A1 Jul. 2, 2015

Related U.S. Application Data

(60) Provisional application No. 61/602,149, filed on Feb. 23, 2012.

(51) Int. Cl.
| | |
|---|---|
| *C12N 9/02* | (2006.01) |
| *C12N 9/04* | (2006.01) |
| *C12N 9/42* | (2006.01) |
| *C12P 19/14* | (2006.01) |
| *C12N 9/08* | (2006.01) |
| *C12N 9/24* | (2006.01) |

(52) U.S. Cl.
CPC ............. *C12P 19/14* (2013.01); *C12N 9/0006* (2013.01); *C12N 9/0008* (2013.01); *C12N 9/0061* (2013.01); *C12N 9/0065* (2013.01); *C12N 9/2437* (2013.01); *C12N 9/2445* (2013.01); *C12N 9/2482* (2013.01); *C12Y 111/01006* (2013.01); *Y02P 20/52* (2015.11)

(58) Field of Classification Search
CPC ..... C12N 9/2437; C12N 9/2408; C12P 1/00; C12P 19/34; C12Y 110/03002
USPC .................. 435/183, 195, 277, 99, 188, 348
See application file for complete search history.

(56) References Cited

U.S. PATENT DOCUMENTS

| | | |
|---|---|---|
| 2008/0118954 A1 | 5/2008 | Sticklen |
| 2011/0159544 A1 | 6/2011 | Puranen et al. |

FOREIGN PATENT DOCUMENTS

| | | |
|---|---|---|
| WO | 2010080408 A2 | 7/2010 |
| WO | 2010117843 A2 | 10/2010 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
NCBI, GeneBank accession No. ACX54558.1; (Oct. 21, 2010).
NCBI, GeneBank accession No. ADK12988.1; (Jul. 17, 2010).
Nakashima, K. et al., "Dual cellulose-digesting system of wood-feeding termite, *Coptotermes formosanus* Shiraki"; Insect Biochemistry and Molecular Biology; Jul. 2002, vol. 32, No. 7, pp. 777-784.
Benoit et al., Biotechnological applications and potential of fungal feruloyl esterases based on prevalence, classification and biochemical diversity (2008) Biotechnol. Letters 30: 387-396.
Breznak & Brune The Termite Gut Microflora as an Oxygen Sink: Microelectrode Determination of Oxygen and pH Gradients in Guts of Lower and Higher Termites (1995) Appl. Env. Microbiol. 61: 2681-2687.
Coy et al., Phenol-oxidizing laccases from the termite gut. (2010) Insect Biochem. Mol. Biol. 40: 723-732.

(Continued)

*Primary Examiner* — Md. Younus Meah
(74) *Attorney, Agent, or Firm* — David Hayzer

(57) ABSTRACT

Termites have specialized digestive systems that overcome the lignin barrier in wood to release fermentable simple sugars. Using the termite *Reticulitermes flavipes* and its gut symbionts, high-throughput titanium pyrosequencing and proteomics approaches experimentally compared the effects of lignin-containing diets on host-symbiont digestome composition. Proteomic investigations and functional digestive studies with recombinant lignocellulases conducted in parallel provided strong evidence of congruence at the transcription and translational levels and provide enzymatic strategies for overcoming recalcitrant lignin barriers in biofuel feedstocks. Briefly described, therefore, the disclosure provides a system for generating a fermentable product from a lignified plant material, the system comprising a cooperating series of at least two catalytically active polypeptides, where said catalytically active polypeptides are selected from the group consisting of: cellulase Cell-1, β-glu cellulase, an aldo-keto-reductase, a catalase, a laccase, and an endo-xylanase.

5 Claims, 46 Drawing Sheets

(56) References Cited

OTHER PUBLICATIONS

Crepin et al., Functional classification of the microbial feruloyl esterases (2004) Appl. Microbiol. Biotechnol. 63, 647-652.
Ford et al., Three aldo-keto reductases of the yeast Saccharomyces cerevisiae (2001) Chem Biol. Interact. 685:130-132.
Karlin & Altschul Applications and statistics for multiple high-scoring segments in molecular sequences (1993) Proc. Natl. Acad. Sci. USA 90: 5873-5877.
Kovaleva et al., Recombinant protein production in insect larvae: host choice, tissue distribution, and heterologous gene instability(2009) Biotech nol. Letts. 31: 38.
Kuhn et al., Purification and Partial Characterization of an Aldo-Keto Reductase from Saccharomyces cerevisiae (1995) Appli. Environ. Microbiol. 61: 1580.
Lange J.P., Lignocellulose conversion: an introduction to chemistry, process and economics (2007) Biofuels Bioprod. Bioref. 1: 39-48.
Zhou et al., Production and Characterization of a Recombinant Beta-1, 4-Endoglucanase (Glycohydrolase Family 9) from the termite Reticulitermes flavipes (2010) Arch. Insect Biochem. Physiol. 74: 147.
Ohkuma et al., Termite symbiotic systems: Efficient bio-recycling of lignocellulose (2006) Appl. Microbiol. Biotechnol. 61:1-9.
Reinhard et al, Hydroquinone: A General Phagostimulating Pheromone in Termites (2002) J. Chem. Ecol .28: 1.
Saha B.C., Hemicellulose Bioconversion (2003) J. Indust. Microbiol. Biotechnol. 30: 279-291.
Scharf & Tartar Termite digestomes as sources of novel lignocellulases (2008) Biofuels Bioprod. Birefin. 2: 540-552.
Scharf et al., Functional and translational analyses of a beta-glucosidase gene (glycosyl hydrolase family 1) isolated from the gut of the lower termite Reticulitermes flavipes (2010) Insect Biochem. Mol. Biol. 40: 611.
Scharf et al., Multiple Levels of Synergistic Collaboration in Termite Lignocellulose Digestion. PLoS One 6, e21709.
Suen et al., The Genome Sequence of the Leaf-Cutter Ant Atta cephalotes Reveals Insights into Its Obligate Symbiotic Lifestyle (2010) PLoS Genetics 7, e1002007.
Taprab et al., Symbiotic Fungi Produce Laccases Potentially Involved in Phenol Degradation in Fungus Combs of Fungus-Growing Termites in Thailand (2005) Appl. Env. Microbiol. 71: 7696-7704.
Tartar et al. Parallel metatranscriptome analyses of host and symbiont gene expression in the gut of the termite reticulitermes flavipes (2009) Biotech. Biofuels 2: 25.
Tarver et al., Socio-environmental and endocrine influences on developmental and caste-regulatory gene expression in the eusocial termite Reticulitermes flavipes (2010) BMC Mol. Biol. 11: 28.
Warnecke et al., Metagenomic and functional analysis of hindgut microbiota of a wood-feeding higher termite. (2007) Nature 450: 560-565.
Watanabe et al., A cellulase gene of termite origin (1998) Nature 394: 330-331.
Wheeler et al., Characterization of Four Esterase Genes and Esterase Activity from the Gut of the Termite Reticulitermes flavipes (2010) Arch. Insect Biochem. Physiol. 73: 30.
Zhou et al., Juvenile hormone and colony conditions differentially influence cytochrome P45D gene expression in the termite Reticulitermes flavipes (2006) Insect Mol, Biol. 15: 749.
Zhou et al., Correlation of cellulase gene expression and cellulolytic activity throughout the gut of the termite Reticulitermes jlavipes (2007) Gene 395: 29.

* cited by examiner

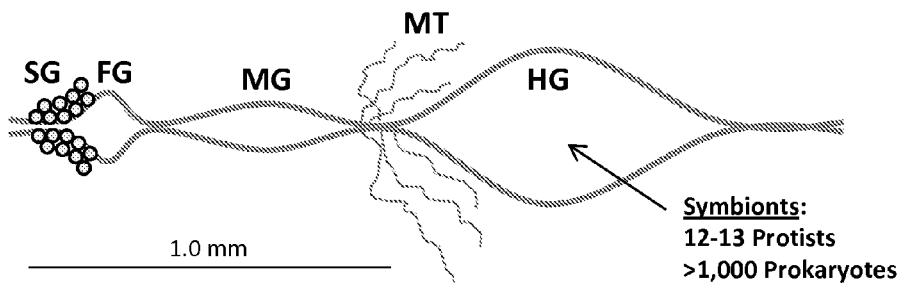
Fig. 1A
| | |
|---|---:|
| Total 454 Pyrosequence Reads | 346,798 |
| Total Bases | 98,960,499 |
| Culled Low-quality Reads | 21,669 |
| Average Quality Read Length | 285 |
| Number of Singletons | 97,254 |
| Number of Contigs | 9,552 |
| Number of Reads in Contigs | 227,875 |
| Average Contig Length | 837 |
| Contigs with E ≤ 0.001 vs. NR Database | 4,337 |
| Contigs with no NR Database Matches | 5,215 |
Fig. 1B
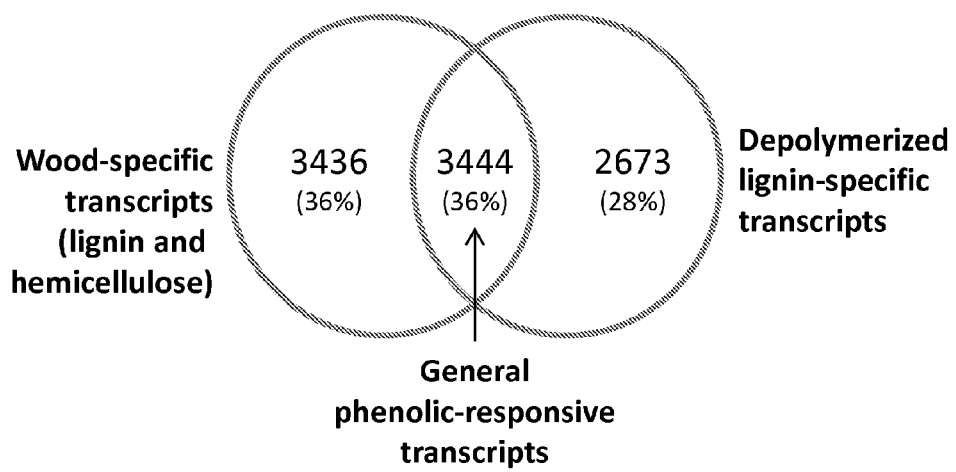
Fig. 1C

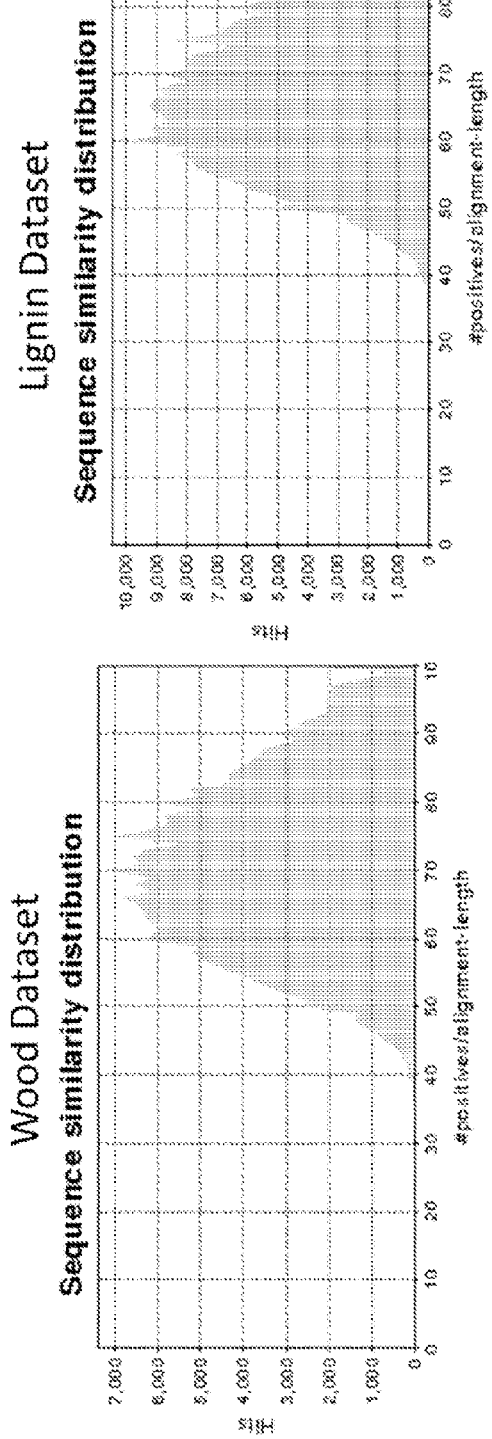
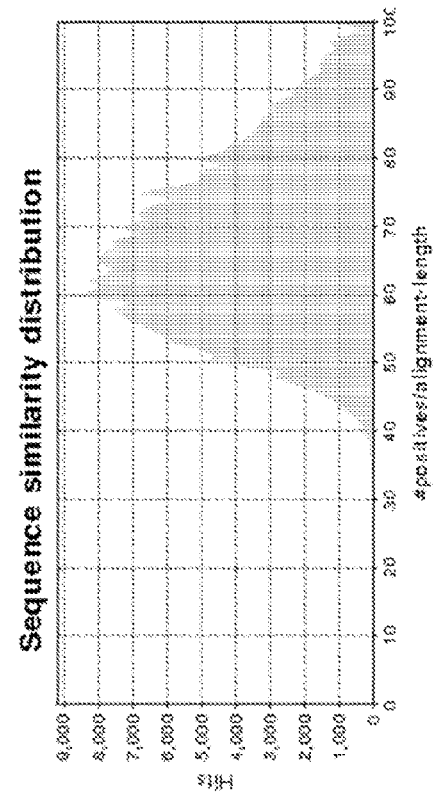
Fig. 5A
Fig. 5B
Fig. 5C

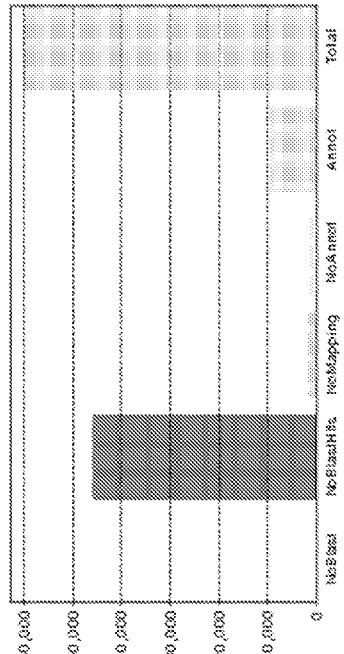
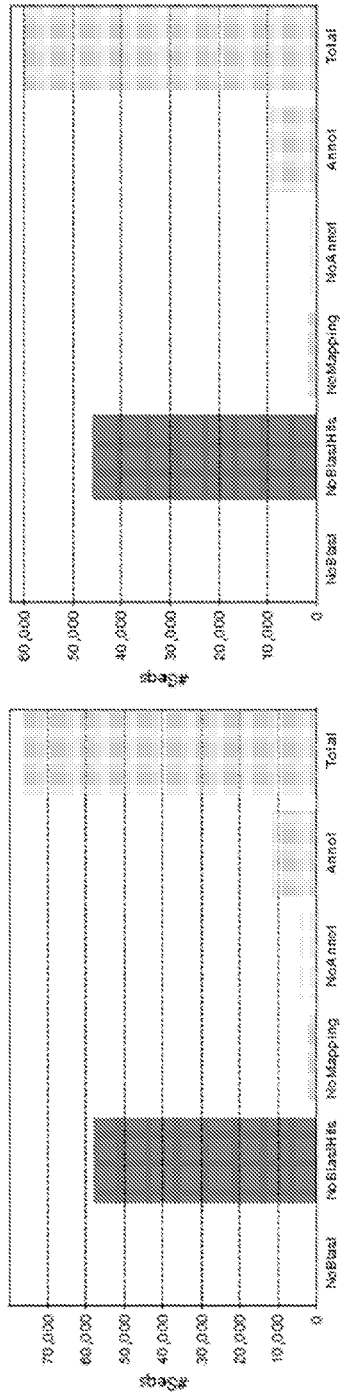
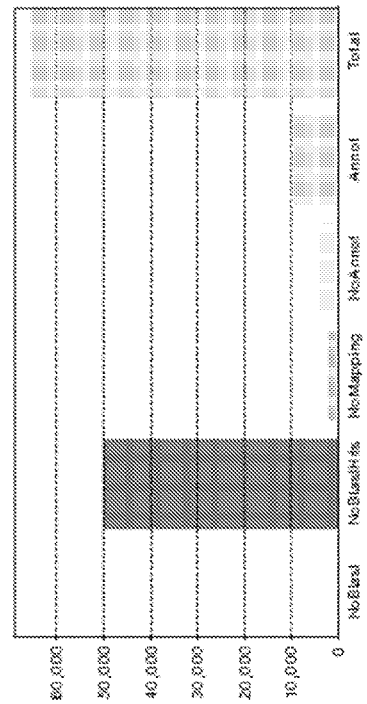

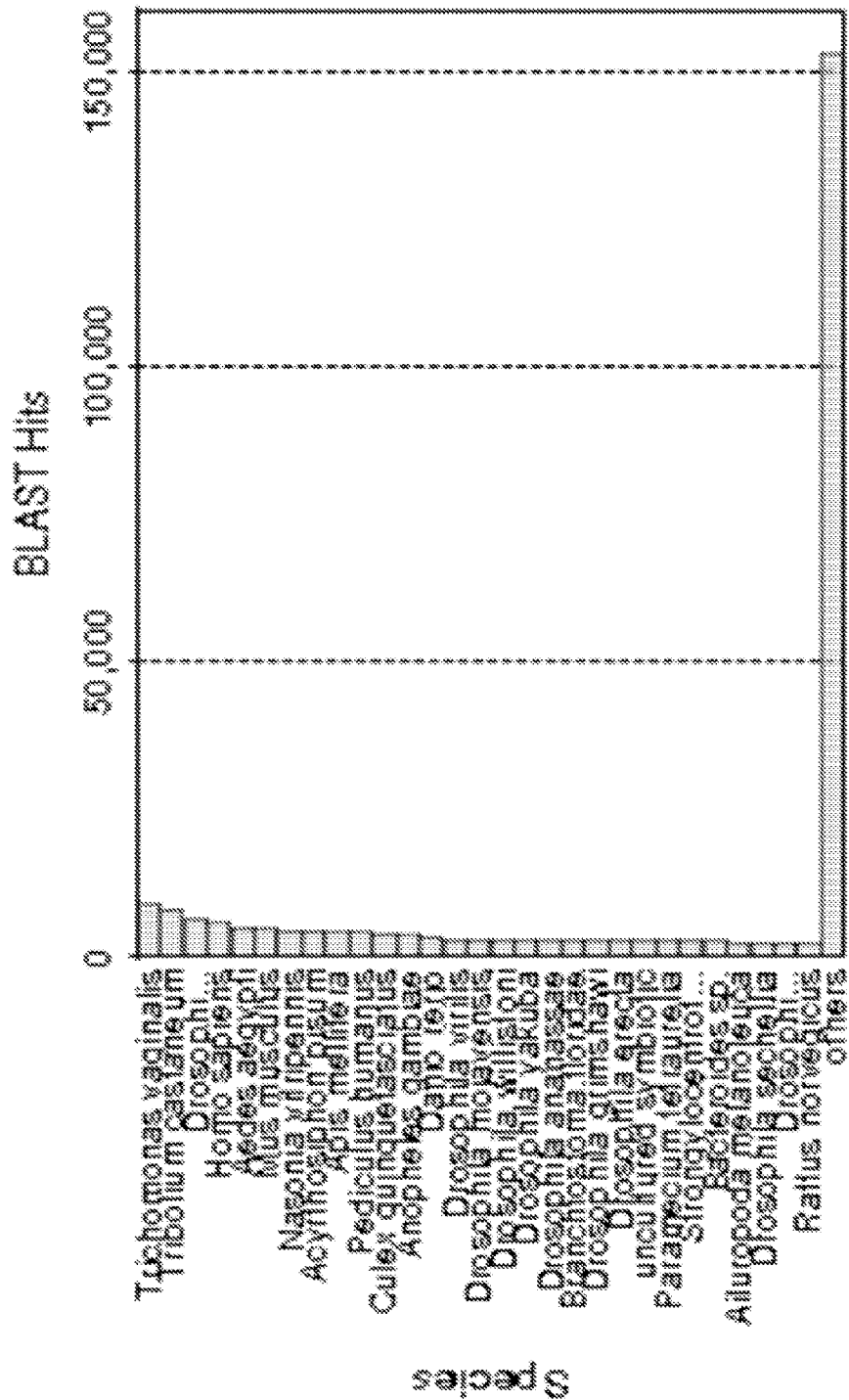

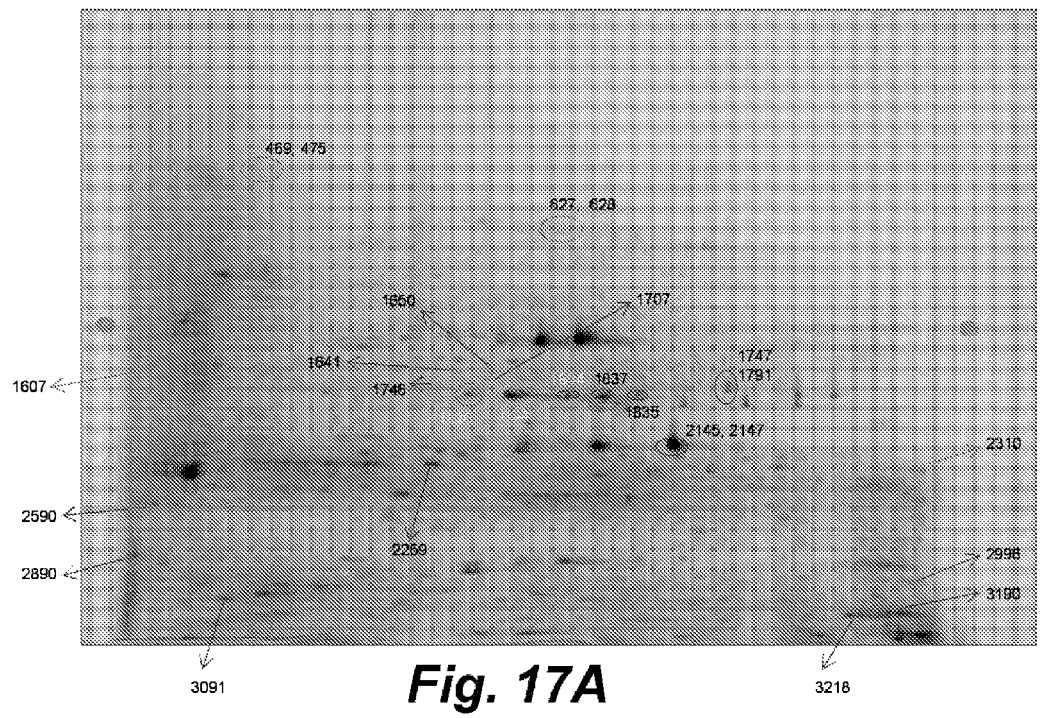

Fig. 17A

```
SEQ ID NO.: 1:  DAIDVGYR
SEQ ID NO.: 2:  DHKDYPFNIEF
SEQ ID NO.: 3:  DYPFNIEF
SEQ ID NO.: 4:  EDLFITSK
SEQ ID NO.: 5:  EGDDLFPEKDGK
SEQ ID NO.: 6:  HIDCAHVYGNEPEVGAAIK
SEQ ID NO.: 7:  KLIEFSK
SEQ ID NO.: 8:  LIEFSK
SEQ ID NO.: 9:  LVDQGLTK
SEQ ID NO.: 10: REDLFITSK
SEQ ID NO.: 11: SIGVSNFSSQQLER
SEQ ID NO.: 12: SKPGEVTQAVK
SEQ ID NO.: 13: SKPGEVTQAVKDAIDVGYR
SEQ ID NO.: 14: TLKSLTSSCLQR
SEQ ID NO.: 15: TLYSDVDYVDTWKELEK
SEQ ID NO.: 16: TPAQILLR
SEQ ID NO.: 17: VLANAR
SEQ ID NO.: 18: YEKTPAQILLR
SEQ ID NO.: 19: YQVQQGNITIPK
```

Fig. 17B

SEQ ID NO.: 20
CCAGTGAGGTGTTGGAGGTGAATGAGTGCAAGGTTAACGAATAGTGTTAGACGTTTACTGCCACAGTT
ATGGCGTTAAGCTAGAAAAAACTCCGACSGTCAAGTTCAACAACGGAATTGAATTTCCCATCTTTGGTCT
GGGAACATGGAAGTCCAAACCTGGTGAAGTCACTCAAGCTGTGAAGGATGCTATTGACGTTGGGTACCG
ACACATCGATTGCGCTCACGTGTATGGAAATGAACCTGAAGTTGGGGCCGCAATTAAGGCCAAGATCGG
CGAGAAAGTCGTGAAGCGTGAGGATCTGTTTATCACAAGCAAGCTGTGGAACACATTCCATCGACCAGA
CTTGGTTGCCCCTGCTATAAAGCAGACTTTGACTGACTTGGGTTTGGATTACTTGGACCTGTATTGATTC
ACTGGCCAATGCATACAAGGAAGGTGATGACCTCTTTCCGGAGAAGGATGGTAAAACTCTGTACAGTG
ATGTGGACTATGTTGACACATGTTCACAGACGAGTTGGATCAGGGCCTCACCAAGTCAATTG
GGGTGTCAAACTTAGTTCACAGCAGCTAGAACGAGTTCTGGCCAATGCTAGAATCAAGCCAGTTACGAA
CCAGGTTGAGTGTCACCCATATTTGAACCAAAAGAAGTTGATAGAGTTAGTAAAGCAAAAGGTGTAACA
ATCACTGCATACAGCCCGCTGGGCTCTCCAGATGCCCATGGGCCACGCCTGATGATCCTCAACTGTTGGA
AGATCCAAAGTGAAAGCTGTGGCTGCAAATATGAAAAGACTCCTGCCACAAAGTCACGTATTGTAGAGAACGCTCAAATCTT
GTGCAGCAAGGTAATATTACAATCCCCAAATCTGTGACAAGTCACGTATTGTAGAGAACGCTCAAATCTT
TGACTTCGAGCTGTCTGCAGAGGATGTTGCCACAATTGATTCTTTTGACTGCAATGACGTGTCTGTCACC
TGGGACTGGATTAAAGACCAAGGACTATCATTTAACATTGAATTCTAAGAAGTTGAAGCCACAAATGA
AGAATTTGCAAGAAAATGAAGTCACTGCCAGTCCATGGAGCGAGTTACGTAACGGGGATGGAGGTG
CCTTCACGATGACTCGTTCAGCATGCAGTCAGTAATCAGGAATACGCACTTGTATGCCAGTAACGTTGCAGTTTTG
ATGCTAGTCGTTCAGCATCCAAGTTGGTATCATCATCTTGATACATTTTTCGTAATTAGTTAAATTTTAAT
TACACTGGCTTGTGTCTGGGCCTGCTTAATTCCAGGCAGCCCAGAGTTTTGGCATTATATGCAACTTACA
AAAACAAATCATATGATGATTAGGGTCATTACTTGCGTAAAATATACAGTTGCATATTTCCAATTGCTA
CTACTGCAATAGGACAGGTTTATGTTGGGACAGAATTTAAGGTTATGTAAAATACTTCATGAATTACAGTG
ATGTATATTCATTTGTACATATTTGCCAGCTAGCAATGTTGTTTCTTCAGACACTGCCCTTCATTGTTACAATAT
ATTCATAAGTATTTCTCCCGTCATTACAATTGTTTTTCTTTGTAATAATGGTCGCATCAGTGATCTGATGAGA
CATGTTCTAGCTAAGCTGTGTGGCTTCAAACTAGGGCTTCACTGTACAGAAAATACTGAATAAAGTGACT
TCATGAAAAGT<u>AAAAAAAAAAAAAAAAAAAAAAAAAAAAAA</u>

```
SEQ ID NO.: 22
EcoRI
GAATTCATGGGTCACCACCATCATCACCATCATCACGGTTCTTCTCCGGATCCGATGGCGTCCGATCAGC
TCGTGAACTACAAGAAAAAGCAGACCGATAAGACTAAAATTGTAACCGGCCATGGTGCCCCGGTTGACAA
CCGTGGCGCTTCTCTCACCGTCGGTCCTCGTGGTCCTATGCTGCTCCAAGACATTACCTTCCTCGATGAA
CTGGCGCACTTTGATCGCGAGCGCATTCCAGAACGTGTTGTTCATGCAAAAGGTGCGGGTGCGTTCGGTT
ATTTCGAGGTTACTCATGATATTACGAAGTACTGCAAAGCATCCGTTTTCTCTAAGATTGGTAAGAAGAC
TCCAATCGCCGTTCGTTTTTCTACCGTAGGTGGCGAGTCTGGTAGCGCGGACACCGTCCGTGACCCGCGT
GGTTTCGCTGTTAAATTCTACACCGAAGACGGTATCTGGGACCTGGTCGGTAATAACACTCCGATCTTCT
TCATCCGTGATCCGCTGCTGTTCCCGGTTTTCATCCATACCCAGAAACGTAACCCGGCCACCCACCTGAA
AGACTGCGACATGTTCTGGGATTTCCTGTCTCTGCGCCCAGAATCTACCCACCAGGTTATGTTTCTCTTC
AGCGATCGTGGTATCCCGGACGGCTTCCGTCACATGAATGGTTACGGCTCTCATACGTTTAAGGCGATTA
ATGATAAGAATGAGGCCGTGTATGTGAAGTTCCACTATAAACCAACCAGGGTATCAAAAACCTCCTCGC
ACAGAAAGCGTCTGAAGTTGCGGTTGCAGATCCGGACTACTCTATCCGCCGACCTCTACAACGCTATGCA
CGTGGCCAGTACCCATCTTGGACCCTGTACATCCAAGTTATGACGTTTGAACAGGCGGAAAAATTCCGTT
GGAACCCGTTCGACCTGACGAAAGTTTGGCCGCATGCCGAATATCCTCTCGATTCCGGTAGGTAAACTGGT
TCTCGATCGCAACCCAGCGAATTACTTTGCTGAGGTAGAGCAGATTGCGTTCTCTCCGGCGCACATGGTT
CCGGGTATCGAACCGTCTCCTGATAAAATGCTGCAAGGCCGTCTCTTTTCTTACTCTGACATCCACCGTC
ACCGCCTCGGTGCGAACTATCTCCAGATCCCGGTGAATTGCCCGTACCGTACCCGTATCACCAACTACCA
ACGTGACGGCCCTCAGACCTTCACGAACAACCAAGAAGGCGCTCCGAACTACTACCCGAACTCTTTCTCT
GGTCCTGAAGATGTTCCGCACTGCGCTGCAATTAAGTTCGCGTCTACGGGTGACGTTGCGCGTTACAACT
CTGGCGACGAAGACAACTTCTCCCAGCCATCTCTGTTTTGGAAAAAGACCCTGAAACCGGAAGAGCGTGA
ACGCCTGGTACAAAACATCGTTGACCATGTAAAGATGCCGCGGACTTCGTCCAGGAGCGTACGGTTAAA
AACTTTTCTCAGGTTGACGCGGAGTTTGGTCGTAAGCTGACCGAAGGCCTGCGTAAACACTCTAAAAACA
GCTCTATCGCATCTGCCAACCTCGAGTAACTGCAG
                           PstI
```

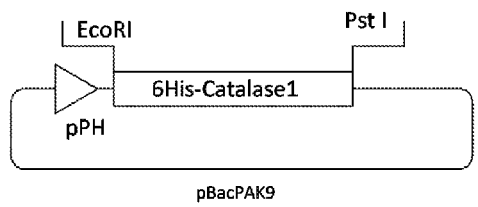

Fig. 23A

```
SEQ ID NO.: 23
MGHHHHHHHGSSPDPMASDQLVNYKKKQTDKTKIVTGHGAPVDNRGASLTVGPRGPMLLQDITFLDELA
HFDRERIPERVVHAKSAGAFGYFEVTHDITKYCKASVFSKIGKKTPIAVRFSTVGGESGSADTVRDPRGF
AVKFYTEDGIWDLVGNNTPIFFIRDPLLFPVFIHTQKRNPATHLKDCDMFWDFLSLRPESTHQVMFLFSD
RGIPDGFRHMNGYGSHTFKAINDKNEAVYVKFHYKTNQGIKNLLAQKASEVAVADPDYSIRDLYNAIARG
QYPSWTLYIQVMTFEEQAEKFRWNPFDLTKVWPHAEYPLIPVGKLVLDRNPANYFAEVEQIAFSPAHMVPG
IEPSPDKMLQGRLFSYSDTHRHRLGANYLQIPVNCPYRTRITNYQRDGPQTFTNNQEGAPNYYPNSFSGP
EDVPHCAAIKFASTGDVAKYNSGDEDNFSQPSLFWKKTLKPEEKERIVQNIVDHVKDAADFVQERTVKNF
SQVDAEFGRKLTEGLRKHSKNSSIASANLE-
```

Fig. 23B

Aldo-keto reductase (AKR) (SEQ ID NO.: 24)

Forward Primer 3
AGCCAGTGAGGTGTTGGAGGTGAAGTGAAGTGCAAGGTTAACGAAGTTAACGAATAGTGTTAGACGTTTTACTGCCACAGT
Forward Primer 4
TATGGCGTTAAGCTAGAGAAAAACTCCGACSGTCAAGTTCAACAACGGAATTGAATTCCCATCTTTGGT
CTGGGAACATGGAAGTCCAAACCTGTGAAGTCACTCAAGCTGTGAAGGATGCTATTGACGTTGGGTACC
GACACATCGATTGCGCTCACGTGTATGGAAATGAACCTGAAGTTGGGGCCGCAATTAAGGCCAAGATCGG
CGAGAAAGTCGTGAAGCGTGAGGATCGTGTTTATCACAAGCAAGCTGTGGAACACATTCCATCGACCAGAC
TTGGTTGCCCCTGCTATAAAGCAGACTTTGACTGGTTTGGATTACTTGGACCTGTATTTGATTC
ACTGCCAATGGCATACAAGGAAGGTGATGACCTCTCTTTCCGGAGAAGGATGGTAAAACTCTGTACAGTGA
TGTTGACTATGTTGACACATGGAAGGAGTTGGAGAAGTTGGTGGATCAAGCCCTCACCAAGTCAATTGGG
GTGTCAAACTTTAGTTCACAGACGTCTAGAACGAGTTCTGGCCAATGCTAGAATCAAGCCAGTTACGAACC
AGGTTGAGTGTCACCCATATTGAACCAAAAGAAGTTGATAGAGTTTAGTAAAGCAAAAGGTGTAACAAT
CACTGCCATACAGCCCGCTGGGCTCTCCAGATCGCCATGGGCCACGCTGATCCTCAACTGTTGAA
GATCCAAAAGTGAAAGCTGTGGCCTGCGCAAAATATGAAAAGACTCCTGCTCAGATCCTTCTGAGGTACCAGG
TGCAGCAAGGTAATATTACAATCCCCAAATCTGTGACAAAGTCACGTATTGTAGAGAACGCTCAAATCTT
TGACTTCGAGCTGTCTGCAGAGGATGTTGCCACAATTGATTCTTTTGACTGCAATGCAGACGTGTCTGTCAC
                                                    Reverse Primer 5
CTGGACTGGATTAAAGACCACCAAGGACTATCCATTTAACATTGAATTCTAAGAAGTTGAAGCCACAAATG
AAGAATTTGCAAGATGACTGCAGTACAGTTGAAGTCACTGCCATGGAGCGAGTTACGTAACGGGGATGGAGGTG
CCTTCACGATGACTGCAGTACAGTTGAAGTCACTGCCATGGAGCGAGTTACGTATGCCAGTAACGTTGCAGTTTT
GATGCTAGTCGTTCAGCATCCAAGTTGGTATCATCATCTTGATACATTTTTTCGTAATTAGGTTAAATT
TTAATTACACTGGCTTGTGTCTCGGGCCTGCTTAATTCCAGGCAGCCCCAGAGTTTTGGCATTATATGCAA
CTTACAAAACAAATCATATGATGATTAGGTCATTACTTGCGTAAAAAAATATTACAGTTGCATATTTTC
CAATTGCTACTACTGCCAATAGGACAGGTTTATGTTGGGACAGAATTTAAGGTTATGTAAATACTTCATG
AATTACAGTGATGTATATTCATTTTGTACATATTTGCCAGCTAGTGTTCTTTCAGACACTCTGCCCTTC
ATTTGTTACAATATATTCATAAGTATTTCCCCGTCATTACAATTGTTTTCTTTGTAATAATGGTGCA
TCAGTGATCTGATGAGACATGTTCTAGCTAAGCTGTGTGGCTTCAAACTAGGGCTTCACTGTACAGAAAA
TACTGAAATAAAGTGACTTCATGAAAAGTAAAAAAAAAAAAAAAAAAAAAAAAAAAA

Fig. 24A

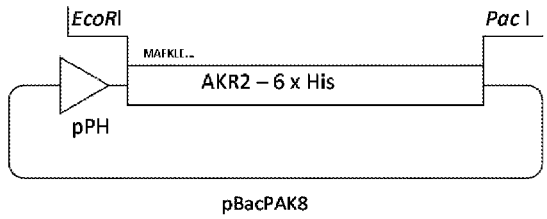

```
SEQ ID NO.: 27
BamHI
GGATCCTATGAGTGCAAGGTTAACGAATTCTGTTAGACGTTTTACTGCCACAGTTATGGCCTTCAAGCTG
GAAAAGACGCCTACCGTCAAGTTCAACAACGGTATCGAGTTTCCTATCTTGGTCTCGGTACGTGGAAGT
CTAAGCCTGGTGAGGTCACCCAAGCTGTCAAGGACGCTATCGACGTCGGTTACCGTCACATTGACTGTGC
TCATGTGTACGGTAATGAACCTGAAGTCGGCGCAGCTATCAAGGCTAAGATCGGTGAAAAGGTGGTGAAG
CGTGAGGACCTCTTCATCACGTCTAAGCTGTGGAATACCTTCCACCGTCCTGATCTGGTCGCTCCTGCTA
TTAAGCAGACGCTCACCGACCTCGGTCTGGATTACCTGGACCTGTACCTGATCCACTGGCCTATGGCTTA
CAAGGAAGGTGACGACCTGTTCCCTGAAAAGGATGGTAAGACCCTGTATTCTGATGTCGACTACGTCGAC
ACTTGGAAGGAACTGGAGAAGCTGGTGGACCAGGGTCTCACCAAGTCTATCGGTGTGTCTAACTTCTCT
TCTCAGCAGCTCGAACGTGTGCTGGCTAACGCCCGTATCAAGCCTGTCACGAACCAGGTCGAATGCCACCC
ATATCTGAACCAAAAGAAGCTGATCGAATTTTCCAAGGCTAAGGGTGTAACGATCACCGCTTACTCTCCT
CTGGGCTCCCCTGACCGTCCATGGGCTACCCCTGATGACCCTCAACTGCTCGAAGACCCTAAGGTCAAGG
CCGTGGCAGCTAAGTACGAAAAGACTCCTGCTCAAATCCTGCTGCGTTACCAAGTCCAGCAAGGTAACAT
CACTATCCCTAAGTCTGTGACTAAGTCTCGTATCGTCGAAAACGCTCAGATTTTCGATTTCGAACTGTCT
GCTGAAGACGTGGCTACCATCGACTCTTTCGACTGCAATGGTCGTGTCTGCCATCTGGACTGGATCAAGG
ACCACAAGGACTATCCTTTCAACATTGAGTTCGGCCGTGGTTCTCATCACCACCATCATCATCATTAATT
AA
PacI
```

Fig. 24B

```
Full length peptide (SEQ ID NO.: 28)
MSARLTNSVRRFTATVMAFKLEKTPTVKFNNGIEFPIFGLGTWKSKPGEVTQAVKDAIDVGYRHIDCAHV
YGNEPEVGAAIKAKIGEKVVKREDLFITSKLWNTFHRPDLVAPAIKQTLTDLGLDYLDLYLIHWPMAYKE
GDDLFPEKDGKTLYSDVDYVDTWKELEKLVDQGLTKSIGVSNFSSQQLERVLANARIKPVTNQVECHPYL
NQKKLIEFSKAKGVTITAYSPLGSPDRPWATPDDPQLLEDPKVKAVAAKYEKTPAQILLRYQVQQGNITI
PKSVTKSRIVENAQIFDFELSAEDVATIDSFDCNGRVCHLDWIKDHKDYPFNIEF*

Truncated peptide: (SEQ ID NO.: 29)
MAFKLEKTPTVKFNNGIEFPIFGLGTWKSKPGEVTQAVKDAIDVGYRHIDCAHVYGNEPEVGAAIKAKIG
EKVVKREDLFITSKLWNTFHRPDLVAPAIKQTLTDLGLDYLDLYLIHWPMAYKGDDLFPEKDGKTLYSD
VDYVDTWKELEKLVDQGLTKSIGVSNFSSQQLERVLANARIKPVTNQVECHPYLNQKKLIEFSKAKGVTI
TAYSPLGSPDRPWATPDDPQLLEDPKVKAVAAKYEKTPAQILLRYQVQQGNITIPKSVTKSRIVENAQIF
DFELSAEDVATIDSFDCNGRVCHLDWIKDHKDYPFNIEF*
```

Fig. 24C

Catalase (CAT) (SEQ ID NO.: 30)
GGCAGTAGTTGGTGTGCGTTTGTGTGAGCAGTTGGTGGACGTGTGATATTCGTTGAAAATGTCTTCTCC
GGATCCAGCTTCCGATCAGTTAGTAATTACAAGAAGAACAAACGATAAACGAAGATTGTTACTGGA
CATGGAGCACCAGTTGATAACCGTGGGGCCAGTTAACTGTGGGGCCCCATGCTGTTACAAG
ATATTACGTTTCTARATGAACTCGCACACTTTGACAGAGAACGTATCCAGAGAGAGTGGTCCATGCCAA
AGGGGCAGGTGCATTTGGCTACTTTGAAGTGRCACATGAGCATCACAAAATATTGTAAGGCGAGTGTTTC
TCAAAAATTGGCAAGAAGACGCCGATTGCTGTAAGGTTTTCTACAGTAGGTGGTGAGAGTGGGTCAGCTG
ACACAGTCAGAGATCCTCGGGGCTTTGCTGTGAAATTTTACACTGAAGATGGCATCTGGGACCTGTGGG
TAACAACACACCAATCTTCTTTATCAGGGACCCATTGCTGTTCCTCTCGTATTTATCCACACACAGAAGAGA
AATCCTGCAACACATCTGAAGGATTGTGACATGTTCTGGGACTTCCTCTCTCGAATCCACAC
ATCAAGTCATGTTTTCTGTTTTCTGACAGAGGCATTCCAGATGATTTCGTCATATGAATGTTATGGCTC
TCATACATTCAAGGCTATAAATGATAAGAACGAGGCTGTATACGTGAAATTCCATTATAAGACAAATCAG
GGCATCAAAAACTTACTGCCACAGAAAGCCTCAGAAGTAGCTGACCCTGATTACTCTATCCGAG
ACTTGTACAAATGCTATCGCACGAGGCCAGTACCCATCATGAGACTTTGTACATCCAAGTGATGACTTTGA
ACAAGCAGAGAAATTCAGGTGGAACCCCCTTTGACCTCACTAAGGTTTTGGCCGCATGCTGAGGTGGACAGATTGCAT
ATCCCCGTGGGCAAACTTGTGCTTGCCTGGCATTGAACCAAGTCCTGACAAGATGTTGCAGGGTCGGCTGTTCAG
CTACTTCAGACACGCACCGTCACCGACTGGGAGCCAACCGCAGACGTTTACCAACAACAGGAGGGAGCACCAAACT
ACGCGTATAACCAACTACCACCGTCACCGACTGGGAGCCAACCGCAGACGTTTACCAACAACAGGAGGGAGCACCAAACT
ACTACCCAAAACAGCTTTAGTGGGCCCGAAGATGGAGGATAACTTTAGCAGCAGACCCTCTCTTTTCTGAAGAAGACC
AGATGTAGCCAGGTACAACTCTGGAGATGAAGAATTCAGCAGCATTGTTCAGCCAGTGGATGCTCTGCTGACTTTG
CTCAAACCGGAGGAGCGAGAACGTCTGGTGCAGAACATTGTGGATCACGTGAAGGATGCTGCTGACTTTG
TACAGGAACGCACAGTGCCAGGTACAACTCTGTGCCAGCAGTTGGTCGCAAATGACTGAGGGACT
GCGTAAGCATTCCAAGAACAGCAGCATTGCTTCAGCACCTTCAAGACTTAACATTTCATGGGTGTTAACAGGTG
GGTTTTTGTGGGGCAAATTATTGATTTTGAAGACTCCAGGGGCCATYTTATTCTGTAACTTCAGTTAATATGCT
CTTAATGTGTTTGGTACTTTATGTACTCAGGAGGGTAACTTGTGTATGTTGAAAACATAAGGGGGGAAAATAAA
GTTACACACATCAATCAATTGTTGKGTAGAGAGAATAAAAAAAAAAAAAAAAAAAAAAAAA
CATTTTAGTAAAaaaaaaAAAAAAAAAAAAGAAAAAAAAAAAAAAAAAAA

*Fig. 25*

GHF7-3 cellulase (SEQ ID NO.: 31)
TTTTCATTTTCTGAATCATGCTGACTTTTGTGGTTGTGTTGCTTTCATTGGTTGTGTCTCTTGAGATTGG
GACTCAACAAACGGAGACTCATCCTAAATTGACGTGGCAGAATGGATCAAGTTCAGTGTCAGGGTCTATT
GTTCTTGATTCGAATTGGAGATGGGTTCATGACAGCGGGACGACTAATTGTTATGATGGGAATCTGTGGA
GCAGTGATCTTTGTCCAAGTTCAGATACATGCACACAGAAATGTTATATTGAGGGAGCAGATTATTCGGG
AACTTACGGAATTACGACGAGTGGTTCAAAGTTGACGCTGAAATTTGTTACGAAAGGATCGTATTCAACA
AACATCGGAAGTCGTGTTTACTTGTTGAAAGATGACAACACTTATGAAACATTCAAATTGAAGAATAAGG
AATTTACATTTACGGTGGATGATTCTCAACTTGATTGCGGACTGAATGGGGCATTGTATTTTGTTGCGAT
GGATGCAGATGGTGGAAAAGCAAAATATTCAGCTTTCAAGCCAGGGGCTAAATATGGAATGGGATATTGT
GATGCACAGTGCCCACATGACATGAAGTTTATCAGTGGAAAGGCTAATGTTGATGACTGGAAACCACAAG
ACAATGATGAAAATTCAGGAAATGGGAAACTTGGAACATGCTGTTCGGAAATGGATATTTGGGAGGGAAA
TGCAAAGTCACAGGCATATACAGTGCACGCTTGCACGAAAAGTGGACAATATGAATGTACGGGAACTGCT
TGCGGAGACTCAGATAACAGGTATGGGGGAACTTGCGACAAAGATGGATGCGACTATGCTTCATATAGAT
GGGGAGACCACTCGTTCTATGGTGAGGGTAAGACTGTGGACACGAAACAGCCAGTTACAGTTGTCACTCA
GTTTATCGGAGATCCGTTGACAGAAATCAGACGGGTTTATGTTCAAGGTGGGAAAGTGATTGAGAACTCG
AAAACATCGAACTTGGCTTCAACATATGATTCGATCACCGATGCATTNTGCGACGCGACGAAAGCAGCGA
GTGGCGATACTAACGATTTTAAGGCGAAAGGAGGCATGGCGGGATTCAGTAAGAATCTGGACNCTCCNCA
AGTATTGGTTTTGTCATTGTGGGATGATCACNCAGCGAATATGTTGTGGCTTGATTCGACGTATCCAACT
GATTCCAGTGATCCAACAGCAGCACGTGGACCTTGTCGACATCATCAGGTGTTCCAAAAGACGTTGAAA
GCGCGCAAGCCAATGCTCAAGTTGTATTTTCGGACATTAAGTTTGGGGCCATCAACTCGACTTATAAAGC
CAATTAAAAACCCTTTTTGAGAGCTCAATTTGGGTAAGATTTTTCTTTTTATTTGAGAGTCATTCATTG
TGTTTTTTTAAAAAGTGGTGTTTAATTATTTTTTTTTTTTGGAAGAATTGTTTATTTGGAATTGATTA
A

*Fig. 26*

GHF11-1 hemicellulase synthetic sequence codon-optimized for the host
*Trichoplusia ni* (SEQ ID NO.: 32)
PstI
ctgcagATGAAATTAATCTCTGTTTTGTTTGCGGCTTGCTGTAGCGAAATCGTTCGAAgaTgTtGTTAATA
CTACTGCGACGTCGAATGCATGTACCGTGACATCAAATCAACAGGGTACGTGTGATGGCGTTGCGTATGA
ATTGTGGATGTCAGGATCTGGCGGAAGCTGCACAATCAAAGGTGGTGGTAGTGCTGCATTAGCGCGAAA
TGGAGCAACAGTGGCGATTTCTTGTGTCGTGCTGGTCTTGGATCAGGCAGTGCAAGTGGCATCAAAGCTA
GCTTTGCATACACAAAATCAGGCAGTGGTGGTGGCTATTCGTTTATTGGGATCTATGGCTGGACCACCAA
CCCTCTGGTTGAATACTACATTGTGGATGATTGGTTCTCAGGAGGTGGTAACTCTGGCGGATCTCAGAAA
GGTTCTTCACCCAAGATGGTGCGACATATAACATCTGGCAACACACTCAGAACAACCAGCCATCGATCC
AGGGAACAGCGACATTTGAGCAATTCTTCAGCATCCGCTCAAGCCAGCGCACATCCGGTGATATCAATAT
CTCAGCTCACTTTGACAAATGGAGCAGCCTTGGATGAGAATGGGCAGCCTGTATGAGGCGAAATTGCTG
GTTGAGGCTGGTGGTGGTAGTGGAAACATTGACTATTCGTCTGGCAGCGTGACCAGG
ggtacc
KpnI

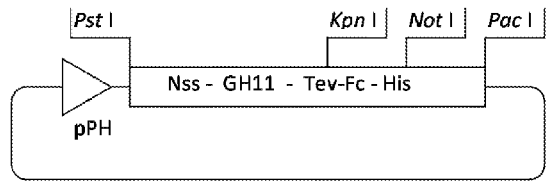

*Fig. 27A*

Recombinant protein sequence (excluding C-terminal tag) (SEQ ID NO.: 33)
MKLISVLFALAVAKSFEDLVNTTATSNACTVTSNQQGTCDGVAYELWMSGSGGSCTIKGGGSAAFSAKWS
NSGDFLCRAGLGSGSASGIKASFAYTKSGSGGGYSFIGIYGWTTNPLVEYYIVDDWFSGGGNSGGSQKGS
FTQDGATYNIWQHTQNNQPSIQGTATFEQFFSIRSSQRTSGDINISAHFDKWSSLGMRMGSLYEAKLLVE
AGGGSGNIDYSSGSVTRGT Mature protein sequence of GHF11 (SEQ ID NO.: 34)
FEDLVNTTATSNACTVTSNQQGTCDGVAYELWMSGSGGSCTIKGGGSAAFSAKWSNSGDFLCRAGLGSGS
ASGIKASFAYTKSGSGGGYSFIGIYGWTTNPLVEYYIVDDWFSGGGNSGGSQKGSFTQDGATYNIWQHTQ
NNQPSIQGTATFEQFFSIRSSQRTSGDINISAHFDKWSSLGMRMGSLYEAKLLVEAGGGSGNIDYSSGSV
TRGT

*Fig. 27B*

LacA laccase (expressed without signal peptide) (SEQ ID NO.: 35)
                                                        Forward Primer 1
ATACGGCCCTATCAGTTTACAGATCGGACGCCTACATTATGTTGCCTTGCGTCCTGCTTGCTTGCGCAAT
TGGTGTGGCTTCTGCAACATCAGTGCTCCTGAATTCATACCTTCAGCCCAACGATGACATTGATCGAAAC
ACGTACCTCCTAAATGCAAAAAGCAACAACTGTGCCCGTATATGCAATGGGACAGAGGCGCCCAAAATCT
GCTACTACCAATGGACAATTGAGAACTACGTGACTCTGTCAGAAGCGTGTGACAATTGTCCCTTGAATGT
GACGGCCTGTTACAACGCACAGTGCATCACAGCTGATGGATATGAGCGCAGTATCCTTTCGGTAAACAGG
AAACTACCGGGGCCTTCCATCGAGGTGTGCCTCAGAGACAGAGTAATTGTGGATATAACCAACAACATGG
CAGGGAGGACTACTAGCATCCACTGGCATGGGGTATTTCAGAAAGGGTCCCAGTACATGGACGGAGTTCC
CATGGTAACCCAGTGCACTATACATGAGGGTGACACATTCCGGTACGACTTTATCGCTAACAACGAGGGA
ACTCATTTCTGGCATTCCCATGACGGTTTGCAGAAGCTCGATGGCGTGACAGGTAACTTGGTGGTTAGGG
TGCCTAAAAATTTCGACCCGAACGGACAACTGTACGATTTCGATCTACCAGAACACAAAATTTTCATCAG
CGACTGGCTACATCTTTCCGCAGATGACCACTTTCCCGGACTCCGAGCGACAAATCCAGGACAAGATGCT
AACTCCTTTCTCATTAACGGCAGAGGACGTACCTTGATTGGAACTCAGTCCACCAACACACCGTATGCGC
AGATAAATGTGCAGTGGGCAGGAGGTACCGGCTTCGCATTGTGGGCTCCCTGTGCACTGTGTGCCCCAC
ACAGCTCACCATTGACGGGCACAAAATTACAGTCATAGCCACTGACGGCAATTCTGTGGCTCCTGCCAGA
GTCGACTCCCTCATCATTTACTCTGGTGAAAGATACGACGTCGTGTTAGAAGCCACTAATACGGAAGGAT
CTTACTGGATCCATCTAAAAGGCCTCGCCACTTGTGTTGGAAGTAGAGTTTACCAGCTGGGGGTGTTGCA
AATATGAAAATACAACAACCAATAAACTGCATGCTCTGACACCTGATCCAGGTTACGACGGATTCCCGCAA
CCAGCAAGCTACCGGGTCCTGAACCCAGAGAACGCAAGCTGTAGCATCGGCTCGACAGGCCTATGCGTCA
CGCAACTCGCGAACTCGGACCCCGTGCCACGGGACATCCTAACCCAGCTCCCGGACATCAACTATCTTCT
CCAATTTGGATTTGAAACTTTCGACTCCAGAAGTTTCTTCAAAGCTTACGACAGATATTTTGTCAGCCCC
TTTCTCGAGTTACTCAGCAGTACCGTCAACAACATTTCTTTCGTTTCGCCCCCATCTCCGCTCCTCTCAC
AAAGGGGGGATGTACCAGACGACATCCTATGCCCGACGGGGCTGATGGCCTGCCCCAGTGTCCCGGAGG
AAACTCCTACTGCACATGTGTCCATGTCATCAAAATCAAACTGGGTGCTTTGGTGCAGATCATCCTGTCG
GACCAGTCACCCAAATCCGACCTGAACCATCCGTTCCATATACACGGACATGCGTTTTACGTCCTGGGCA
TGGGGCAATACGCTGCAGGACAGACGGCGCAGGACCTCCTTAACTCCTTGAAGAGTAACGTGAGTAGTGT
GTCCCCTGCGCCGGTTCTTAAAGATACCGTCGCAGTTCCATCTGGCGGCTACGCGATCATCAAGTTCAGA
CCAAAAAACCCTGGTTACTGGTTCCTTCACTGCCACTTCCTGTACCATGTAGCGACCGGGATGAGTGTTG
TGCTCCAGGTGGGAGAAACAAGTGACTATCCCCCTACACCAGACGGCTTCCCCAAGTGTGGAAGCTTC<u>AC</u>
    Reverse Primer 2
<u>ACCTCCCGTGAACACCAACTGA</u>AGT

*Fig. 28*

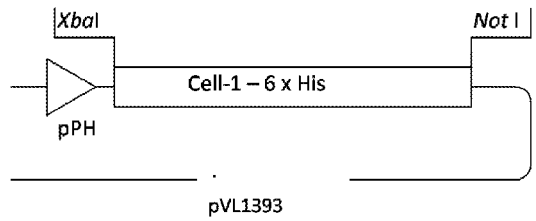

Cell-1 cellulase (expressed without signal peptide) (SEQ ID NO.: 38)
CCACTACCAGCCGCCATGAAGGTCTTCGTTTGTCTTCTGTCTGCACTGGCGCTTTGCCAAGCTGCTTACG
ACTATAAGACAGTACTAAGCAATTCGCTACTTTTCTACGAGGCTCAGCGATCGGGAAAATGCCGTCTGA
TCAGAAGGTCACGTGGAGGAAGGATTCCGCCCTTAACGACAAGGGCCAGAAGGGCGAGGACCTGACAGGA
GGATACTATGACGCTGGTGATTTTGTGAAGTTCGGCTTCCCTATGGCGTACACAGTCACCGTCCTCGCTT
GGGGTGTTATAGACTACGAATCAGCGTATTCTGCAGCAGGAGCTCTGGATAGTGGTCGCAAGGCTCTTAA
ATATGGCACGGACTACTTCCTCAAGGCGCACACGGCGGAACGAATTCTACGGACAAGTGGGCCAGGGA
GATGTCGACCACGCCTACTGGGGACGTCCAGAAGACATGACGATGTCCAGACCTGCCTACAAGATCGACA
CGTCGAAACCAGGGTCTGACCTGGCAGCCGAGACAGCCGCCGCCCTCGCTGCAACTGCCATCGCCTACAA
GAGTGCTGACGCAACTTATTCCAACAACTTGATCACCCACGCCAAGCAGCTTTTCGACTTCGCCAACAAT
TATCGCGGCAAATACAGTGATTCAATCACCGACGCGAAGAATTTCTACGCGTCCGGAGACTACAAGGACG
AGTTAGTATGGGCAGCCGCATGGCTCTACAGGGCGACCAACGACAACACCTATCTGACTAAAGCTGAATC
GCTATACAACGAATTCGGCCTCGGAAACTGGAACGGTGCCTTCAACTGGGATAACAAGATCTCCGGTGTA
CAGGTTCTACTGGCCAAGCTCACAAGCAAGCAGGCATACAAGGACAAGGTACAAGGCTACGTCGATTACT
TGATTTCGTCTCAGAAGAAGACACCCAAGGGTCTCGTATACATCGACCAGTGGGGTACCCTGCGACATGC
TGCCAATTCTGCTCTCATTGCTCTGCAGGCAGCCGACCTGGGTATCAATGCTGCTACTTATCGCGCGTAT
GCCAAGAAGCAGATCGATTACGCATTGGGTGATGGAGGTCGCAGCTACGTCGTAGGATTTGGTACTAACC
CACCCGTACGCCCTCACCACAGATCCAGCTCGTGCCCTGACGCACCAGCCGTATGTGACTGGAACACGTA
CAACAGCGCCGGCCCCAATGCCCACGTACTCACCGGAGCCTTGGTGGGTGGTCCAGATAGCAACGATAGC
TACACGGACGCTCGCAGCGATTACATCTCCAACGAAGTGGCCACAGATTACAACGCTGGCTTCCAATCAG
CTGTCGCTGGTCTCCTCAAGGCTGGCGTGTAACCGCACACAGCACTCAATGTCTCCCTGTCCACTGGACA
TGTGTACAATTTGACAACGAAAATGTAATATTCTTCAGAAAAGTGCAATAAAAGTTCACAATTCAACACA
AAAAAAAAAAAAAAAAAAAA

*Fig. 29A*

Recombinant protein sequence (SEQ ID NO.: 39)
MKILLAIALMLSTVMWVSTAAYDYKTVLSNSLLFYEAQRSGKLPSDQKVTWRKDSALNDKGQKGEDLTGG
YYDAGDFVKFGFPMAYTVTVLAWGVIDYESAYSAAGALDSGRKALKYGTDYFLKAHTAANEFYGQVGQGD
VDHAYWGRPEDMTMSRPAYKIDTSKPGSDLAAETAAALAATAIAYKSADATYSNNLITHAKQLFDFANNY
RGKYSDSITDAKNFYASGDYKDELVWAAAWLYRATNDNTYLTKAESLYNEFGLGNWNGAFNWDNKISGVQ
VLLAKLTSKQAYKDKVQGYVDYLISSQKKTPKGLVYIDQWGTLRHAANSALIALQAADLGINAATYRAYA
KKQIDYALGDGGRSYVVGFGTNPPVRPHHRSSSCPDAPAVCDWNTYNSAGPNAHVLTGALVGGPDSNDSY
TDARSDYISNEVATDYNAGFQSAVAGLLKAGVHHHHHH Mature protein sequence of GHF9 Cell-1 (SEQ ID NO.: 40)
AYDYKTVLSNSLLFYEAQRSGKLPSDQKVTWRKDSALNDKGQKGEDLTGGYYDAGDFVKFGFPMAYTVTV
LAWGVIDYESAYSAAGALDSGRKALKYGTDYFLKAHTAANEFYGQVGQGDVDHAYWGRPEDMTMSRPAYK
IDTSKPGSDLAAETAAALAATAIAYKSADATYSNNLITHAKQLFDFANNYRGKYSDSITDAKNFYASGDY
KDELVWAAAWLYRATNDNTYLTKAESLYNEFGLGNWNGAFNWDNKISGVQVLLAKLTSKQAYKDKVQGYV
DYLISSQKKTPKGLVYIDQWGTLRHAANSALIALQAADLGINAATYRAYAKKQIDYALGDGGRSYVVGFG
TNPPVRPHHRSSSCPDAPAVCDWNTYNSAGPNAHVLTGALVGGPDSNDSYTDARSDYISNEVATDYNAGF
QSAVAGLLKAGVHHHHHH

*Fig. 29B*

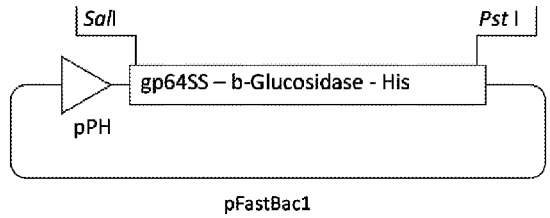

β-glu cellulase (expressed with intact signal peptide) (SEQ ID NO.: 41
GATTCTGACATCCTCACGTCTAGGGCGCTTGACAGAGCAACGAGATGAGGTTACAGACGGTTTGCTTCGT
CATCTTTGTGACGGCAGTATTCGGGGCTGACGTCGATAACGAAACCCTCTTCACGTTTCCTGAAGACTTT
AAGTTAGGCGCCGCTACGGCTTCATACCAGATTGAAGGAGGATGGAATGCGGATGGAAAGGGTGTCAATA
TTTGGGACACACTGACACATGAGCGCTCACAATTAGTGGTTGATAAATCAAGCGGTGACGTGGCTGACGA
CTCGTATCATCTTTATAAGGAGGACGTGAAGCTTCTGAAGAACATGGGGGCACAACTTTATCGCTTCTCT
ATATCTTGGGCTCGCATCCTGCCTGAAGGACATGATAATAAGGTGAACCAGGCGGGCATTGAGTACTACA
ACAAGCTCATAGACGAACTTCTAGACAATGGAATAGAGCCGATGGTTACTATGTATCACTGGGATCTACC
CCAGACACTCCAAGACCTGGGAGGATGGCCAAATAGAGAATTGGCAAAATACTCCGAGAATTACGCCCGC
GTTTTATTTCAAAACTTTGGAGACCGGGTTAAATTGTGGCTCACATTCAATGAGCCTCTGACTTTCATGG
ATGCATATGCATCTGAGACAGGAATGGCTCCATCAATTGACACACCCGGTATCGGCGATTACCTTGCGGC
ACACACTGTGATCCTTGCCCATGCCAATATCTACCGTATGTATGAGAGGGAATTCAAAGAGGAACAGAAA
GGAAAGGTTGGTATCGCACTCAACATACACTGGTGTGAGCCGGTGACTAATTCGACAAAGGACGTTGAGG
CTTGTGAAAGGTATCAACAGTTCAACCTGGGAATATACGCTCATCCCATCTTCTCTGTAGAGGGCGATTA
CCCCAGTGTTTTGAAAGCGAGGGTAGACGCAAACAGCGTAACGGAAGGTTACACCACATCTCGTCTACCT
AAATTCACTACAGAGGAAGTAGATTTCATCAGAGGAACACATGATTTCTTGGGTCTGAATTTCTACACTG
CTGTAACGGGAGCGGATGGAGTTGAAGGGGAACCCCCGTCGCGGTACAGAGACATGGGCGCGATCACATC
ACAGGATCCGGACTGGCCCGAGTCTGCTTCTTCATGGCTCAGAGTTGTACCATGGGGATTCCGCAAGGAA
CTTAACTGGATCGCGAACGAATACGGTAACCCTCCTATATACATCACTGAAAATGGCTTCTCCGACTACG
GTGGCCTCAATGATACAGACAGAGTGCTGTACTACACTGAACATTTAAAGGAGATGCTGAAGGCAATTCA
CATAGATGAAGTTAACGTAGTCGGATACACAGCCTGGAGCCTAGTAGACAATTTCGAATGGCTGCGAGGA
TATACTGAGAGGTTCGGTATACATGAAGTGAATTTCAACGACCCAAGTCGCCCACGAGTTCCCAAGGAGT
CAGCAAAGGTGCTCACAGAGATCTTCAACACAAGGAGGATTCCAGAACGCTTCCTAGACTAACTTCATAT
TCAAGACGCAAAGACTTATATCAAAAATTAATTAAAAGAGGGCTTACTGCTGACTGTAAGTTCCCTCAA
AACAGCAATAAGGTTTATGATCATGGAAAACACTTCGAATTAAATAAACTTATATACAAAAAAAAAAAAA
AAA

*Fig. 30A*

Recombinant protein sequence (SEQ ID NO.: 42)
MRLQTVCFVIFVTAVFGADVDNETLFTFPEDFKLGAATASYQIEGGWNADGKGVNIWDTLTHERSQLVVD
KSSGDVADDSYHLYKEDVKLLKNMGAQLYRFSISWARILPEGHDNKVNQAGIEYYNKLIDELLDNGIEPM
VTMYHWDLPQTLQDLGGWPNRELAKYSENYARVLFQNFGDRVKLWLTFNEPLTFMDAYASETGMAPSIDT
PGIGDYLAAHTVILAHANIYRMYEREFKEEQKGKVGIALNIHWCEPVTNSTKDVEACERYQQFNLGIYAH
PIFSVEGDYPSVLKARVDANSVTEGYTTSRLPKFTTEEVDFIRGTHDFLGLNFYTAVTGADGVEGEPPSR
YRDMGAITSQDPDWPESASSWLRVVPWGFRKELNWIANEYGNPPIYITENGFSDYGGLNDTDRVLYYTEH
LKEMLKAIHIDEVNVVGYTAWSLVDNFEWLRGYTERFGIHEVNFNDPSRPRVPKESAKVLTEIFNTRRIP
ERFLDHHHHHH Mature protein sequence of β-glu cellulase (SEQ ID NO.: 43)
ADVDNETLFTFPEDFKLGAATASYQIEGGWNADGKGVNIWDTLTHERSQLVVDKSSGDVADDSYHLYKED
VKLLKNMGAQLYRFSISWARILPEGHDNKVNQAGIEYYNKLIDELLDNGIEPMVTMYHWDLPQTLQDLGG
WPNRELAKYSENYARVLFQNFGDRVKLWLTFNEPLTFMDAYASETGMAPSIDTPGIGDYLAAHTVILAHA
NIYRMYEREFKEEQKGKVGIALNIHWCEPVTNSTKDVEACERYQQFNLGIYAHPIFSVEGDYPSVLKARV
DANSVTEGYTTSRLPKFTTEEVDFIRGTHDFLGLNFYTAVTGADGVEGEPPSRYRDMGAITSQDPDWPES
ASSWLRVVPWGFRKELNWIANEYGNPPIYITENGFSDYGGLNDTDRVLYYTEHLKEMLKAIHIDEVNVVG
YTAWSLVDNFEWLRGYTERFGIHEVNFNDPSRPRVPKESAKVLTEIFNTRRIPERFLDHHHHHH

*Fig. 30B*

GHF7-3 (SEQ ID NO.: 44)
                                                          Forward Primer
atgtttgctttgattgttttgccattcagctgctgcatgcacagggaaatcaggatttcacctacacga
ttaatggtactaaagttactgggcaaatagtgattgatcaagagtggagaggcaacaatacccaactgc
aactgtgaatctttctagttttggtgtaactgtgaatggagataacgtgtcacagagattcaagacagga
actgctgtggggtcccgtatctatattcttgctccaggggaaaagcgtatgagaagttcaagttggtga
actctgagctgacgtttgatgttgatattagccagattccatgcggaatgaatgctgccatttacactgc
cgaattgcctgcagacggtgtaacacctggtcacgaagctggagcagcgtatggtggcggatactgtgat
gcaaactatgttggaggagttggatgtgcagaatttgatattggtgaaagcaatgcacgtgcaacagttt
atacaagtcatggatgcagcccgacgactggctttgcaaaacagggcagcattagctgtgacacaggtgg
aactggagccaacccgtaccgtgtggacaagaacttctatggcaatggttcatcattcactgtcaatact
gcacagaaattcactgtggtgacgcaattcaaaggaaacccactgacttcgattgatcgtatctacatcc
aaggtaataaacaaacaaacagccgaacaacattaataacaacttggatcgtatcagcccatcgcttgc
ggcaggacatgttctgatattctcgatctgggcttcggatggagatatgtcttggatggactgcaatgac
aacggaccttgcaatgcaggccaggaaagttcacgttatttgggaacaaaactatccgatgctactgtta
                                  Reverse Primer
cctacagcaatgttaggtggggtccgattgatagcacttattagataaagaagttgaagaccgagagggt
cttttggtggaaaaaaaaatttttttttgtttattgaagtgaagcaatcttattttttttgtagtaatttt
ttttgtggataaaataaaaattgagataaagatgcaa Full length translation (SEQ ID NO.: 45)
MFALIVFAIQLLHAQGNQDFTYTINGTKVTGQIVIDQEWRGNNTPTATVNLSSFGVTVNGDNVSQRFKTG
TAVGSRIYILAPGGKAYEKFKLVNSELTFDVDISQIPCGMNAAIYTAELPADGVTPGHEAGAAYGGGYCD
ANYVGGVGCAEFDIGESNARATVYTSHGCSPTTGFAKQGSISCDTGGTGANPYRVDKNFYGNSSFTVNT
AQKFTVVTQFKGNPLTSIDRIYIQGNKQTKQPNNINNNLDRISPSLAAGHVLIFSIWASDGDMSWMDCND
NGPCNAGQESSRYLGTKLSDATVTYSNVRWGPIDSTY.

*Fig. 31*

Recombinant protein sequence: (SEQ ID NO.: 48)
MVSAIVLYVLLAAAAHSAFADLNQDFTYTINGTKVTGQIVIDQEWRGNNTPTATVNLSSFGVTVNGDNVS
QRFKTGTAVGSRIYILAPGGKAYEKFKLVNSELTFDVDISQIPCGMNAAIYTAELPADGVTPGHEAGAAY
GGGYCDANYVGGVGCAEFDIGESNARATVYTSHGCSPTTGFAKQGSISCDTGGTGANPYRVDKNFYGNGS
SFTVNTAQKFTVVTQFKGNPLTSIDRIYIQGNKQTKQPNNINNNLDRISPSLAAGHVLIFSIWASDGDMS
WMDCNDNGPCNAGQESSRYLGTKLSDATVTYSNVRWGPIDSTYGTLVPRGSHHHHHH

*Fig. 32*

Mature protein sequence of GHF7-3 (SEQ ID NO.: 50)
DLNQDFTYTINGTKVTGQIVIDQEWRGNNTPTATVNLSSFGVTVNGDNVSQRFKTGTAVGSRIYILAPGGKAYEKFKLV
NSELTFDVDISQIPCGMNAAIYTAELPADGVTPGHEAGAAYGGGYCDANYVGGVGCAEFDIGESNARATVYTSHGCSP
TTGFAKQGSISCDTGGTGANPYRVDKNFYGNGSSFTVNTAQKFTVVTQFKGNPLTSIDRIYIQGNKQTKQPNNINNNL
DRISPSLAAGHVLIFSIWASDGDMSWMDCNDNGPCNAGQESSRYLGTKLSDATVTYSNVRWGPIDSTYGTLVPRGSH
HHHHH

*Fig. 33*

Recombinant protein sequence Lac6 (SEQ ID NO.: 51)
MLPCVLLACAIGVASATSVLLNSYLQPNDDIDRNTYLLNAKSNNCARICNGTEAPKICYYQWTIENYVTL
SEACDNCPLNVTACYNAQCITADGYERSILSVNRKLPGPSIEVCLRDRVIVDITNNMAGRTTSIHWHGVF
QKGSQYMDGVPMVTQCTIHEGDTFRYDFIANNEGTHFWHSHDGLQKLDGVTGNLVVRVPKNFDPNGQLYD
FDLPEHKIFISDWLHLSADDHFPGLRATNPGQDANSFLINGRGRTLIGTQSTNTPYAQINVQWGRRYRLR
IVGSLCTVCPTQLTIDGHKITVIATDGNSVAPARVDSLIIYSGERYDVVLEATNTEGSYWIHLKGLATCV
GSRVYQLGVLQYENTTTNKLHALTPDPGYDGFPQPASYRVLNPENASCSIGSTGLCVTQLANSDPVPRDI
LTQLPDINYLLQFGFETFDSRSFFKAYDRYFVSPFLELLSSTVNNISFVSPPSPLLSQRGDVPDDILCPT
GADGLPQCPGGNSYCTCVHVIKIKLGALVQIILSDQSPKSDLNHPFHIHGHAFYVLGMGQYAAGQTAQDL
LNSLKSNVSSVSPAPVLKDTVAVPSGGYAIIKFRPKNPGYWFLHCHFLYHVATGMSVVLQVGETSDYPPT
PDGFPKCGSFTPPVNTNGGHHHHHH Mature protein sequence of Lac6 (SEQ ID NO.: 52)
TSVLLNSYLQPNDDIDRNTYLLNAKSNNCARICNGTEAPKICYYQWTIENYVTLSEACDNCPLNVTACYN
AQCITADGYERSILSVNRKLPGPSIEVCLRDRVIVDITNNMAGRTTSIHWHGVFQKGSQYMDGVPMVTQC
TIHEGDTFRYDFIANNEGTHFWHSHDGLQKLDGVTGNLVVRVPKNFDPNGQLYDFDLPEHKIFISDWLHL
SADDHFPGLRATNPGQDANSFLINGRGRTLIGTQSTNTPYAQINVQWGRRYRLRIVGSLCTVCPTQLTID
GHKITVIATDGNSVAPARVDSLIIYSGERYDVVLEATNTEGSYWIHLKGLATCVGSRVYQLGVLQYENTT
TNKLHALTPDPGYDGFPQPASYRVLNPENASCSIGSTGLCVTQLANSDPVPRDILTQLPDINYLLQFGFE
TFDSRSFFKAYDRYFVSPFLELLSSTVNNISFVSPPSPLLSQRGDVPDDILCPTGADGLPQCPGGNSYCT
CVHVIKIKLGALVQIILSDQSPKSDLNHPFHIHGHAFYVLGMGQYAAGQTAQDLLNSLKSNVSSVSPAPV
LKDTVAVPSGGYAIIKFRPKNPGYWFLHCHFLYHVATGMSVVLQVGETSDYPPTPDGFPKCGSFTPPVNT
NGGHHHHHH

*Fig. 34*

Recombinant protein sequence Lac12 (SEQ ID NO.: 53)

MLPCVLLACAIGVASATSVLLNSYLQPNDDIDRNTYLLNAKSNNCARICNGTEAPKICYYQWTIENYVTL
SEACDNCPLNVTACYNAQCITADGYERSILSVNRKLPGPSIEVCLRDRVIVDITNNMAGRTTSIHWHGVF
QKGSQYMDGVPMVTQCTIHEGDTLRYDFIANNEGTHFWHSHDGLQKLDGVTGNLVVRVPKNFDPNGQLYD
FDLPEHKIFISDWLHLSADDHFPGLRATNPGQDANSFLINGRGRTLIGTQSTNTPYAQINVQWGRRYRLR
IVGSLCTVCPTQLTIDGHKITVIATDGNSVAPARVDSLIIYSGERYDVVLEATNTEGSYWIHLKGLVTCV
GSRVYQLGVLQYENTTNKLHALTPDPGYDGFPQPASYRVLNPENASCSIGSTGLCVTQLANSDPVPRDI
LTQLPDINYLLQFGFKIFDSRSFFKAYDRYFVSPFLDLVSSTVNNISSVSPPSLLSQRGDVPDDVLCPT
GADGLPQCPGGNSYCTCVHVIKIKLGALVQIILSDQTPKSGLNHPFHLHGHAFYVLGMGQYAAGQTAQDL
LNSLKSNVSSVSPAPVLKDTIAVPSGGYAIIKFRPKNPGYWFLHCHFLYHVATGMSVVLQVGETSDYPPT
PDGFPKCGSFTPPVNTNGGHHHHHH

Mature protein sequence of Lac12 (SEQ ID NO.: 54)

TSVLLNSYLQPNDDIDRNTYLLNAKSNNCARICNGTEAPKICYYQWTIENYVTLSEACDNCPLNVTACYN
AQCITADGYERSILSVNRKLPGPSIEVCLRDRVIVDITNNMAGRTTSIHWHGVFQKGSQYMDGVPMVTQC
TIHEGDTLRYDFIANNEGTHFWHSHDGLQKLDGVTGNLVVRVPKNFDPNGQLYDFDLPEHKIFISDWLHL
SADDHFPGLRATNPGQDANSFLINGRGRTLIGTQSTNTPYAQINVQWGRRYRLRIVGSLCTVCPTQLTID
GHKITVIATDGNSVAPARVDSLIIYSGERYDVVLEATNTEGSYWIHLKGLVTCVGSRVYQLGVLQYENTT
NKLHALTPDPGYDGFPQPASYRVLNPENASCSIGSTGLCVTQLANSDPVPRDILTQLPDINYLLQFGFK
IFDSRSFFKAYDRYFVSPFLDLVSSTVNNISSVSPPSLLSQRGDVPDDVLCPTGADGLPQCPGGNSYCT
CVHVIKIKLGALVQIILSDQTPKSGLNHPFHLHGHAFYVLGMGQYAAGQTAQDLLNSLKSNVSSVSPAPV
LKDTIAVPSGGYAIIKFRPKNPGYWFLHCHFLYHVATGMSVVLQVGETSDYPPTDGFPKCGSFTPPVNT
NGGHHHHHH

*Fig. 35*

SEQUENCE LISTING

```
<160> NUMBER OF SEQ ID NOS: 63

<210> SEQ ID NO 1
<211> LENGTH: 8
<212> TYPE: PRT
<213> ORGANISM: Artificial sequence
<220> FEATURE:
<223> OTHER INFORMATION: Peptide 1

<400> SEQUENCE: 1

Asp Ala Ile Asp Val Gly Tyr Arg
1               5

<210> SEQ ID NO 2
<211> LENGTH: 11
<212> TYPE: PRT
<213> ORGANISM: Artificial sequence
<220> FEATURE:
<223> OTHER INFORMATION: Peptide 2

<400> SEQUENCE: 2

Asp His Lys Asp Tyr Pro Phe Asn Ile Glu Phe
1               5                   10

<210> SEQ ID NO 3
<211> LENGTH: 8
<212> TYPE: PRT
<213> ORGANISM: Artificial sequence
<220> FEATURE:
<223> OTHER INFORMATION: Peptide 3

<400> SEQUENCE: 3

Asp Tyr Pro Phe Asn Ile Glu Phe
1               5

<210> SEQ ID NO 4
<211> LENGTH: 8
<212> TYPE: PRT
<213> ORGANISM: Artificial sequence
<220> FEATURE:
```

```
<223> OTHER INFORMATION: Peptide 4

<400> SEQUENCE: 4

Glu Asp Leu Phe Ile Thr Ser Lys
1               5

<210> SEQ ID NO 5
<211> LENGTH: 12
<212> TYPE: PRT
<213> ORGANISM: Artificial sequence
<220> FEATURE:
<223> OTHER INFORMATION: Peptide 5

<400> SEQUENCE: 5

Glu Gly Asp Asp Leu Phe Pro Glu Lys Asp Gly Lys
1               5                   10

<210> SEQ ID NO 6
<211> LENGTH: 19
<212> TYPE: PRT
<213> ORGANISM: Artificial sequence
<220> FEATURE:
<223> OTHER INFORMATION: Peptide 6

<400> SEQUENCE: 6

His Ile Asp Cys Ala His Val Tyr Gly Asn Glu Pro Glu Val Gly Ala
1               5                   10                  15

Ala Ile Lys

<210> SEQ ID NO 7
<211> LENGTH: 7
<212> TYPE: PRT
<213> ORGANISM: Artificial sequence
<220> FEATURE:
<223> OTHER INFORMATION: Peptide 7

<400> SEQUENCE: 7

Lys Leu Ile Glu Phe Ser Lys
1               5

<210> SEQ ID NO 8
<211> LENGTH: 6
<212> TYPE: PRT
<213> ORGANISM: Artificial sequence
<220> FEATURE:
<223> OTHER INFORMATION: Peptide 8

<400> SEQUENCE: 8

Leu Ile Glu Phe Ser Lys
1               5

<210> SEQ ID NO 9
<211> LENGTH: 8
<212> TYPE: PRT
<213> ORGANISM: Artificial sequence
<220> FEATURE:
<223> OTHER INFORMATION: Peptide 9

<400> SEQUENCE: 9

Leu Val Asp Gln Gly Leu Thr Lys
1               5

<210> SEQ ID NO 10
<211> LENGTH: 9
<212> TYPE: PRT
<213> ORGANISM: Artificial sequence
```

```
<220> FEATURE:
<223> OTHER INFORMATION: Peptide 10

<400> SEQUENCE: 10

Arg Glu Asp Leu Phe Ile Thr Ser Lys
1               5

<210> SEQ ID NO 11
<211> LENGTH: 14
<212> TYPE: PRT
<213> ORGANISM: Artificial sequence
<220> FEATURE:
<223> OTHER INFORMATION: Peptide 11

<400> SEQUENCE: 11

Ser Ile Gly Val Ser Asn Phe Ser Ser Gln Gln Leu Glu Arg
1               5                   10

<210> SEQ ID NO 12
<211> LENGTH: 11
<212> TYPE: PRT
<213> ORGANISM: Artificial sequence
<220> FEATURE:
<223> OTHER INFORMATION: Peptide 12

<400> SEQUENCE: 12

Ser Lys Pro Gly Glu Val Thr Gln Ala Val Lys
1               5                   10

<210> SEQ ID NO 13
<211> LENGTH: 19
<212> TYPE: PRT
<213> ORGANISM: Artificial sequence
<220> FEATURE:
<223> OTHER INFORMATION: Peptide 13

<400> SEQUENCE: 13

Ser Lys Pro Gly Glu Val Thr Gln Ala Val Lys Asp Ala Ile Asp Val
1               5                   10                  15

Gly Tyr Arg

<210> SEQ ID NO 14
<211> LENGTH: 12
<212> TYPE: PRT
<213> ORGANISM: Artificial sequence
<220> FEATURE:
<223> OTHER INFORMATION: Peptide 14

<400> SEQUENCE: 14

Thr Leu Lys Ser Leu Thr Ser Ser Cys Leu Gln Arg
1               5                   10

<210> SEQ ID NO 15
<211> LENGTH: 17
<212> TYPE: PRT
<213> ORGANISM: Artificial sequence
<220> FEATURE:
<223> OTHER INFORMATION: Peptide 15

<400> SEQUENCE: 15

Thr Leu Tyr Ser Asp Val Asp Tyr Val Asp Thr Trp Lys Glu Leu Glu
1               5                   10                  15

Lys

<210> SEQ ID NO 16
```

-continued

```
<211> LENGTH: 8
<212> TYPE: PRT
<213> ORGANISM: Artificial sequence
<220> FEATURE:
<223> OTHER INFORMATION: Peptide 16

<400> SEQUENCE: 16

Thr Pro Ala Gln Ile Leu Leu Arg
1               5

<210> SEQ ID NO 17
<211> LENGTH: 6
<212> TYPE: PRT
<213> ORGANISM: Artificial sequence
<220> FEATURE:
<223> OTHER INFORMATION: Peptide 17

<400> SEQUENCE: 17

Val Leu Ala Asn Ala Arg
1               5

<210> SEQ ID NO 18
<211> LENGTH: 11
<212> TYPE: PRT
<213> ORGANISM: Artificial sequence
<220> FEATURE:
<223> OTHER INFORMATION: Peptide 18

<400> SEQUENCE: 18

Tyr Glu Lys Thr Pro Ala Gln Ile Leu Leu Arg
1               5                   10

<210> SEQ ID NO 19
<211> LENGTH: 12
<212> TYPE: PRT
<213> ORGANISM: Artificial sequence
<220> FEATURE:
<223> OTHER INFORMATION: Peptide 19

<400> SEQUENCE: 19

Tyr Gln Val Gln Gln Gly Asn Ile Thr Ile Pro Lys
1               5                   10

<210> SEQ ID NO 20
<211> LENGTH: 1737
<212> TYPE: DNA
<213> ORGANISM: Artificial sequence
<220> FEATURE:
<223> OTHER INFORMATION: Aldo-keto reductase AKR cDNA

<400> SEQUENCE: 20
ccagtgaggt gttggaggtg aatgagtgca aggttaacga atagtgttag acgttttact      60
gccacagtta tggcgtttaa gctagaaaaa actccgacsg tcaagttcaa caacggaatt     120
gaatttccca tctttggtct gggaacatgg aagtccaaac ctggtgaagt cactcaagct     180
gtgaaggatg ctattgacgt tgggtaccga cacatcgatt gcgctcacgt gtatggaaat     240
gaacctgaag ttgggccgc aattaaggcc aagatcggcg agaaagtcgt gaagcgtgag     300
gatctgttta tcacaagcaa gctgtggaac acattccatc gaccagactt ggttgccccct    360 gctataaagc agactttgac tgacttgggt ttggattact tggacctgta tttgattcac    420
tggccaatgg catacaagga aggtgatgac ctctttccgg agaaggatgg taaaactctg    480
tacagtgatg tggactatgt tgacacatgg aaggagttgg agaagttggt ggatcagggc    540
ctcaccaagt caattggggt gtcaaacttt agttcacagc agctagaacg agttctggcc    600
```

```
aatgctagaa tcaagccagt tacgaaccag gttgagtgtc acccatatttt gaaccaaaag      660 aagttgatag agtttagtaa agcaaaaggt gtaacaatca ctgcatacag cccgctgggc      720
tctccagatc gcccatgggc cacgcctgat gatcctcaac tgttggaaga tccaaaagtg      780
aaagctgtgg ctgcaaaata tgaaaagact cctgctcaga tccttctgag gtaccaggtg      840
cagcaaggta atattacaat ccccaaatct gtgacaaagt cacgtattgt agagaacgct      900
caaatctttg acttcgagct gtctgcagag gatgttgcca caattgattc ttttgactgc      960
aatggacgtg tctgtcacct ggactggatt aaagaccaca aggactatcc atttaacatt     1020
gaattctaag aagttgaagc cacaaatgaa gaatttgcaa gaaaaatatg aagtcactgc     1080
cagtccatgg agcgagttac gtaacgggga tggaggtgcc ttcacgatga ctgcagtcag     1140
tacagtaatc aggaatacgc acttgtatgc cagtaacgtt gcagttttga tgctagtcgt     1200
tcagcatcca agttggtatc atcatcttga tacattttt tcgtaattag gttaaatttt     1260
aattacactg gcttgtgtct gggcctgctt aattccaggc agccccagag ttttggcatt     1320
atatgcaact tacaaaaaca aatcatatga tgattagggt cattacttgc gtaaaaaata     1380
ttacagttgc atattttcca attgctacta ctgcaatagg acaggtttat gttgggacag     1440
aatttaaggt tatgtaaaat acttcatgaa ttacagtgat gtatattcat tttgtacata     1500
ttttgccagc tagtgttctt tcagacactc tgcccttcat tgttacaat atattcataa     1560 gtatttctcc cgtcattaca attgtttttc tttgtaataa tggtcgcatc agtgatctga     1620
tgagacatgt tctagctaag ctgtgtggct tcaaactagg gcttcactgt acagaaaata     1680
ctgaaataaa gtgacttcat gaaaagtaaa aaaaaaaaaa aaaaaaaaaa aaaaaaa       1737
```

<210> SEQ ID NO 21
<211> LENGTH: 335
<212> TYPE: PRT
<213> ORGANISM: Artificial sequence
<220> FEATURE:
<223> OTHER INFORMATION: Aldo-keto reductase AKR translation from cDNA

<400> SEQUENCE: 21

```
Met Ser Ala Arg Leu Thr Asn Ser Val Arg Arg Phe Thr Ala Thr Val
1               5                   10                  15

Met Ala Phe Lys Leu Glu Lys Thr Pro Thr Val Lys Phe Asn Asn Gly
                20                  25                  30

Ile Glu Phe Pro Ile Phe Gly Leu Gly Thr Trp Lys Ser Lys Pro Gly
            35                  40                  45

Glu Val Thr Gln Ala Val Lys Asp Ala Ile Asp Val Gly Tyr Arg His
        50                  55                  60

Ile Asp Cys Ala His Val Tyr Gly Asn Glu Pro Glu Val Gly Ala Ala
65                  70                  75                  80

Ile Lys Ala Lys Ile Gly Glu Lys Val Val Lys Arg Glu Asp Leu Phe
                85                  90                  95

Ile Thr Ser Lys Leu Trp Asn Thr Phe His Arg Pro Asp Leu Val Ala
            100                 105                 110

Pro Ala Ile Lys Gln Thr Leu Thr Asp Leu Gly Leu Asp Tyr Leu Asp
        115                 120                 125

Leu Tyr Leu Ile His Trp Pro Met Ala Tyr Lys Glu Gly Asp Asp Leu
    130                 135                 140

Phe Pro Glu Lys Asp Gly Lys Thr Leu Tyr Ser Asp Val Asp Tyr Val
145                 150                 155                 160
```

```
Asp Thr Trp Lys Glu Leu Glu Lys Leu Val Asp Gln Gly Leu Thr Lys
                165                 170                 175

Ser Ile Gly Val Ser Asn Phe Ser Ser Gln Gln Leu Glu Arg Val Leu
            180                 185                 190

Ala Asn Ala Arg Ile Lys Pro Val Thr Asn Gln Val Glu Cys His Pro
        195                 200                 205

Tyr Leu Asn Gln Lys Lys Leu Ile Glu Phe Ser Lys Ala Lys Gly Val
    210                 215                 220

Thr Ile Thr Ala Tyr Ser Pro Leu Gly Ser Pro Asp Arg Pro Trp Ala
225                 230                 235                 240

Thr Pro Asp Asp Pro Gln Leu Leu Glu Asp Pro Lys Val Lys Ala Val
                245                 250                 255

Ala Ala Lys Tyr Glu Lys Thr Pro Ala Gln Ile Leu Leu Arg Tyr Gln
            260                 265                 270

Val Gln Gln Gly Asn Ile Thr Ile Pro Lys Ser Val Thr Lys Ser Arg
        275                 280                 285

Ile Val Glu Asn Ala Gln Ile Phe Asp Phe Glu Leu Ser Ala Glu Asp
    290                 295                 300

Val Ala Thr Ile Asp Ser Phe Asp Cys Asn Gly Arg Val Cys His Leu
305                 310                 315                 320

Asp Trp Ile Lys Asp His Lys Asp Tyr Pro Phe Asn Ile Glu Phe
                325                 330                 335

<210> SEQ ID NO 22
<211> LENGTH: 1575
<212> TYPE: DNA
<213> ORGANISM: Artificial sequence
<220> FEATURE:
<223> OTHER INFORMATION: Catalase codon-optimized for Trichoplusia ni

<400> SEQUENCE: 22
gaattcatgg gtcaccacca tcatcaccat catcacggtt cttctccgga tccgatggcg      60
tccgatcagc tcgtgaacta caagaaaaag cagaccgata agactaaaat tgtaaccggc     120
catggtgccc cggttgacaa ccgtggcgct tctctcaccg tcggtcctcg tggtcctatg     180
ctgctccaag acattacctt cctcgatgaa ctggcgcact ttgatcgcga gcgcattcca     240
gaacgtgttg ttcatgcaaa aggtgcgggt gcgttcggtt atttcgaggt tactcatgat     300
attacgaagt actgcaaagc atccgttttc tctaagattg gtaagaagac tccaatcgcg     360
gttcgttttt ctaccgtagg tggcgagtct ggtagcgcgg acaccgtccg tgacccgcgt     420
ggtttcgctg ttaaattcta caccgaagac ggtatctggg acctggtcgg taataacact     480
ccgatcttct tcatccgtga tccgctgctg ttcccggttt tcatccatac ccagaaacgt     540
aacccggcga cccacctgaa agactgcgac atgttctggg atttcctgtc tctgcgccca     600
gaatctaccc accaggttat gtttctcttc agcgatcgtg gtatcccgga cggcttccgt     660
cacatgaatg gttacggctc tcatacgttt aaggcgatta atgataagaa tgaggccgtg     720
tatgtgaagt tccactataa aaccaaccag ggtatcaaaa acctcctcgc acagaaagcg     780
tctgaagttg cggttgcaga tccggactac tctatccgcg acctctacaa cgctattgca     840
cgtggccagt acccatcttg gaccctgtac atccaagtta tgacgtttga acaggcggaa     900
aaattccgtt ggaacccgtt cgacctgacg aaagtttggc cgcatgccga atatcctctg     960
attccggtag gtaaactggt tctcgatcgc aacccagcga attactttgc tgaggtagag    1020
cagattgcgt tctctccggc gcacatggtt ccgggtatcg aaccgtctcc tgataaaatg    1080
```

-continued

```
ctgcaaggcc gtctctttc ttactctgac acccaccgtc accgcctcgg tgcgaactat    1140
ctccagatcc cggtgaattg cccgtaccgt acccgtatca ccaactacca acgtgacggc    1200
cctcagacct tcacgaacaa ccaagaaggc gctccgaact actacccgaa ctctttctct    1260
ggtcctgaag atgttccgca ctgcgctgca attaagttcg cgtctacggg tgacgttgcg    1320
cgttacaact ctggcgacga agacaacttc tcccagccat ctctgttttg gaaaaagacc    1380
ctgaaaccgg aagagcgtga acgcctggta caaaacatcg ttgaccatgt taaagatgcc    1440
gcggacttcg tccaggagcg tacggttaaa aacttttctc aggttgacgc ggagtttggt    1500
cgtaagctga ccgaaggcct gcgtaaacac tctaaaaaca gctctatcgc atctgcgaac    1560
ctcgagtaac tgcag                                                     1575
```

<210> SEQ ID NO 23
<211> LENGTH: 520
<212> TYPE: PRT
<213> ORGANISM: Artificial sequence
<220> FEATURE:
<223> OTHER INFORMATION: Recombinant catalase

<400> SEQUENCE: 23

```
Met Gly His His His His His His His Gly Ser Ser Pro Asp Pro
1               5                   10                  15

Met Ala Ser Asp Gln Leu Val Asn Tyr Lys Lys Lys Gln Thr Asp Lys
            20                  25                  30

Thr Lys Ile Val Thr Gly His Gly Ala Pro Val Asp Asn Arg Gly Ala
        35                  40                  45

Ser Leu Thr Val Gly Pro Arg Gly Pro Met Leu Leu Gln Asp Ile Thr
    50                  55                  60

Phe Leu Asp Glu Leu Ala His Phe Asp Arg Glu Arg Ile Pro Glu Arg
65                  70                  75                  80

Val Val His Ala Lys Gly Ala Gly Ala Phe Gly Tyr Phe Glu Val Thr
                85                  90                  95

His Asp Ile Thr Lys Tyr Cys Lys Ala Ser Val Phe Ser Lys Ile Gly
            100                 105                 110

Lys Lys Thr Pro Ile Ala Val Arg Phe Ser Thr Val Gly Gly Glu Ser
        115                 120                 125

Gly Ser Ala Asp Thr Val Arg Asp Pro Arg Gly Phe Ala Val Lys Phe
    130                 135                 140

Tyr Thr Glu Asp Gly Ile Trp Asp Leu Val Gly Asn Asn Thr Pro Ile
145                 150                 155                 160

Phe Phe Ile Arg Asp Pro Leu Leu Phe Pro Val Phe Ile His Thr Gln
                165                 170                 175

Lys Arg Asn Pro Ala Thr His Leu Lys Asp Cys Asp Met Phe Trp Asp
            180                 185                 190

Phe Leu Ser Leu Arg Pro Glu Ser Thr His Gln Val Met Phe Leu Phe
        195                 200                 205

Ser Asp Arg Gly Ile Pro Asp Gly Phe Arg His Met Asn Gly Tyr Gly
    210                 215                 220

Ser His Thr Phe Lys Ala Ile Asn Asp Lys Asn Glu Ala Val Tyr Val
225                 230                 235                 240

Lys Phe His Tyr Lys Thr Asn Gln Gly Ile Lys Asn Leu Leu Ala Gln
                245                 250                 255

Lys Ala Ser Glu Val Ala Val Ala Asp Pro Asp Tyr Ser Ile Arg Asp
            260                 265                 270
```

```
Leu Tyr Asn Ala Ile Ala Arg Gly Gln Tyr Pro Ser Trp Thr Leu Tyr
            275                 280                 285

Ile Gln Val Met Thr Phe Glu Gln Ala Glu Lys Phe Arg Trp Asn Pro
        290                 295                 300

Phe Asp Leu Thr Lys Val Trp Pro His Ala Glu Tyr Pro Leu Ile Pro
305                 310                 315                 320

Val Gly Lys Leu Val Leu Asp Arg Asn Pro Ala Asn Tyr Phe Ala Glu
                325                 330                 335

Val Glu Gln Ile Ala Phe Ser Pro Ala His Met Val Pro Gly Ile Glu
            340                 345                 350

Pro Ser Pro Asp Lys Met Leu Gln Gly Arg Leu Phe Ser Tyr Ser Asp
        355                 360                 365

Thr His Arg His Arg Leu Gly Ala Asn Tyr Leu Gln Ile Pro Val Asn
370                 375                 380

Cys Pro Tyr Arg Thr Arg Ile Thr Asn Tyr Gln Arg Asp Gly Pro Gln
385                 390                 395                 400

Thr Phe Thr Asn Asn Gln Glu Gly Ala Pro Asn Tyr Tyr Pro Asn Ser
                405                 410                 415

Phe Ser Gly Pro Glu Asp Val Pro His Cys Ala Ala Ile Lys Phe Ala
            420                 425                 430

Ser Thr Gly Asp Val Ala Arg Tyr Asn Ser Gly Asp Glu Asp Asn Phe
        435                 440                 445

Ser Gln Pro Ser Leu Phe Trp Lys Lys Thr Leu Lys Pro Glu Glu Arg
    450                 455                 460

Glu Arg Leu Val Gln Asn Ile Val Asp His Val Lys Asp Ala Ala Asp
465                 470                 475                 480

Phe Val Gln Glu Arg Thr Val Lys Asn Phe Ser Gln Val Asp Ala Glu
                485                 490                 495

Phe Gly Arg Lys Leu Thr Glu Gly Leu Arg Lys His Ser Lys Asn Ser
            500                 505                 510

Ser Ile Ala Ser Ala Asn Leu Glu
        515                 520

<210> SEQ ID NO 24
<211> LENGTH: 1739
<212> TYPE: DNA
<213> ORGANISM: Artificial sequence
<220> FEATURE:
<223> OTHER INFORMATION: Native aldo-keto reductase from Reticulitermes
      flavipes

<400> SEQUENCE: 24
agccagtgag gtgttggagg tgaatgagtg caaggttaac gaatagtgtt agacgtttta      60
ctgccacagt tatggcgttt aagctagaaa aaactccgac sgtcaagttc aacaacggaa    120
ttgaatttcc catctttggt ctgggaacat ggaagtccaa acctggtgaa gtcactcaag    180
ctgtgaagga tgctattgac gttgggtacc gacacatcga ttgcgctcac gtgtatggaa    240
atgaacctga agttggggcc gcaattaagg ccaagatcgg cgagaaagtc gtgaagcgtg    300
aggatctgtt tatcacaagc aagctgtgga acacattcca tcgaccagac ttggttgccc    360
ctgctataaa gcagactttg actgacttgg gtttggatta cttggacctg tatttgattc    420
actggccaat ggcatacaag gaaggtgatg acctctttcc ggagaaggat ggtaaaactc    480
tgtacagtga tgtggactat gttgacacat ggaggagtt ggagaagttg gtggatcagg    540
gcctcaccaa gtcaattggg gtgtcaaact ttagttcaca gcagctagaa cgagttctgg    600
```

```
ccaatgctag aatcaagcca gttacgaacc aggttgagtg tcacccatat ttgaaccaaa      660
agaagttgat agagtttagt aaagcaaaag gtgtaacaat cactgcatac agcccgctgg      720
gctctccaga tcgcccatgg gccacgcctg atgatcctca actgttggaa gatccaaaag      780
tgaaagctgt ggctgcaaaa tatgaaaaga ctcctgctca gatccttctg aggtaccagg      840
tgcagcaagg taatattaca atccccaaat ctgtgacaaa gtcacgtatt gtagagaacg      900
ctcaaatctt tgacttcgag ctgtctgcag aggatgttgc cacaattgat tcttttgact      960
gcaatggacg tgtctgtcac ctggactgga ttaaagacca caaggactat ccatttaaca     1020
ttgaattcta agaagttgaa gccacaaatg aagaatttgc aagaaaaata tgaagtcact     1080
gccagtccat ggagcgagtt acgtaacggg gatggaggtg ccttcacgat gactgcagtc     1140
agtacagtaa tcaggaatac gcacttgtat gccagtaacg ttgcagtttt gatgctagtc     1200
gttcagcatc caagttggta tcatcatctt gatacatttt tttcgtaatt aggttaaatt     1260
ttaattacac tggcttgtgt ctgggcctgc ttaattccag gcagcccag agttttggca      1320 ttatatgcaa cttacaaaaa caaatcatat gatgattagg gtcattactt gcgtaaaaaa     1380
tattacagtt gcatattttc caattgctac tactgcaata ggacaggttt atgttgggac     1440
agaatttaag gttatgtaaa atacttcatg aattacagtg atgtatattc attttgtaca     1500
tattttgcca gctagtgttc tttcagacac tctgcccttc atttgttaca atatattcat     1560
aagtatttct cccgtcatta caattgtttt tctttgtaat aatggtcgca tcagtgatct     1620
gatgagacat gttctagcta agctgtgtgg cttcaaacta gggcttcact gtacagaaaa     1680
tactgaaata aagtgacttc atgaaaagta aaaaaaaaaa aaaaaaaaa aaaaaaaaa      1739

<210> SEQ ID NO 25
<211> LENGTH: 31
<212> TYPE: DNA
<213> ORGANISM: Artificial sequence
<220> FEATURE:
<223> OTHER INFORMATION: AKR forward primer

<400> SEQUENCE: 25
tctagaatga gtgcaaggtt aacgaatagt g                                     31

<210> SEQ ID NO 26
<211> LENGTH: 61
<212> TYPE: DNA
<213> ORGANISM: Artificial sequence
<220> FEATURE:
<223> OTHER INFORMATION: AKR reverse primer

<400> SEQUENCE: 26
cggccgttag tgatgatggt gatgatgacc tccgaattca atgttaaatg gatagtcctt      60
g                                                                      61

<210> SEQ ID NO 27
<211> LENGTH: 1052
<212> TYPE: DNA
<213> ORGANISM: Artificial sequence
<220> FEATURE:
<223> OTHER INFORMATION: Aldo-keto reductase codon-optimized for
      Tricholusia ni

<400> SEQUENCE: 27
ggatcctatg agtgcaaggt taacgaattc tgttagacgt tttactgcca cagttatggc      60
cttcaagctg gaaaagacgc ctaccgtcaa gttcaacaac ggtatcgagt ttcctatctt     120
```

-continued

```
tggtctcggt acgtggaagt ctaagcctgg tgaggtcacc caagctgtca aggacgctat    180
cgacgtcggt taccgtcaca ttgactgtgc tcatgtgtac ggtaatgaac ctgaagtcgg    240
cgcagctatc aaggctaaga tcggtgaaaa ggtggtgaag cgtgaggacc tcttcatcac    300
gtctaagctg tggaatacct tccaccgtcc tgatctggtc gctcctgcta ttaagcagac    360
gctcaccgac ctcggtctgg attacctgga cctgtacctg atccactggc ctatggctta    420
caaggaaggt gacgacctgt tccctgaaaa ggatggtaag accctgtatt ctgatgtcga    480
ctacgtcgac acttggaagg aactggagaa gctggtggac cagggtctca ccaagtctat    540
cggtgtgtct aacttctctt ctcagcagct cgaacgtgtg ctggctaacg cccgtatcaa    600
gcctgtcacg aaccaggtcg aatgccaccc atatctgaac caaaagaagc tgatcgaatt    660
ttccaaggct aagggtgtaa cgatcaccgc ttactctcct ctgggctccc ctgaccgtcc    720
atgggctacc cctgatgacc ctcaactgct cgaagaccct aaggtcaagg ccgtggcagc    780
taagtacgaa aagactcctg ctcaaatcct gctgcgttac caagtccagc aaggtaacat    840
cactatccct aagtctgtga ctaagtctcg tatcgtcgaa aacgctcaga ttttcgattt    900
cgaactgtct gctgaagacg tggctaccat cgactctttc gactgcaatg gtcgtgtctg    960
ccatctggac tggatcaagg accacaagga ctatcctttc aacattgagt tcggccgtgg   1020
ttctcatcac caccatcatc atcattaatt aa                                 1052
```

<210> SEQ ID NO 28
<211> LENGTH: 335
<212> TYPE: PRT
<213> ORGANISM: Artificial sequence
<220> FEATURE:
<223> OTHER INFORMATION: AKR recombinant protein

<400> SEQUENCE: 28

```
Met Ser Ala Arg Leu Thr Asn Ser Val Arg Arg Phe Thr Ala Thr Val
1               5                   10                  15

Met Ala Phe Lys Leu Glu Lys Thr Pro Thr Val Lys Phe Asn Asn Gly
            20                  25                  30

Ile Glu Phe Pro Ile Phe Gly Leu Gly Thr Trp Lys Ser Lys Pro Gly
        35                  40                  45

Glu Val Thr Gln Ala Val Lys Asp Ala Ile Asp Val Gly Tyr Arg His
    50                  55                  60

Ile Asp Cys Ala His Val Tyr Gly Asn Glu Pro Glu Val Gly Ala Ala
65                  70                  75                  80

Ile Lys Ala Lys Ile Gly Glu Lys Val Val Lys Arg Glu Asp Leu Phe
                85                  90                  95

Ile Thr Ser Lys Leu Trp Asn Thr Phe His Arg Pro Asp Leu Val Ala
            100                 105                 110

Pro Ala Ile Lys Gln Thr Leu Thr Asp Leu Gly Leu Asp Tyr Leu Asp
        115                 120                 125

Leu Tyr Leu Ile His Trp Pro Met Ala Tyr Lys Glu Gly Asp Asp Leu
    130                 135                 140

Phe Pro Glu Lys Asp Gly Lys Thr Leu Tyr Ser Asp Val Asp Tyr Val
145                 150                 155                 160

Asp Thr Trp Lys Glu Leu Glu Lys Leu Val Asp Gln Gly Leu Thr Lys
                165                 170                 175

Ser Ile Gly Val Ser Asn Phe Ser Ser Gln Gln Leu Glu Arg Val Leu
            180                 185                 190

Ala Asn Ala Arg Ile Lys Pro Val Thr Asn Gln Val Glu Cys His Pro
```

```
                195                 200                 205
Tyr Leu Asn Gln Lys Lys Leu Ile Glu Phe Ser Lys Ala Lys Gly Val
    210                 215                 220
Thr Ile Thr Ala Tyr Ser Pro Leu Gly Ser Pro Asp Arg Pro Trp Ala
225                 230                 235                 240
Thr Pro Asp Asp Pro Gln Leu Leu Glu Asp Pro Lys Val Lys Ala Val
                245                 250                 255
Ala Ala Lys Tyr Glu Lys Thr Pro Ala Gln Ile Leu Leu Arg Tyr Gln
            260                 265                 270
Val Gln Gln Gly Asn Ile Thr Ile Pro Lys Ser Val Thr Lys Ser Arg
        275                 280                 285
Ile Val Glu Asn Ala Gln Ile Phe Asp Phe Glu Leu Ser Ala Glu Asp
    290                 295                 300
Val Ala Thr Ile Asp Ser Phe Asp Cys Asn Gly Arg Val Cys His Leu
305                 310                 315                 320
Asp Trp Ile Lys Asp His Lys Asp Tyr Pro Phe Asn Ile Glu Phe
                325                 330                 335

<210> SEQ ID NO 29
<211> LENGTH: 319
<212> TYPE: PRT
<213> ORGANISM: Artificial sequence
<220> FEATURE:
<223> OTHER INFORMATION: AKR recombinant mature protein

<400> SEQUENCE: 29

Met Ala Phe Lys Leu Glu Lys Thr Pro Thr Val Lys Phe Asn Asn Gly
1               5                   10                  15
Ile Glu Phe Pro Ile Phe Gly Leu Gly Thr Trp Lys Ser Lys Pro Gly
                20                  25                  30
Glu Val Thr Gln Ala Val Lys Asp Ala Ile Asp Val Gly Tyr Arg His
            35                  40                  45
Ile Asp Cys Ala His Val Tyr Gly Asn Glu Pro Glu Val Gly Ala Ala
    50                  55                  60
Ile Lys Ala Lys Ile Gly Glu Lys Val Val Lys Arg Glu Asp Leu Phe
65                  70                  75                  80
Ile Thr Ser Lys Leu Trp Asn Thr Phe His Arg Pro Asp Leu Val Ala
                85                  90                  95
Pro Ala Ile Lys Gln Thr Leu Thr Asp Leu Gly Leu Asp Tyr Leu Asp
            100                 105                 110
Leu Tyr Leu Ile His Trp Pro Met Ala Tyr Lys Glu Gly Asp Asp Leu
        115                 120                 125
Phe Pro Glu Lys Asp Gly Lys Thr Leu Tyr Ser Asp Val Asp Tyr Val
    130                 135                 140
Asp Thr Trp Lys Glu Leu Glu Lys Leu Val Asp Gln Gly Leu Thr Lys
145                 150                 155                 160
Ser Ile Gly Val Ser Asn Phe Ser Ser Gln Leu Glu Arg Val Leu
                165                 170                 175
Ala Asn Ala Arg Ile Lys Pro Val Thr Asn Gln Val Glu Cys His Pro
            180                 185                 190
Tyr Leu Asn Gln Lys Lys Leu Ile Glu Phe Ser Lys Ala Lys Gly Val
        195                 200                 205
Thr Ile Thr Ala Tyr Ser Pro Leu Gly Ser Pro Asp Arg Pro Trp Ala
    210                 215                 220
Thr Pro Asp Asp Pro Gln Leu Leu Glu Asp Pro Lys Val Lys Ala Val
```

```
                225                 230                 235                 240
Ala Ala Lys Tyr Glu Lys Thr Pro Ala Gln Ile Leu Leu Arg Tyr Gln
                    245                 250                 255

Val Gln Gln Gly Asn Ile Thr Ile Pro Lys Ser Val Thr Lys Ser Arg
                260                 265                 270

Ile Val Glu Asn Ala Gln Ile Phe Asp Phe Glu Leu Ser Ala Glu Asp
            275                 280                 285

Val Ala Thr Ile Asp Ser Phe Asp Cys Asn Gly Arg Val Cys His Leu
        290                 295                 300

Asp Trp Ile Lys Asp His Lys Asp Tyr Pro Phe Asn Ile Glu Phe
305                 310                 315

<210> SEQ ID NO 30
<211> LENGTH: 1878
<212> TYPE: DNA
<213> ORGANISM: Artificial sequence
<220> FEATURE:
<223> OTHER INFORMATION: Catalase cDNA

<400> SEQUENCE: 30
```

| | | | | |
|---|---|---|---|---|
| ggcagtagtt | ggtgtgcgtt | tgtgtgagca | gttggtggac | gtgtgatatt | cgtttgaaaa |   60 |
| tgtcttctcc | ggatccagct | tccgatcagt | tagtaaatta | caagaagaaa | caaaccgata |  120 |
| aaacgaagat | tgttactgga | catggagcac | cagttgataa | ccgtggggcc | agtttaactg |  180 |
| tggggccccg | gggtcccatg | ctgttacaag | atattacgtt | tctaratgaa | ctcgcacact |  240 |
| ttgacagaga | acgtatccca | gagagagtgg | tccatgccaa | aggggcaggt | gcatttggct |  300 |
| actttgaagt | grcacatgac | atcacaaaat | attgtaaggc | gagtgttttc | tcaaaaattg |  360 |
| gcaagaagac | gccgattgct | gtaaggtttt | ctacagtagg | tggtgagagt | gggtcagctg |  420 |
| acacagtcag | agatcctcgg | ggctttgctg | tgaaatttta | cactgaagat | ggcatctggg |  480 |
| acctggtggg | taacaacaca | ccaatcttct | ttatcaggga | cccattgctg | tttcctgtat |  540 |
| ttatccacac | acagaagaga | aatcctgcaa | cacatctgaa | ggattgtgac | atgttctggg |  600 |
| acttcctctc | tctgcgacct | gaatccacac | atcaagtcat | gtttctgttt | tctgacagag |  660 |
| gcattccaga | tggatttcgt | catatgaatg | gttatggctc | tcatacattc | aaggctataa |  720 |
| atgataagaa | cgaggctgta | tacgtgaaat | tccattataa | gacaaatcag | ggcatcaaaa |  780 |
| acttactggc | acagaaagcc | tcagaagtag | ctgtagcaga | ccctgattac | tctatccgag |  840 |
| acttgtacaa | tgctatcgca | cgaggccagt | acccatcatg | gactttgtac | atccaagtga |  900 |
| tgactttga | acaagcagag | aaattcaggt | ggaaccccct | tgacctcact | aaggtttggc |  960 |
| cgcatgcaga | gtatccacta | atccccgtgg | gcaaacttgt | gcttgaccgc | aaccctgcca | 1020 |
| attactttgc | tgaggtggag | cagattgcat | tcagccctgc | acacatggtg | cctggcattg | 1080 |
| aaccaagtcc | tgacaagatg | ttgcagggtc | ggctgttcag | ctactcagac | acgcaccgtc | 1140 |
| accgactggg | agccaactac | ctgcagattc | cagtraactg | tccatatcgt | acgcgtataa | 1200 |
| ccaactacca | acgcgacgga | ccgcagacgt | ttaccaacaa | ccaggaggga | gcaccaaact | 1260 |
| actacccaaa | cagctttagt | gggcccgaag | atgtgccaca | ctgtgctgct | atcaagtttg | 1320 |
| catctacagg | agatgtagcc | aggtacaact | ctggagatga | ggataacttt | agccagccct | 1380 |
| ctcttttctg | gaagaagacc | ctcaaaccgg | aggagcgaga | acgtctggtg | cagaacattg | 1440 |
| tggatcacgt | gaaggatgct | gctgactttg | tacaggaacg | cacagtgaag | aatttcagcc | 1500 |
| aggtggatgc | tgagtttggt | cgcaaattga | ctgagggact | gcgtaagcat | tccaagaaca | 1560 |

```
gcagcattgc ttcagcaaat ctttgagttg ctgcgtggaa acaaactcaa ggttttgtg      1620 gggcaaatta ttgattttga agacttcaat acttaacatt tcatgggtgt ttaacaggtg     1680
cttaatgtgt ttggtacttt tatgtactca ggggccaggc atyttattct gtaacttcag     1740
ttaatatgct gttacacaca tcaatatgtt gkgtagagag ggtaacttgt gtatgttgaa     1800
aacataaggg ggaaaataaa cattttagta aaaaaaaaa aaaaaaaaa aaaaaaaag        1860 aaaaaaaaaa aaaaaaa                                                    1878
```

<210> SEQ ID NO 31
<211> LENGTH: 1471
<212> TYPE: DNA
<213> ORGANISM: Artificial sequence
<220> FEATURE:
<223> OTHER INFORMATION: GHF7-3 cellulase cDNA
<220> FEATURE:
<221> NAME/KEY: misc_feature
<222> LOCATION: (1028)..(1028)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1118)..(1118)
<223> OTHER INFORMATION: n is a, c, g, or t
<220> FEATURE:
<221> NAME/KEY: misc_feature
<222> LOCATION: (1152)..(1152)
<223> OTHER INFORMATION: n is a, c, g, or t

<400> SEQUENCE: 31

```
ttttcatttt ctgaatcatg ctgacttttg tggttgtgtt gctttcattg gttgtgtctc      60
ttgagattgg gactcaacaa acggagactc atcctaaatt gacgtggcag aatggatcaa     120
gttcagtgtc agggtctatt gttcttgatt cgaattggag atgggttcat gacagcggga     180
cgactaattg ttatgatggg aatctgtgga gcagtgatct tgtccaagt tcagatacat      240 gcacacagaa atgttatatt gagggagcag attattcggg aacttacgga attacgacga     300
gtggttcaaa gttgacgctg aaatttgtta cgaaaggatc gtattcaaca acatcggaa      360 gtcgtgttta cttgttgaaa gatgacaaca cttatgaaac attcaaattg aagaataagg     420
aatttacatt tacggtggat gattctcaac ttgattgcgg actgaatggg gcattgtatt     480
ttgttgcgat ggatgcagat ggtggaaaag caaaatattc agctttcaag ccaggggcta     540
aatatggaat gggatattgt gatgcacagt gcccacatga catgaagttt atcagtggaa     600
aggctaatgt tgatgactgg aaaccacaag acaatgatga aaattcagga aatgggaaac     660
ttggaacatg ctgttcggaa atggatattt gggaggaaa tgcaaagtca caggcatata     720
cagtgcacgc ttgcacgaaa agtggacaat atgaatgtac gggaactgct tgcggagact     780
cagataacag gtatggggga acttgcgaca agatggatg cgactatgct tcatatagat     840
ggggagacca ctcgttctat ggtgagggta agactgtgga cacgaaacag ccagttacag     900
ttgtcactca gtttatcgga gatccgttga cagaaatcag acgggtttat gttcaaggtg     960
ggaaagtgat tgagaactcg aaaacatcga acttggcttc aacatatgat tcgatcaccg    1020
atgcattntg cgacgcgacg aaagcagcga gtggcgatac taacgatttt aaggcgaaag    1080
gaggcatggc gggattcagt aagaatctgg acnctccnca gtattggtt ttgtcattgt      1140 gggatgatca cncagcgaat atgttgtggc ttgattcgac gtatccaact gattccagtg    1200
atccaacagc agcacgtgga ccttgtgcga catcatcagg tgttccaaaa gacgttgaaa    1260
```

```
gcgcgcaagc caatgctcaa gttgtatttt cggacattaa gtttggggcc atcaactcga    1320
cttataaagc caattaaaaa ccctttttga gagctcaatt tgggtaagat tttttctttt    1380
tatttgagag tcattcattg tgttttttta aaagtggtg tttaattatt tttttttttt     1440
tggaagaatt gtttatttgg gaattgatta a                                    1471
```

<210> SEQ ID NO 32
<211> LENGTH: 693
<212> TYPE: DNA
<213> ORGANISM: Artificial sequence
<220> FEATURE:
<223> OTHER INFORMATION: GHF11-1 hemicellulase codon-optimized for
      Trichoplusia ni

<400> SEQUENCE: 32

```
ctgcagatga aattaatctc tgttttgttt gcgcttgctg tagcgaaatc gttcgaagat     60
cttgttaata ctactgcgac gtcgaatgca tgtaccgtga catcaaatca acagggtacg    120
tgtgatggcg ttgcgtatga attgtggatg tcaggatctg gcggaagctg cacaatcaaa    180
ggtggtggta gtgctgcatt tagcgcgaaa tggagcaaca gtggcgattt cttgtgtcgt    240
gctggtcttg gatcaggcag tgcaagtggc atcaaagcta gctttgcata cacaaaatca    300
ggcagtggtg gtggctattc gtttattggg atctatggct ggaccaccaa ccctctggtt    360
gaatactaca ttgtgatga ttggttctca ggaggtggta actctggcgg atctcagaaa     420
ggttctttca cccaagatgg tgcgacatat aacatctggc aacacactca gaacaaccag    480
ccatcgatcc aggaacagc gacatttgag caattcttca gcatccgctc aagccagcgc    540
acatccggtg atatcaatat ctcagctcac tttgacaaat ggagcagcct gggatgaga    600 atgggcagcc tgtatgaggc gaaattgctg gttgaggctg gtggtggtag tggaaacatt    660
gactattcgt ctggcagcgt gaccaggggt acc                                  693
```

<210> SEQ ID NO 33
<211> LENGTH: 229
<212> TYPE: PRT
<213> ORGANISM: Artificial sequence
<220> FEATURE:
<223> OTHER INFORMATION: Recombinant GHF11-1 hemicellulase

<400> SEQUENCE: 33

```
Met Lys Leu Ile Ser Val Leu Phe Ala Leu Ala Val Ala Lys Ser Phe
1               5                   10                  15

Glu Asp Leu Val Asn Thr Thr Ala Thr Ser Asn Ala Cys Thr Val Thr
            20                  25                  30

Ser Asn Gln Gln Gly Thr Cys Asp Gly Val Ala Tyr Glu Leu Trp Met
        35                  40                  45

Ser Gly Ser Gly Gly Ser Cys Thr Ile Lys Gly Gly Ser Ala Ala
    50                  55                  60

Phe Ser Ala Lys Trp Ser Asn Ser Gly Asp Phe Leu Cys Arg Ala Gly
65                  70                  75                  80

Leu Gly Ser Gly Ser Ala Ser Gly Ile Lys Ala Ser Phe Ala Tyr Thr
                85                  90                  95

Lys Ser Gly Ser Gly Gly Tyr Ser Phe Ile Gly Ile Tyr Gly Trp
                100                 105                 110

Thr Thr Asn Pro Leu Val Glu Tyr Tyr Ile Val Asp Asp Trp Phe Ser
            115                 120                 125

Gly Gly Gly Asn Ser Gly Gly Ser Gln Lys Gly Ser Phe Thr Gln Asp
```

```
                130                 135                 140
Gly Ala Thr Tyr Asn Ile Trp Gln His Thr Gln Asn Asn Gln Pro Ser
145                 150                 155                 160

Ile Gln Gly Thr Ala Thr Phe Glu Gln Phe Phe Ser Ile Arg Ser Ser
                165                 170                 175

Gln Arg Thr Ser Gly Asp Ile Asn Ile Ser Ala His Phe Asp Lys Trp
            180                 185                 190

Ser Ser Leu Gly Met Arg Met Gly Ser Leu Tyr Glu Ala Lys Leu Leu
        195                 200                 205

Val Glu Ala Gly Gly Ser Gly Asn Ile Asp Tyr Ser Ser Gly Ser
    210                 215                 220

Val Thr Arg Gly Thr
225

<210> SEQ ID NO 34
<211> LENGTH: 214
<212> TYPE: PRT
<213> ORGANISM: Artificial sequence
<220> FEATURE:
<223> OTHER INFORMATION: Mature GHF11-1 hemicellulase

<400> SEQUENCE: 34

Phe Glu Asp Leu Val Asn Thr Thr Ala Thr Ser Asn Ala Cys Thr Val
1               5                   10                  15

Thr Ser Asn Gln Gln Gly Thr Cys Asp Gly Val Ala Tyr Glu Leu Trp
            20                  25                  30

Met Ser Gly Ser Gly Ser Cys Thr Ile Lys Gly Gly Ser Ala
        35                  40                  45

Ala Phe Ser Ala Lys Trp Ser Asn Ser Gly Asp Phe Leu Cys Arg Ala
    50                  55                  60

Gly Leu Gly Ser Gly Ser Ala Ser Gly Ile Lys Ala Ser Phe Ala Tyr
65                  70                  75                  80

Thr Lys Ser Gly Ser Gly Gly Tyr Ser Phe Ile Gly Ile Tyr Gly
                85                  90                  95

Trp Thr Thr Asn Pro Leu Val Glu Tyr Tyr Ile Val Asp Asp Trp Phe
            100                 105                 110

Ser Gly Gly Asn Ser Gly Gly Ser Gln Lys Gly Ser Phe Thr Gln
        115                 120                 125

Asp Gly Ala Thr Tyr Asn Ile Trp Gln His Thr Gln Asn Asn Gln Pro
    130                 135                 140

Ser Ile Gln Gly Thr Ala Thr Phe Glu Gln Phe Phe Ser Ile Arg Ser
145                 150                 155                 160

Ser Gln Arg Thr Ser Gly Asp Ile Asn Ile Ser Ala His Phe Asp Lys
                165                 170                 175

Trp Ser Ser Leu Gly Met Arg Met Gly Ser Leu Tyr Glu Ala Lys Leu
            180                 185                 190

Leu Val Glu Ala Gly Gly Ser Gly Asn Ile Asp Tyr Ser Ser Gly
        195                 200                 205

Ser Val Thr Arg Gly Thr
    210

<210> SEQ ID NO 35
<211> LENGTH: 1985
<212> TYPE: DNA
<213> ORGANISM: Artificial sequence
<220> FEATURE:
<223> OTHER INFORMATION: Laccase LacA cDNA
```

<400> SEQUENCE: 35

```
atacggccct atcagtttac agatcggacg cctacattat gttgccttgc gtcctgcttg    60
cttgcgcaat tggtgtggct tctgcaacat cagtgctcct gaattcatac cttcagccca   120
acgatgacat tgatcgaaac acgtacctcc taaatgcaaa aagcaacaac tgtgcccgta   180
tatgcaatgg gacagaggcg cccaaaatct gctactacca atggacaatt gagaactacg   240
tgactctgtc agaagcgtgt gacaattgtc ccttgaatgt gacggcctgt tacaacgcac   300
agtgcatcac agctgatgga tatgagcgca gtatcctttc ggtaaacagg aaactaccgg   360
ggccttccat cgaggtgtgc ctcagagaca gagtaattgt ggatataacc aacaacatgg   420
cagggaggac tactagcatc cactggcatg gggtatttca gaagggtccc agtacatgg   480
acggagttcc catggtaacc cagtgcacta tacatgaggg tgacacattc cggtacgact   540
ttatcgctaa caacgaggga actcatttct ggcattccca tgacggtttg cagaagctcg   600
atggcgtgac aggtaacttg gtggttaggg tgcctaaaaa tttcgacccg aacggacaac   660
tgtacgattt cgatctacca gaacacaaaa ttttcatcag cgactggcta catctttccg   720
cagatgacca ctttcccgga ctccgagcga caaatccagg acaagatgct aactcctttc   780
tcattaacgg cagaggacgt accttgattg gaactcagtc caccaacaca ccgtatgcgc   840
agataaatgt gcagtggggc aggaggtacc ggcttgcat tgtgggctcc ctgtgcactg   900
tgtgccccac acagctcacc attgacgggc acaaaattac agtcatagcc actgacggca   960
attctgtggc tcctgccaga gtcgactccc tcatcattta ctctggtgaa agatacgacg  1020
tcgtgttaga agccactaat acggaaggat cttactggat ccatctaaaa ggcctcgcca  1080
cttgtgttgg aagtagagtt taccagctgg gggtgttgca atatgaaaat acaacaacca  1140
ataaactgca tgctctgaca cctgatccag gttacgacgg attcccgcaa ccagcaagct  1200
accgggtcct gaacccagag aacgcaagct gtagcatcgg ctcgacaggc ctatgcgtca  1260
cgcaactcgc gaactcggac cccgtgccac gggacatcct aacccagctc ccggacatca  1320
actatcttct ccaatttgga tttgaaactt tcgactccag aagtttcttc aaagcttacg  1380
acagatattt tgtcagcccc tttctcgagt tactcagcag taccgtcaac aacatttctt  1440
tcgtttcgcc cccatctccg ctcctctcac aaaggggga tgtaccagac gacatcctat  1500
gcccgacggg ggctgatggc ctgccccagt gtcccgagg aaactcctac tgcacatgtg  1560
tccatgtcat caaaatcaaa ctgggtgctt tggtgcagat catcctgtcg gaccagtcac  1620
ccaaatccga cctgaaccat ccgttccata tacacggaca tgcgttttac gtcctgggca  1680
tggggcaata cgctgcagga cagacggcgc aggacctcct taactccttg aagagtaacg  1740
tgagtagtgt gtcccctgcg ccggttctta aagataccgt cgcagttcca tctggcggct  1800
acgcgatcat caagttcaga ccaaaaaaacc ctggttactg gttccttcac tgccacttcc  1860
tgtaccatgt agcgaccggg atgagtgttg tgctccaggt gggagaaaca agtgactatc  1920
ccctacacc agacggcttc cccaagtgtg gaagcttcac acctcccgtg aacaccaact  1980
gaagt                                                             1985
```

<210> SEQ ID NO 36
<211> LENGTH: 28
<212> TYPE: DNA
<213> ORGANISM: Artificial sequence
<220> FEATURE:
<223> OTHER INFORMATION: Laccase A forward primer

<400> SEQUENCE: 36

```
tctagaatgt tgccttgcgt cctgcttg                                        28
```

<210> SEQ ID NO 37
<211> LENGTH: 54
<212> TYPE: DNA
<213> ORGANISM: Artificial sequence
<220> FEATURE:
<223> OTHER INFORMATION: Laccase A reverse primer

<400> SEQUENCE: 37

```
cggccgttag tgatgatggt gatgatgacc tccgttggtg ttcacgggag gtgt           54
```

<210> SEQ ID NO 38
<211> LENGTH: 1489
<212> TYPE: DNA
<213> ORGANISM: Artificial sequence
<220> FEATURE:
<223> OTHER INFORMATION: GHF9 Cell-1 cellulase cDNA

<400> SEQUENCE: 38

```
ccactaccag ccgccatgaa ggtcttcgtt tgtcttctgt ctgcactggc gctttgccaa     60
gctgcttacg actataagac agtactaagc aattcgctac ttttctacga ggctcagcga   120
tcgggaaaat tgccgtctga tcagaaggtc acgtggagga aggattccgc ccttaacgac   180
aagggccaga agggcgagga cctgacagga ggatactatg acgctggtga ttttgtgaag   240
ttcggcttcc ctatggcgta cacagtcacc gtcctcgctt ggggtgttat agactacgaa   300
tcagcgtatt ctgcagcagg agctctggat agtggtcgca aggctcttaa atatggcacg   360
gactacttcc tcaaggcgca cacggccgcg aacgaattct acggacaagt gggccaggga   420
gatgtcgacc acgcctactg gggacgtcca gaagacatga cgatgtccag acctgcctac   480
aagatcgaca cgtcgaaacc agggtctgac ctggcagccg agacagccgc cgccctcgct   540
gcaactgcca tcgcctacaa gagtgctgac gcaacttatt ccaacaactt gatcacccac   600
gccaagcagc ttttcgactt cgccaacaat tatcgcggca atacagtga ttcaatcacc    660
gacgcgaaga atttctacgc gtccggagac tacaaggacg agttagtatg ggcagccgca   720
tggctctaca gggcgaccaa cgacaacacc tatctgacta agctgaatc gctatacaac    780
gaattcggcc tcgaaactg gaacggtgcc ttcaactggg ataacaagat ctccggtgta    840
caggttctac tggccaagct cacaagcaag caggcataca aggacaaggt acaaggctac   900
gtcgattact tgatttcgtc tcagaagaag acacccaagg gtctcgtata catcgaccag   960
tggggtaccc tgcgacatgc tgccaattct gctctcattg ctctgcaggc agccgacctg  1020
ggtatcaatg ctgctactta cgcgcgtat gccaagaagc agatcgatta cgcattgggt   1080
gatggaggtc gcagctacgt cgtaggattt ggtactaacc acccgtacg ccctcaccac    1140
agatccagct cgtgccctga cgcaccagcc gtatgtgact ggaacacgta caacagcgcc  1200
ggccccaatg cccacgtact caccggagcc ttggtgggtg gtccagatag caacgatagc  1260
tacacggacg ctcgcagcga ttacatctcc aacgaagtgg ccacagatta caacgctggc  1320
ttccaatcag ctgtcgctgg tctcctcaag gctggcgtgt aaccgcacac agcactcaat  1380
gtctccctgt ccactggaca tgtgtacaat ttgacaacga aatgtaata ttcttcagaa   1440
aagtgcaata aaagttcaca attcaacaca aaaaaaaaaa aaaaaaaa                1489
```

<210> SEQ ID NO 39
<211> LENGTH: 458

<212> TYPE: PRT
<213> ORGANISM: Artificial sequence
<220> FEATURE:
<223> OTHER INFORMATION: Recombinant GHF9 Cell-1 cellulase

<400> SEQUENCE: 39

```
Met Lys Ile Leu Leu Ala Ile Ala Leu Met Leu Ser Thr Val Met Trp
1               5                   10                  15

Val Ser Thr Ala Ala Tyr Asp Tyr Lys Thr Val Leu Ser Asn Ser Leu
            20                  25                  30

Leu Phe Tyr Glu Ala Gln Arg Ser Gly Lys Leu Pro Ser Asp Gln Lys
        35                  40                  45

Val Thr Trp Arg Lys Asp Ser Ala Leu Asn Asp Lys Gly Gln Lys Gly
    50                  55                  60

Glu Asp Leu Thr Gly Gly Tyr Tyr Asp Ala Gly Asp Phe Val Lys Phe
65                  70                  75                  80

Gly Phe Pro Met Ala Tyr Thr Val Thr Val Leu Ala Trp Gly Val Ile
                85                  90                  95

Asp Tyr Glu Ser Ala Tyr Ser Ala Ala Gly Ala Leu Asp Ser Gly Arg
            100                 105                 110

Lys Ala Leu Lys Tyr Gly Thr Asp Tyr Phe Leu Lys Ala His Thr Ala
        115                 120                 125

Ala Asn Glu Phe Tyr Gly Gln Val Gly Gln Gly Asp Val Asp His Ala
    130                 135                 140

Tyr Trp Gly Arg Pro Glu Asp Met Thr Met Ser Arg Pro Ala Tyr Lys
145                 150                 155                 160

Ile Asp Thr Ser Lys Pro Gly Ser Asp Leu Ala Ala Glu Thr Ala Ala
                165                 170                 175

Ala Leu Ala Ala Thr Ala Ile Ala Tyr Lys Ser Ala Asp Ala Thr Tyr
            180                 185                 190

Ser Asn Asn Leu Ile Thr His Ala Lys Gln Leu Phe Asp Phe Ala Asn
        195                 200                 205

Asn Tyr Arg Gly Lys Tyr Ser Asp Ser Ile Thr Asp Ala Lys Asn Phe
    210                 215                 220

Tyr Ala Ser Gly Asp Tyr Lys Asp Glu Leu Val Trp Ala Ala Ala Trp
225                 230                 235                 240

Leu Tyr Arg Ala Thr Asn Asp Asn Thr Tyr Leu Thr Lys Ala Glu Ser
                245                 250                 255

Leu Tyr Asn Glu Phe Gly Leu Gly Asn Trp Asn Gly Ala Phe Asn Trp
            260                 265                 270

Asp Asn Lys Ile Ser Gly Val Gln Val Leu Leu Ala Lys Leu Thr Ser
        275                 280                 285

Lys Gln Ala Tyr Lys Asp Lys Val Gln Gly Tyr Val Asp Tyr Leu Ile
    290                 295                 300

Ser Ser Gln Lys Lys Thr Pro Lys Gly Leu Val Tyr Ile Asp Gln Trp
305                 310                 315                 320

Gly Thr Leu Arg His Ala Ala Asn Ser Ala Leu Ile Ala Leu Gln Ala
                325                 330                 335

Ala Asp Leu Gly Ile Asn Ala Ala Thr Tyr Arg Ala Tyr Ala Lys Lys
            340                 345                 350

Gln Ile Asp Tyr Ala Leu Gly Asp Gly Gly Arg Ser Tyr Val Val Gly
        355                 360                 365

Phe Gly Thr Asn Pro Pro Val Arg Pro His His Arg Ser Ser Ser Cys
    370                 375                 380
```

```
Pro Asp Ala Pro Ala Val Cys Asp Trp Asn Thr Tyr Asn Ser Ala Gly
385                 390                 395                 400

Pro Asn Ala His Val Leu Thr Gly Ala Leu Val Gly Gly Pro Asp Ser
            405                 410                 415

Asn Asp Ser Tyr Thr Asp Ala Arg Ser Asp Tyr Ile Ser Asn Glu Val
            420                 425                 430

Ala Thr Asp Tyr Asn Ala Gly Phe Gln Ser Val Ala Gly Leu Leu
            435                 440                 445

Lys Ala Gly Val His His His His His His
450                 455
```

<210> SEQ ID NO 40
<211> LENGTH: 438
<212> TYPE: PRT
<213> ORGANISM: Artificial sequence
<220> FEATURE:
<223> OTHER INFORMATION: Mature GHF9 Cell-1 cellulase

<400> SEQUENCE: 40

```
Ala Tyr Asp Tyr Lys Thr Val Leu Ser Asn Ser Leu Leu Phe Tyr Glu
1               5                   10                  15

Ala Gln Arg Ser Gly Lys Leu Pro Ser Asp Lys Val Thr Trp Arg
            20                  25                  30

Lys Asp Ser Ala Leu Asn Asp Lys Gly Gln Lys Gly Glu Asp Leu Thr
            35                  40                  45

Gly Gly Tyr Tyr Asp Ala Gly Asp Phe Val Lys Phe Gly Phe Pro Met
    50                  55                  60

Ala Tyr Thr Val Thr Val Leu Ala Trp Gly Val Ile Asp Tyr Glu Ser
65                  70                  75                  80

Ala Tyr Ser Ala Ala Gly Ala Leu Asp Ser Gly Arg Lys Ala Leu Lys
                85                  90                  95

Tyr Gly Thr Asp Tyr Phe Leu Lys Ala His Thr Ala Ala Asn Glu Phe
            100                 105                 110

Tyr Gly Gln Val Gly Gln Gly Asp Val Asp His Ala Tyr Trp Gly Arg
        115                 120                 125

Pro Glu Asp Met Thr Met Ser Arg Pro Ala Tyr Lys Ile Asp Thr Ser
    130                 135                 140

Lys Pro Gly Ser Asp Leu Ala Ala Glu Thr Ala Ala Ala Leu Ala Ala
145                 150                 155                 160

Thr Ala Ile Ala Tyr Lys Ser Ala Asp Ala Thr Tyr Ser Asn Asn Leu
                165                 170                 175

Ile Thr His Ala Lys Gln Leu Phe Asp Phe Ala Asn Asn Tyr Arg Gly
            180                 185                 190

Lys Tyr Ser Asp Ser Ile Thr Asp Ala Lys Asn Phe Tyr Ala Ser Gly
        195                 200                 205

Asp Tyr Lys Asp Glu Leu Val Trp Ala Ala Ala Trp Leu Tyr Arg Ala
    210                 215                 220

Thr Asn Asp Asn Thr Tyr Leu Thr Lys Ala Glu Ser Leu Tyr Asn Glu
225                 230                 235                 240

Phe Gly Leu Gly Asn Trp Asn Gly Ala Phe Asn Trp Asp Asn Lys Ile
                245                 250                 255

Ser Gly Val Gln Val Leu Leu Ala Lys Leu Thr Ser Lys Gln Ala Tyr
            260                 265                 270

Lys Asp Lys Val Gln Gly Tyr Val Asp Tyr Leu Ile Ser Ser Gln Lys
        275                 280                 285
```

```
Lys Thr Pro Lys Gly Leu Val Tyr Ile Asp Gln Trp Gly Thr Leu Arg
    290                 295                 300

His Ala Ala Asn Ser Ala Leu Ile Ala Leu Gln Ala Ala Asp Leu Gly
305                 310                 315                 320

Ile Asn Ala Ala Thr Tyr Arg Ala Tyr Ala Lys Lys Gln Ile Asp Tyr
                325                 330                 335

Ala Leu Gly Asp Gly Arg Ser Tyr Val Val Gly Phe Gly Thr Asn
                340                 345                 350

Pro Pro Val Arg Pro His His Arg Ser Ser Cys Pro Asp Ala Pro
            355                 360                 365

Ala Val Cys Asp Trp Asn Thr Tyr Asn Ser Ala Gly Pro Asn Ala His
370                 375                 380

Val Leu Thr Gly Ala Leu Val Gly Gly Pro Asp Ser Asn Asp Ser Tyr
385                 390                 395                 400

Thr Asp Ala Arg Ser Asp Tyr Ile Ser Asn Glu Val Ala Thr Asp Tyr
                405                 410                 415

Asn Ala Gly Phe Gln Ser Ala Val Ala Gly Leu Leu Lys Ala Gly Val
                420                 425                 430

His His His His His His
        435

<210> SEQ ID NO 41
<211> LENGTH: 1683
<212> TYPE: DNA
<213> ORGANISM: Artificial sequence
<220> FEATURE:
<223> OTHER INFORMATION: Beta-glu cellulase cDNA

<400> SEQUENCE: 41
gattctgaca tcctcacgtc tagggcgctt gacagagcaa cgagatgagg ttacagacgg      60
tttgcttcgt catctttgtg acggcagtat tcggggctga cgtcgataac gaaaccctct     120
tcacgtttcc tgaagacttt aagttaggcg ccgctacggc ttcataccag attgaaggag     180
gatggaatgc ggatggaaag ggtgtcaata tttgggacac actgacacat gagcgctcac     240
aattagtggt tgataaatca agcggtgacg tggctgacga ctcgtatcat ctttataagg     300
aggacgtgaa gcttctgaag aacatggggg cacaacttta tcgcttctct atatcttggg     360
ctcgcatcct gcctgaagga catgataata aggtgaacca ggcgggcatt gagtactaca     420
acaagctcat agacgaactt ctagacaatg aatagagcc gatggttact atgtatcact     480
gggatctacc ccagacactc caagacctgg gaggatggcc aaatagagaa ttggcaaaat     540
actccgagaa ttacgcccgc gttttatttc aaaactttgg agaccgggtt aaattgtggc     600
tcacattcaa tgagcctctg actttcatgg atgcatatgc atctgagaca ggaatggctc     660
catcaattga cacacccggt atcggcgatt accttgcggc acacactgtg atccttgccc     720
atgccaatat ctaccgtatg tatgagaggg aattcaaaga ggaacagaaa ggaaaggttg     780
gtatcgcact caacatacac tggtgtgagc cggtgactaa ttcgacaaag acgttgagg     840 cttgtgaaag gtatcaacag ttcaacctgg gaatatacgc tcatcccatc ttctctgtag     900
agggcgatta ccccagtgtt ttgaaagcga gggtagacgc aaacagcgta acggaaggtt     960
acaccacatc tcgtctacct aaattcacta cagaggaagt agatttcatc agaggaacac    1020
atgatttctt gggtctgaat ttctacactg ctgtaacggg agcggatgga gttgaagggg    1080
aacccccgtc gcgtacagag acatggggcg cgatcacatc acaggatccg gactggcccg    1140
agtctgcttc ttcatggctc agagttgtac catgggggatt ccgcaaggaa cttaactgga    1200
```

```
tcgcgaacga atacggtaac cctcctatat acatcactga aaatggcttc tccgactacg    1260
gtggcctcaa tgatacagac agagtgctgt actacactga acatttaaag gagatgctga    1320
aggcaattca catagatgaa gttaacgtag tcggatacac agcctggagc ctagtagaca    1380
atttcgaatg gctgcgagga tatactgaga ggttcggtat acatgaagtg aatttcaacg    1440
acccaagtcg cccacgagtt cccaaggagt cagcaaaggt gctcacagag atcttcaaca    1500
caaggaggat tccagaacgc ttcctagact aacttcatat tcaagacgca aagacttata    1560
tcaaaaatta atttaaaaga gggcttactg ctgactgtaa gttccctcaa aacagcaata    1620
aggtttatga tcatggaaaa cacttcgaat taaataaact tatatacaaa aaaaaaaaaa    1680
aaa                                                                  1683
```

<210> SEQ ID NO 42
<211> LENGTH: 501
<212> TYPE: PRT
<213> ORGANISM: Artificial sequence
<220> FEATURE:
<223> OTHER INFORMATION: Recombinant Beta-glu cellulase

<400> SEQUENCE: 42

```
Met Arg Leu Gln Thr Val Cys Phe Val Ile Phe Val Thr Ala Val Phe
1               5                   10                  15

Gly Ala Asp Val Asp Asn Glu Thr Leu Phe Thr Phe Pro Glu Asp Phe
            20                  25                  30

Lys Leu Gly Ala Ala Thr Ala Ser Tyr Gln Ile Glu Gly Gly Trp Asn
        35                  40                  45

Ala Asp Gly Lys Gly Val Asn Ile Trp Asp Thr Leu Thr His Glu Arg
    50                  55                  60

Ser Gln Leu Val Val Asp Lys Ser Ser Gly Asp Val Ala Asp Asp Ser
65                  70                  75                  80

Tyr His Leu Tyr Lys Glu Asp Val Lys Leu Leu Lys Asn Met Gly Ala
                85                  90                  95

Gln Leu Tyr Arg Phe Ser Ile Ser Trp Ala Arg Ile Leu Pro Glu Gly
            100                 105                 110

His Asp Asn Lys Val Asn Gln Ala Gly Ile Glu Tyr Tyr Asn Lys Leu
        115                 120                 125

Ile Asp Glu Leu Leu Asp Asn Gly Ile Glu Pro Met Val Thr Met Tyr
    130                 135                 140

His Trp Asp Leu Pro Gln Thr Leu Gln Asp Leu Gly Gly Trp Pro Asn
145                 150                 155                 160

Arg Glu Leu Ala Lys Tyr Ser Glu Asn Tyr Ala Arg Val Leu Phe Gln
                165                 170                 175

Asn Phe Gly Asp Arg Val Lys Leu Trp Leu Thr Phe Asn Glu Pro Leu
            180                 185                 190

Thr Phe Met Asp Ala Tyr Ala Ser Glu Thr Gly Met Ala Pro Ser Ile
        195                 200                 205

Asp Thr Pro Gly Ile Gly Asp Tyr Leu Ala Ala His Thr Val Ile Leu
    210                 215                 220

Ala His Ala Asn Ile Tyr Arg Met Tyr Glu Arg Glu Phe Lys Glu Glu
225                 230                 235                 240

Gln Lys Gly Lys Val Gly Ile Ala Leu Asn Ile His Trp Cys Glu Pro
                245                 250                 255

Val Thr Asn Ser Thr Lys Asp Val Glu Ala Cys Glu Arg Tyr Gln Gln
            260                 265                 270
```

```
Phe Asn Leu Gly Ile Tyr Ala His Pro Ile Phe Ser Val Glu Gly Asp
            275                 280                 285

Tyr Pro Ser Val Leu Lys Ala Arg Val Asp Ala Asn Ser Val Thr Glu
        290                 295                 300

Gly Tyr Thr Thr Ser Arg Leu Pro Lys Phe Thr Glu Glu Val Asp
305                 310                 315                 320

Phe Ile Arg Gly Thr His Asp Phe Leu Gly Leu Asn Phe Tyr Thr Ala
                325                 330                 335

Val Thr Gly Ala Asp Gly Val Glu Gly Pro Pro Ser Arg Tyr Arg
            340                 345                 350

Asp Met Gly Ala Ile Thr Ser Gln Asp Pro Asp Trp Pro Glu Ser Ala
            355                 360                 365

Ser Ser Trp Leu Arg Val Val Pro Trp Gly Phe Arg Lys Glu Leu Asn
370                 375                 380

Trp Ile Ala Asn Glu Tyr Gly Asn Pro Pro Ile Tyr Ile Thr Glu Asn
385                 390                 395                 400

Gly Phe Ser Asp Tyr Gly Leu Asn Asp Thr Asp Arg Val Leu Tyr
                405                 410                 415

Tyr Thr Glu His Leu Lys Glu Met Leu Lys Ala Ile His Ile Asp Glu
            420                 425                 430

Val Asn Val Gly Tyr Thr Ala Trp Ser Leu Val Asp Asn Phe Glu
            435                 440                 445

Trp Leu Arg Gly Tyr Thr Glu Arg Phe Gly Ile His Glu Val Asn Phe
        450                 455                 460

Asn Asp Pro Ser Arg Pro Arg Val Pro Lys Glu Ser Ala Lys Val Leu
465                 470                 475                 480

Thr Glu Ile Phe Asn Thr Arg Arg Ile Pro Glu Arg Phe Leu Asp His
                485                 490                 495

His His His His His
            500

<210> SEQ ID NO 43
<211> LENGTH: 484
<212> TYPE: PRT
<213> ORGANISM: Artificial sequence
<220> FEATURE:
<223> OTHER INFORMATION: Mature Beta-glu cellulase

<400> SEQUENCE: 43

Ala Asp Val Asp Asn Glu Thr Leu Phe Thr Phe Pro Glu Asp Phe Lys
1               5                   10                  15

Leu Gly Ala Ala Thr Ala Ser Tyr Gln Ile Glu Gly Gly Trp Asn Ala
            20                  25                  30

Asp Gly Lys Gly Val Asn Ile Trp Asp Thr Leu Thr His Glu Arg Ser
        35                  40                  45

Gln Leu Val Val Asp Lys Ser Ser Gly Asp Val Ala Asp Ser Tyr
    50                  55                  60

His Leu Tyr Lys Glu Asp Val Lys Leu Leu Lys Asn Met Gly Ala Gln
65                  70                  75                  80

Leu Tyr Arg Phe Ser Ile Ser Trp Ala Arg Ile Leu Pro Glu Gly His
                85                  90                  95

Asp Asn Lys Val Asn Gln Ala Gly Ile Glu Tyr Tyr Asn Lys Leu Ile
            100                 105                 110

Asp Glu Leu Leu Asp Asn Gly Ile Glu Pro Met Val Thr Met Tyr His
        115                 120                 125
```

Trp Asp Leu Pro Gln Thr Leu Gln Asp Leu Gly Gly Trp Pro Asn Arg
130                 135                 140

Glu Leu Ala Lys Tyr Ser Glu Asn Tyr Ala Arg Val Leu Phe Gln Asn
145                 150                 155                 160

Phe Gly Asp Arg Val Lys Leu Trp Leu Thr Phe Asn Glu Pro Leu Thr
                165                 170                 175

Phe Met Asp Ala Tyr Ala Ser Glu Thr Gly Met Ala Pro Ser Ile Asp
                180                 185                 190

Thr Pro Gly Ile Gly Asp Tyr Leu Ala Ala His Thr Val Ile Leu Ala
                195                 200                 205

His Ala Asn Ile Tyr Arg Met Tyr Glu Arg Glu Phe Lys Glu Glu Gln
210                 215                 220

Lys Gly Lys Val Gly Ile Ala Leu Asn Ile His Trp Cys Glu Pro Val
225                 230                 235                 240

Thr Asn Ser Thr Lys Asp Val Glu Ala Cys Glu Arg Tyr Gln Gln Phe
                245                 250                 255

Asn Leu Gly Ile Tyr Ala His Pro Ile Phe Ser Val Glu Gly Asp Tyr
                260                 265                 270

Pro Ser Val Leu Lys Ala Arg Val Asp Ala Asn Ser Val Thr Glu Gly
                275                 280                 285

Tyr Thr Thr Ser Arg Leu Pro Lys Phe Thr Thr Glu Glu Val Asp Phe
290                 295                 300

Ile Arg Gly Thr His Asp Phe Leu Gly Leu Asn Phe Tyr Thr Ala Val
305                 310                 315                 320

Thr Gly Ala Asp Gly Val Glu Gly Glu Pro Pro Ser Arg Tyr Arg Asp
                325                 330                 335

Met Gly Ala Ile Thr Ser Gln Asp Pro Asp Trp Pro Glu Ser Ala Ser
                340                 345                 350

Ser Trp Leu Arg Val Val Pro Trp Gly Phe Arg Lys Glu Leu Asn Trp
                355                 360                 365

Ile Ala Asn Glu Tyr Gly Asn Pro Pro Ile Tyr Ile Thr Glu Asn Gly
370                 375                 380

Phe Ser Asp Tyr Gly Gly Leu Asn Asp Thr Asp Arg Val Leu Tyr Tyr
385                 390                 395                 400

Thr Glu His Leu Lys Glu Met Leu Lys Ala Ile His Ile Asp Glu Val
                405                 410                 415

Asn Val Val Gly Tyr Thr Ala Trp Ser Leu Val Asp Asn Phe Glu Trp
                420                 425                 430

Leu Arg Gly Tyr Thr Glu Arg Phe Gly Ile His Glu Val Asn Phe Asn
                435                 440                 445

Asp Pro Ser Arg Pro Arg Val Pro Lys Glu Ser Ala Lys Val Leu Thr
450                 455                 460

Glu Ile Phe Asn Thr Arg Arg Ile Pro Glu Arg Phe Leu Asp His His
465                 470                 475                 480

His His His His

<210> SEQ ID NO 44
<211> LENGTH: 1088
<212> TYPE: DNA
<213> ORGANISM: Artificial sequence
<220> FEATURE:
<223> OTHER INFORMATION: GHF7-3 cDNA

<400> SEQUENCE: 44

```
atgtttgctt tgattgtttt tgccattcag ctgctgcatg cacagggaaa tcaggatttc      60
acctacacga ttaatggtac taaagttact gggcaaatag tgattgatca agagtggaga     120
ggcaacaata ccccaactgc aactgtgaat ctttctagtt ttggtgtaac tgtgaatgga     180
gataacgtgt cacagagatt caagacagga actgctgtgg ggtcccgtat ctatattctt     240
gctccagggg gaaaagcgta tgagaagttc aagttggtga actctgagct gacgtttgat     300
gttgatatta gccagattcc atgcggaatg aatgctgcca tttacactgc cgaattgcct     360
gcagacggtg taacacctgg tcacgaagct ggagcagcgt atggtggcgg atactgtgat     420
gcaaactatg ttggaggagt tggatgtgca gaatttgata ttggtgaaag caatgcacgt     480
gcaacagttt atacaagtca tggatgcagc ccgacgactg gctttgcaaa cagggcagc     540
attagctgtg acacaggtgg aactggagcc aacccgtacc gtgtggacaa gaacttctat     600
ggcaatggtt catcattcac tgtcaatact gcacagaaat tcactgtggt gacgcaattc     660
aaaggaaacc cactgacttc gattgatcgt atctacatcc aaggtaataa acaaacaaaa     720
cagccgaaca acattaataa caacttggat cgtatcagcc atcgcttgc ggcaggacat     780
gttctgatat tctcgatctg ggcttcggat ggagatatgt cttggatgga ctgcaatgac     840
aacggacctt gcaatgcagg ccaggaaagt tcacgttatt gggaacaaa actatccgat     900
gctactgtta cctacagcaa tgttaggtgg ggtccgattg atagcactta ttagataaag     960
aagttgaaga ccgagagggt cttttggtgg aaaaaaaaat ttttttttgtt tattgaagtg    1020
aagcaatctt atttttttttg tagtaatttt ttttgtgga taaaataaaa attgagataa    1080
agatgcaa                                                             1088
```

<210> SEQ ID NO 45
<211> LENGTH: 317
<212> TYPE: PRT
<213> ORGANISM: Artificial sequence
<220> FEATURE:
<223> OTHER INFORMATION: GHF7-3 protein

<400> SEQUENCE: 45

```
Met Phe Ala Leu Ile Val Phe Ala Ile Gln Leu Leu His Ala Gln Gly
1               5                   10                  15

Asn Gln Asp Phe Thr Tyr Thr Ile Asn Gly Thr Lys Val Thr Gly Gln
            20                  25                  30

Ile Val Ile Asp Gln Glu Trp Arg Gly Asn Asn Thr Pro Thr Ala Thr
        35                  40                  45

Val Asn Leu Ser Ser Phe Gly Val Thr Val Asn Gly Asp Asn Val Ser
    50                  55                  60

Gln Arg Phe Lys Thr Gly Thr Ala Val Gly Ser Arg Ile Tyr Ile Leu
65                  70                  75                  80

Ala Pro Gly Gly Lys Ala Tyr Glu Lys Phe Lys Leu Val Asn Ser Glu
                85                  90                  95

Leu Thr Phe Asp Val Asp Ile Ser Gln Ile Pro Cys Gly Met Asn Ala
            100                 105                 110

Ala Ile Tyr Thr Ala Glu Leu Pro Ala Asp Gly Val Thr Pro Gly His
        115                 120                 125

Glu Ala Gly Ala Ala Tyr Gly Gly Gly Tyr Cys Asp Ala Asn Tyr Val
    130                 135                 140

Gly Gly Val Gly Cys Ala Glu Phe Asp Ile Gly Glu Ser Asn Ala Arg
145                 150                 155                 160

Ala Thr Val Tyr Thr Ser His Gly Cys Ser Pro Thr Thr Gly Phe Ala
```

```
                165                 170                 175
Lys Gln Gly Ser Ile Ser Cys Asp Thr Gly Thr Gly Ala Asn Pro
            180                 185                 190

Tyr Arg Val Asp Lys Asn Phe Tyr Gly Asn Gly Ser Ser Phe Thr Val
        195                 200                 205

Asn Thr Ala Gln Lys Phe Thr Val Val Thr Gln Phe Lys Gly Asn Pro
    210                 215                 220

Leu Thr Ser Ile Asp Arg Ile Tyr Ile Gln Gly Asn Lys Gln Thr Lys
225                 230                 235                 240

Gln Pro Asn Asn Ile Asn Asn Asn Leu Asp Arg Ile Ser Pro Ser Leu
                245                 250                 255

Ala Ala Gly His Val Leu Ile Phe Ser Ile Trp Ala Ser Asp Gly Asp
            260                 265                 270

Met Ser Trp Met Asp Cys Asn Asp Asn Gly Pro Cys Asn Ala Gly Gln
        275                 280                 285

Glu Ser Ser Arg Tyr Leu Gly Thr Lys Leu Ser Asp Ala Thr Val Thr
    290                 295                 300

Tyr Ser Asn Val Arg Trp Gly Pro Ile Asp Ser Thr Tyr
305                 310                 315

<210> SEQ ID NO 46
<211> LENGTH: 31
<212> TYPE: DNA
<213> ORGANISM: Artificial sequence
<220> FEATURE:
<223> OTHER INFORMATION: GHF7-3 forward primer

<400> SEQUENCE: 46
gatcagatct taatcaggat ttcacctaca c                              31

<210> SEQ ID NO 47
<211> LENGTH: 30
<212> TYPE: DNA
<213> ORGANISM: Artificial sequence
<220> FEATURE:
<223> OTHER INFORMATION: GHF7-3 reverse primer

<400> SEQUENCE: 47
gatcggtacc ataagtgcta tcaatcggac                                30

<210> SEQ ID NO 48
<211> LENGTH: 337
<212> TYPE: PRT
<213> ORGANISM: Artificial sequence
<220> FEATURE:
<223> OTHER INFORMATION: GHF7-3 protein with thrombin-cleavable (His)6
      terminus

<400> SEQUENCE: 48

Met Val Ser Ala Ile Val Leu Tyr Val Leu Leu Ala Ala Ala His
1               5                   10                  15

Ser Ala Phe Ala Asp Leu Asn Gln Asp Phe Thr Tyr Thr Ile Asn Gly
            20                  25                  30

Thr Lys Val Thr Gly Gln Ile Val Ile Asp Gln Glu Trp Arg Gly Asn
        35                  40                  45

Asn Thr Pro Thr Ala Thr Val Asn Leu Ser Ser Phe Gly Val Thr Val
    50                  55                  60

Asn Gly Asp Asn Val Ser Gln Arg Phe Lys Thr Gly Thr Ala Val Gly
65                  70                  75                  80
```

```
Ser Arg Ile Tyr Ile Leu Ala Pro Gly Gly Lys Ala Tyr Glu Lys Phe
            85                  90                  95

Lys Leu Val Asn Ser Glu Leu Thr Phe Asp Val Asp Ile Ser Gln Ile
            100                 105                 110

Pro Cys Gly Met Asn Ala Ala Ile Tyr Thr Ala Glu Leu Pro Ala Asp
            115                 120                 125

Gly Val Thr Pro Gly His Glu Ala Gly Ala Tyr Gly Gly Tyr
            130                 135                 140

Cys Asp Ala Asn Tyr Val Gly Gly Val Gly Cys Ala Glu Phe Asp Ile
145                 150                 155                 160

Gly Glu Ser Asn Ala Arg Ala Thr Val Tyr Thr Ser His Gly Cys Ser
                165                 170                 175

Pro Thr Thr Gly Phe Ala Lys Gln Gly Ser Ile Ser Cys Asp Thr Gly
            180                 185                 190

Gly Thr Gly Ala Asn Pro Tyr Arg Val Asp Lys Asn Phe Tyr Gly Asn
            195                 200                 205

Gly Ser Ser Phe Thr Val Asn Thr Ala Gln Lys Phe Thr Val Val Thr
            210                 215                 220

Gln Phe Lys Gly Asn Pro Leu Thr Ser Ile Asp Arg Ile Tyr Ile Gln
225                 230                 235                 240

Gly Asn Lys Gln Thr Lys Gln Pro Asn Asn Ile Asn Asn Asn Leu Asp
            245                 250                 255

Arg Ile Ser Pro Ser Leu Ala Ala Gly His Val Leu Ile Phe Ser Ile
            260                 265                 270

Trp Ala Ser Asp Gly Asp Met Ser Trp Met Asp Cys Asn Asp Asn Gly
            275                 280                 285

Pro Cys Asn Ala Gly Gln Glu Ser Ser Arg Tyr Leu Gly Thr Lys Leu
            290                 295                 300

Ser Asp Ala Thr Val Thr Tyr Ser Asn Val Arg Trp Gly Pro Ile Asp
305                 310                 315                 320

Ser Thr Tyr Gly Thr Leu Val Pro Arg Gly Ser His His His His
            325                 330                 335

His

<210> SEQ ID NO 49
<211> LENGTH: 14
<212> TYPE: PRT
<213> ORGANISM: Artificial sequence
<220> FEATURE:
<223> OTHER INFORMATION: Thrombin-cleavable (His)6 terminus

<400> SEQUENCE: 49

Gly Thr Leu Val Pro Arg Gly Ser His His His His His His
1               5                   10

<210> SEQ ID NO 50
<211> LENGTH: 317
<212> TYPE: PRT
<213> ORGANISM: Artificial sequence
<220> FEATURE:
<223> OTHER INFORMATION: Mature GHF7-3

<400> SEQUENCE: 50

Asp Leu Asn Gln Asp Phe Thr Tyr Thr Ile Asn Gly Thr Lys Val Thr
1               5                   10                  15

Gly Gln Ile Val Ile Asp Gln Glu Trp Arg Gly Asn Asn Thr Pro Thr
            20                  25                  30
```

```
Ala Thr Val Asn Leu Ser Ser Phe Gly Val Thr Val Asn Gly Asp Asn
             35                  40                  45

Val Ser Gln Arg Phe Lys Thr Gly Thr Ala Val Gly Ser Arg Ile Tyr
 50                  55                  60

Ile Leu Ala Pro Gly Gly Lys Ala Tyr Glu Lys Phe Lys Leu Val Asn
 65                  70                  75                  80

Ser Glu Leu Thr Phe Asp Val Asp Ile Ser Gln Ile Pro Cys Gly Met
                 85                  90                  95

Asn Ala Ala Ile Tyr Thr Ala Glu Leu Pro Ala Asp Gly Val Thr Pro
            100                 105                 110

Gly His Glu Ala Gly Ala Ala Tyr Gly Gly Gly Tyr Cys Asp Ala Asn
            115                 120                 125

Tyr Val Gly Gly Val Gly Cys Ala Glu Phe Asp Ile Gly Glu Ser Asn
130                 135                 140

Ala Arg Ala Thr Val Tyr Thr Ser His Gly Cys Ser Pro Thr Thr Gly
145                 150                 155                 160

Phe Ala Lys Gln Gly Ser Ile Ser Cys Asp Thr Gly Thr Gly Thr Ala
                165                 170                 175

Asn Pro Tyr Arg Val Asp Lys Asn Phe Tyr Gly Asn Gly Ser Ser Phe
            180                 185                 190

Thr Val Asn Thr Ala Gln Lys Phe Thr Val Val Thr Gln Phe Lys Gly
            195                 200                 205

Asn Pro Leu Thr Ser Ile Asp Arg Ile Tyr Ile Gln Gly Asn Lys Gln
            210                 215                 220

Thr Lys Gln Pro Asn Asn Ile Asn Asn Asn Leu Asp Arg Ile Ser Pro
225                 230                 235                 240

Ser Leu Ala Ala Gly His Val Leu Ile Phe Ser Ile Trp Ala Ser Asp
                245                 250                 255

Gly Asp Met Ser Trp Met Asp Cys Asn Asp Asn Gly Pro Cys Asn Ala
            260                 265                 270

Gly Gln Glu Ser Ser Arg Tyr Leu Gly Thr Lys Leu Ser Asp Ala Thr
            275                 280                 285

Val Thr Tyr Ser Asn Val Arg Trp Gly Pro Ile Asp Ser Thr Tyr Gly
            290                 295                 300

Thr Leu Val Pro Arg Gly Ser His His His His His His
305                 310                 315

<210> SEQ ID NO 51
<211> LENGTH: 655
<212> TYPE: PRT
<213> ORGANISM: Artificial sequence
<220> FEATURE:
<223> OTHER INFORMATION: Recombinant Laccase 6

<400> SEQUENCE: 51

Met Leu Pro Cys Val Leu Leu Ala Cys Ala Ile Gly Val Ala Ser Ala
 1                5                  10                  15

Thr Ser Val Leu Leu Asn Ser Tyr Leu Gln Pro Asn Asp Asp Ile Asp
             20                  25                  30

Arg Asn Thr Tyr Leu Leu Asn Ala Lys Ser Asn Asn Cys Ala Arg Ile
             35                  40                  45

Cys Asn Gly Thr Glu Ala Pro Lys Ile Cys Tyr Tyr Gln Trp Thr Ile
         50                  55                  60

Glu Asn Tyr Val Thr Leu Ser Glu Ala Cys Asp Asn Cys Pro Leu Asn
 65                  70                  75                  80
```

```
Val Thr Ala Cys Tyr Asn Ala Gln Cys Ile Thr Ala Asp Gly Tyr Glu
            85                  90                  95

Arg Ser Ile Leu Ser Val Asn Arg Lys Leu Pro Gly Pro Ser Ile Glu
        100                 105                 110

Val Cys Leu Arg Asp Arg Val Ile Val Asp Ile Thr Asn Asn Met Ala
        115                 120                 125

Gly Arg Thr Thr Ser Ile His Trp His Gly Val Phe Gln Lys Gly Ser
        130                 135                 140

Gln Tyr Met Asp Gly Val Pro Met Val Thr Gln Cys Thr Ile His Glu
145                 150                 155                 160

Gly Asp Thr Phe Arg Tyr Asp Phe Ile Ala Asn Asn Glu Gly Thr His
                165                 170                 175

Phe Trp His Ser His Asp Gly Leu Gln Lys Leu Asp Gly Val Thr Gly
                180                 185                 190

Asn Leu Val Val Arg Val Pro Lys Asn Phe Asp Pro Asn Gly Gln Leu
        195                 200                 205

Tyr Asp Phe Asp Leu Pro Glu His Lys Ile Phe Ile Ser Asp Trp Leu
        210                 215                 220

His Leu Ser Ala Asp Asp His Phe Pro Gly Leu Arg Ala Thr Asn Pro
225                 230                 235                 240

Gly Gln Asp Ala Asn Ser Phe Leu Ile Asn Gly Arg Gly Arg Thr Leu
                245                 250                 255

Ile Gly Thr Gln Ser Thr Asn Thr Pro Tyr Ala Gln Ile Asn Val Gln
                260                 265                 270

Trp Gly Arg Arg Tyr Arg Leu Arg Ile Val Gly Ser Leu Cys Thr Val
        275                 280                 285

Cys Pro Thr Gln Leu Thr Ile Asp Gly His Lys Ile Thr Val Ile Ala
290                 295                 300

Thr Asp Gly Asn Ser Val Ala Pro Ala Arg Val Asp Ser Leu Ile Ile
305                 310                 315                 320

Tyr Ser Gly Glu Arg Tyr Asp Val Val Leu Glu Ala Thr Asn Thr Glu
                325                 330                 335

Gly Ser Tyr Trp Ile His Leu Lys Gly Leu Ala Thr Cys Val Gly Ser
                340                 345                 350

Arg Val Tyr Gln Leu Gly Val Leu Gln Tyr Glu Asn Thr Thr Thr Asn
        355                 360                 365

Lys Leu His Ala Leu Thr Pro Asp Pro Gly Tyr Asp Gly Phe Pro Gln
        370                 375                 380

Pro Ala Ser Tyr Arg Val Leu Asn Pro Glu Asn Ala Ser Cys Ser Ile
385                 390                 395                 400

Gly Ser Thr Gly Leu Cys Val Thr Gln Leu Ala Asn Ser Asp Pro Val
                405                 410                 415

Pro Arg Asp Ile Leu Thr Gln Leu Pro Asp Ile Asn Tyr Leu Leu Gln
                420                 425                 430

Phe Gly Phe Glu Thr Phe Asp Ser Arg Ser Phe Lys Ala Tyr Asp
        435                 440                 445

Arg Tyr Phe Val Ser Pro Phe Leu Glu Leu Ser Ser Thr Val Asn
        450                 455                 460

Asn Ile Ser Phe Val Ser Pro Ser Pro Leu Leu Ser Gln Arg Gly
465                 470                 475                 480

Asp Val Pro Asp Asp Ile Leu Cys Pro Thr Gly Ala Asp Gly Leu Pro
                485                 490                 495

Gln Cys Pro Gly Gly Asn Ser Tyr Cys Thr Cys Val His Val Ile Lys
```

```
                500                 505                 510
Ile Lys Leu Gly Ala Leu Val Gln Ile Ile Leu Ser Asp Gln Ser Pro
            515                 520                 525

Lys Ser Asp Leu Asn His Pro Phe His Ile His Gly His Ala Phe Tyr
530                 535                 540

Val Leu Gly Met Gly Gln Tyr Ala Ala Gly Gln Thr Ala Gln Asp Leu
545                 550                 555                 560

Leu Asn Ser Leu Lys Ser Asn Val Ser Val Ser Pro Ala Pro Val
            565                 570                 575

Leu Lys Asp Thr Val Ala Val Pro Ser Gly Gly Tyr Ala Ile Ile Lys
            580                 585                 590

Phe Arg Pro Lys Asn Pro Gly Tyr Trp Phe Leu His Cys His Phe Leu
            595                 600                 605

Tyr His Val Ala Thr Gly Met Ser Val Val Leu Gln Val Gly Glu Thr
            610                 615                 620

Ser Asp Tyr Pro Pro Thr Pro Asp Gly Phe Pro Lys Cys Gly Ser Phe
625                 630                 635                 640

Thr Pro Pro Val Asn Thr Asn Gly Gly His His His His His His
            645                 650                 655

<210> SEQ ID NO 52
<211> LENGTH: 639
<212> TYPE: PRT
<213> ORGANISM: Artificial sequence
<220> FEATURE:
<223> OTHER INFORMATION: Mature Laccase 6

<400> SEQUENCE: 52

Thr Ser Val Leu Leu Asn Ser Tyr Leu Gln Pro Asn Asp Asp Ile Asp
1               5                   10                  15

Arg Asn Thr Tyr Leu Leu Asn Ala Lys Ser Asn Asn Cys Ala Arg Ile
            20                  25                  30

Cys Asn Gly Thr Glu Ala Pro Lys Ile Cys Tyr Tyr Gln Trp Thr Ile
        35                  40                  45

Glu Asn Tyr Val Thr Leu Ser Glu Ala Cys Asp Asn Cys Pro Leu Asn
    50                  55                  60

Val Thr Ala Cys Tyr Asn Ala Gln Cys Ile Thr Ala Asp Gly Tyr Glu
65                  70                  75                  80

Arg Ser Ile Leu Ser Val Asn Arg Lys Leu Pro Gly Pro Ser Ile Glu
                85                  90                  95

Val Cys Leu Arg Asp Arg Val Ile Val Asp Ile Thr Asn Asn Met Ala
            100                 105                 110

Gly Arg Thr Thr Ser Ile His Trp His Gly Val Phe Gln Lys Gly Ser
        115                 120                 125

Gln Tyr Met Asp Gly Val Pro Met Val Thr Gln Cys Thr Ile His Glu
    130                 135                 140

Gly Asp Thr Phe Arg Tyr Asp Phe Ile Ala Asn Asn Glu Gly Thr His
145                 150                 155                 160

Phe Trp His Ser His Asp Gly Leu Gln Lys Leu Asp Gly Val Thr Gly
                165                 170                 175

Asn Leu Val Val Arg Val Pro Lys Asn Phe Asp Pro Asn Gly Gln Leu
            180                 185                 190

Tyr Asp Phe Asp Leu Pro Glu His Lys Ile Phe Ile Ser Asp Trp Leu
        195                 200                 205

His Leu Ser Ala Asp Asp His Phe Pro Gly Leu Arg Ala Thr Asn Pro
```

```
                210               215                 220
Gly Gln Asp Ala Asn Ser Phe Leu Ile Asn Gly Arg Gly Arg Thr Leu
225                 230                 235                 240

Ile Gly Thr Gln Ser Thr Asn Thr Pro Tyr Ala Gln Ile Asn Val Gln
            245                 250                 255

Trp Gly Arg Arg Tyr Arg Leu Arg Ile Val Gly Ser Leu Cys Thr Val
                260                 265                 270

Cys Pro Thr Gln Leu Thr Ile Asp Gly His Lys Ile Thr Val Ile Ala
            275                 280                 285

Thr Asp Gly Asn Ser Val Ala Pro Ala Arg Val Asp Ser Leu Ile Ile
        290                 295                 300

Tyr Ser Gly Glu Arg Tyr Asp Val Val Leu Glu Ala Thr Asn Thr Glu
305                 310                 315                 320

Gly Ser Tyr Trp Ile His Leu Lys Gly Leu Ala Thr Cys Val Gly Ser
                325                 330                 335

Arg Val Tyr Gln Leu Gly Val Leu Gln Tyr Glu Asn Thr Thr Thr Asn
                340                 345                 350

Lys Leu His Ala Leu Thr Pro Asp Pro Gly Tyr Asp Gly Phe Pro Gln
            355                 360                 365

Pro Ala Ser Tyr Arg Val Leu Asn Pro Glu Asn Ala Ser Cys Ser Ile
370                 375                 380

Gly Ser Thr Gly Leu Cys Val Thr Gln Leu Ala Asn Ser Asp Pro Val
385                 390                 395                 400

Pro Arg Asp Ile Leu Thr Gln Leu Pro Asp Ile Asn Tyr Leu Leu Gln
                405                 410                 415

Phe Gly Phe Glu Thr Phe Asp Ser Arg Ser Phe Lys Ala Tyr Asp
                420                 425                 430

Arg Tyr Phe Val Ser Pro Phe Leu Glu Leu Leu Ser Ser Thr Val Asn
            435                 440                 445

Asn Ile Ser Phe Val Ser Pro Pro Ser Pro Leu Leu Ser Gln Arg Gly
        450                 455                 460

Asp Val Pro Asp Asp Ile Leu Cys Pro Thr Gly Ala Asp Gly Leu Pro
465                 470                 475                 480

Gln Cys Pro Gly Gly Asn Ser Tyr Cys Thr Cys Val His Val Ile Lys
                485                 490                 495

Ile Lys Leu Gly Ala Leu Val Gln Ile Ile Leu Ser Asp Gln Ser Pro
                500                 505                 510

Lys Ser Asp Leu Asn His Pro Phe His Ile His Gly His Ala Phe Tyr
            515                 520                 525

Val Leu Gly Met Gly Gln Tyr Ala Ala Gly Gln Thr Ala Gln Asp Leu
        530                 535                 540

Leu Asn Ser Leu Lys Ser Asn Val Ser Ser Val Ser Pro Ala Pro Val
545                 550                 555                 560

Leu Lys Asp Thr Val Ala Val Pro Ser Gly Gly Tyr Ala Ile Ile Lys
                565                 570                 575

Phe Arg Pro Lys Asn Pro Gly Tyr Trp Phe Leu His Cys His Phe Leu
            580                 585                 590

Tyr His Val Ala Thr Gly Met Ser Val Val Leu Gln Val Gly Glu Thr
        595                 600                 605

Ser Asp Tyr Pro Pro Thr Pro Asp Gly Phe Pro Lys Cys Gly Ser Phe
        610                 615                 620

Thr Pro Pro Val Asn Thr Asn Gly Gly His His His His His His
625                 630                 635
```

<210> SEQ ID NO 53
<211> LENGTH: 655
<212> TYPE: PRT
<213> ORGANISM: Artificial sequence
<220> FEATURE:
<223> OTHER INFORMATION: Recombinant Laccase 12

<400> SEQUENCE: 53

```
Met Leu Pro Cys Val Leu Leu Ala Cys Ala Ile Gly Val Ala Ser Ala
1               5                   10                  15

Thr Ser Val Leu Leu Asn Ser Tyr Leu Gln Pro Asn Asp Asp Ile Asp
            20                  25                  30

Arg Asn Thr Tyr Leu Leu Asn Ala Lys Ser Asn Asn Cys Ala Arg Ile
        35                  40                  45

Cys Asn Gly Thr Glu Ala Pro Lys Ile Cys Tyr Tyr Gln Trp Thr Ile
    50                  55                  60

Glu Asn Tyr Val Thr Leu Ser Glu Ala Cys Asp Asn Cys Pro Leu Asn
65                  70                  75                  80

Val Thr Ala Cys Tyr Asn Ala Gln Cys Ile Thr Ala Asp Gly Tyr Glu
                85                  90                  95

Arg Ser Ile Leu Ser Val Asn Arg Lys Leu Pro Gly Pro Ser Ile Glu
            100                 105                 110

Val Cys Leu Arg Asp Arg Val Ile Val Asp Ile Thr Asn Asn Met Ala
        115                 120                 125

Gly Arg Thr Thr Ser Ile His Trp His Gly Val Phe Gln Lys Gly Ser
    130                 135                 140

Gln Tyr Met Asp Gly Val Pro Met Val Thr Gln Cys Thr Ile His Glu
145                 150                 155                 160

Gly Asp Thr Leu Arg Tyr Asp Phe Ile Ala Asn Asn Glu Gly Thr His
                165                 170                 175

Phe Trp His Ser His Asp Gly Leu Gln Lys Leu Asp Gly Val Thr Gly
            180                 185                 190

Asn Leu Val Val Arg Val Pro Lys Asn Phe Asp Pro Asn Gly Gln Leu
        195                 200                 205

Tyr Asp Phe Asp Leu Pro Glu His Lys Ile Phe Ile Ser Asp Trp Leu
    210                 215                 220

His Leu Ser Ala Asp Asp His Phe Pro Gly Leu Arg Ala Thr Asn Pro
225                 230                 235                 240

Gly Gln Asp Ala Asn Ser Phe Leu Ile Asn Gly Arg Gly Arg Thr Leu
                245                 250                 255

Ile Gly Thr Gln Ser Thr Asn Thr Pro Tyr Ala Gln Ile Asn Val Gln
            260                 265                 270

Trp Gly Arg Arg Tyr Arg Leu Arg Ile Val Gly Ser Leu Cys Thr Val
        275                 280                 285

Cys Pro Thr Gln Leu Thr Ile Asp Gly His Lys Ile Thr Val Ile Ala
    290                 295                 300

Thr Asp Gly Asn Ser Val Ala Pro Ala Arg Val Asp Ser Leu Ile Ile
305                 310                 315                 320

Tyr Ser Gly Glu Arg Tyr Asp Val Val Leu Glu Ala Thr Asn Thr Glu
                325                 330                 335

Gly Ser Tyr Trp Ile His Leu Lys Gly Leu Val Thr Cys Val Gly Ser
            340                 345                 350

Arg Val Tyr Gln Leu Gly Val Leu Gln Tyr Glu Asn Thr Thr Thr Asn
        355                 360                 365
```

```
Lys Leu His Ala Leu Thr Pro Asp Pro Gly Tyr Asp Gly Phe Pro Gln
    370                 375                 380

Pro Ala Ser Tyr Arg Val Leu Asn Pro Glu Asn Ala Ser Cys Ser Ile
385                 390                 395                 400

Gly Ser Thr Gly Leu Cys Val Thr Gln Leu Ala Asn Ser Asp Pro Val
                405                 410                 415

Pro Arg Asp Ile Leu Thr Gln Leu Pro Asp Ile Asn Tyr Leu Leu Gln
                420                 425                 430

Phe Gly Phe Lys Ile Phe Asp Ser Arg Ser Phe Phe Lys Ala Tyr Asp
            435                 440                 445

Arg Tyr Phe Val Ser Pro Phe Leu Asp Leu Val Ser Ser Thr Val Asn
    450                 455                 460

Asn Ile Ser Ser Val Ser Pro Pro Ser Pro Leu Leu Ser Gln Arg Gly
465                 470                 475                 480

Asp Val Pro Asp Asp Val Leu Cys Pro Thr Gly Ala Asp Gly Leu Pro
                485                 490                 495

Gln Cys Pro Gly Gly Asn Ser Tyr Cys Thr Cys Val His Val Ile Lys
                500                 505                 510

Ile Lys Leu Gly Ala Leu Val Gln Ile Ile Leu Ser Asp Gln Thr Pro
            515                 520                 525

Lys Ser Gly Leu Asn His Pro Phe His Leu His Gly His Ala Phe Tyr
    530                 535                 540

Val Leu Gly Met Gly Gln Tyr Ala Ala Gly Gln Thr Ala Gln Asp Leu
545                 550                 555                 560

Leu Asn Ser Leu Lys Ser Asn Val Ser Ser Val Ser Pro Ala Pro Val
                565                 570                 575

Leu Lys Asp Thr Ile Ala Val Pro Ser Gly Gly Tyr Ala Ile Ile Lys
                580                 585                 590

Phe Arg Pro Lys Asn Pro Gly Tyr Trp Phe Leu His Cys His Phe Leu
            595                 600                 605

Tyr His Val Ala Thr Gly Met Ser Val Val Leu Gln Val Gly Glu Thr
    610                 615                 620

Ser Asp Tyr Pro Pro Thr Pro Asp Gly Phe Pro Lys Cys Gly Ser Phe
625                 630                 635                 640

Thr Pro Pro Val Asn Thr Asn Gly Gly His His His His His His
                645                 650                 655

<210> SEQ ID NO 54
<211> LENGTH: 639
<212> TYPE: PRT
<213> ORGANISM: Artificial sequence
<220> FEATURE:
<223> OTHER INFORMATION: Mature Laccase 12

<400> SEQUENCE: 54

Thr Ser Val Leu Leu Asn Ser Tyr Leu Gln Pro Asn Asp Asp Ile Asp
1               5                   10                  15

Arg Asn Thr Tyr Leu Leu Asn Ala Lys Ser Asn Asn Cys Ala Arg Ile
                20                  25                  30

Cys Asn Gly Thr Glu Ala Pro Lys Ile Cys Tyr Gln Trp Thr Ile
            35                  40                  45

Glu Asn Tyr Val Thr Leu Ser Glu Ala Cys Asp Asn Cys Pro Leu Asn
    50                  55                  60

Val Thr Ala Cys Tyr Asn Ala Gln Cys Ile Thr Ala Asp Gly Tyr Glu
65                  70                  75                  80
```

```
Arg Ser Ile Leu Ser Val Asn Arg Lys Leu Pro Gly Pro Ser Ile Glu
                85                  90                  95

Val Cys Leu Arg Asp Arg Val Ile Val Asp Ile Thr Asn Asn Met Ala
            100                 105                 110

Gly Arg Thr Thr Ser Ile His Trp His Gly Val Phe Gln Lys Gly Ser
            115                 120                 125

Gln Tyr Met Asp Gly Val Pro Met Val Thr Gln Cys Thr Ile His Glu
    130                 135                 140

Gly Asp Thr Leu Arg Tyr Asp Phe Ile Ala Asn Asn Glu Gly Thr His
145                 150                 155                 160

Phe Trp His Ser His Asp Gly Leu Gln Lys Leu Asp Gly Val Thr Gly
                165                 170                 175

Asn Leu Val Val Arg Val Pro Lys Asn Phe Asp Pro Asn Gly Gln Leu
                180                 185                 190

Tyr Asp Phe Asp Leu Pro Glu His Lys Ile Phe Ile Ser Asp Trp Leu
        195                 200                 205

His Leu Ser Ala Asp Asp His Phe Pro Gly Leu Arg Ala Thr Asn Pro
    210                 215                 220

Gly Gln Asp Ala Asn Ser Phe Leu Ile Asn Gly Arg Gly Arg Thr Leu
225                 230                 235                 240

Ile Gly Thr Gln Ser Thr Asn Thr Pro Tyr Ala Gln Ile Asn Val Gln
                245                 250                 255

Trp Gly Arg Arg Tyr Arg Leu Arg Ile Val Gly Ser Leu Cys Thr Val
                260                 265                 270

Cys Pro Thr Gln Leu Thr Ile Asp Gly His Lys Ile Thr Val Ile Ala
        275                 280                 285

Thr Asp Gly Asn Ser Val Ala Pro Ala Arg Val Asp Ser Leu Ile Ile
    290                 295                 300

Tyr Ser Gly Glu Arg Tyr Asp Val Val Leu Glu Ala Thr Asn Thr Glu
305                 310                 315                 320

Gly Ser Tyr Trp Ile His Leu Lys Gly Leu Val Thr Cys Val Gly Ser
                325                 330                 335

Arg Val Tyr Gln Leu Gly Val Leu Gln Tyr Glu Asn Thr Thr Thr Asn
            340                 345                 350

Lys Leu His Ala Leu Thr Pro Asp Pro Gly Tyr Asp Gly Phe Pro Gln
        355                 360                 365

Pro Ala Ser Tyr Arg Val Leu Asn Pro Glu Asn Ala Ser Cys Ser Ile
    370                 375                 380

Gly Ser Thr Gly Leu Cys Val Thr Gln Leu Ala Asn Ser Asp Pro Val
385                 390                 395                 400

Pro Arg Asp Ile Leu Thr Gln Leu Pro Asp Ile Asn Tyr Leu Leu Gln
                405                 410                 415

Phe Gly Phe Lys Ile Phe Asp Ser Arg Ser Phe Phe Lys Ala Tyr Asp
            420                 425                 430

Arg Tyr Phe Val Ser Pro Phe Leu Asp Leu Val Ser Ser Thr Val Asn
        435                 440                 445

Asn Ile Ser Ser Val Ser Pro Pro Ser Pro Leu Leu Ser Gln Arg Gly
    450                 455                 460

Asp Val Pro Asp Val Leu Cys Pro Thr Gly Ala Asp Gly Leu Pro
465                 470                 475                 480

Gln Cys Pro Gly Gly Asn Ser Tyr Cys Thr Cys Val His Val Ile Lys
                485                 490                 495
```

-continued

```
Ile Lys Leu Gly Ala Leu Val Gln Ile Ile Leu Ser Asp Gln Thr Pro
                500                 505                 510
Lys Ser Gly Leu Asn His Pro Phe His Leu His Gly His Ala Phe Tyr
            515                 520                 525
Val Leu Gly Met Gly Gln Tyr Ala Ala Gly Gln Thr Ala Gln Asp Leu
        530                 535                 540
Leu Asn Ser Leu Lys Ser Asn Val Ser Ser Val Ser Pro Ala Pro Val
545                 550                 555                 560
Leu Lys Asp Thr Ile Ala Val Pro Ser Gly Gly Tyr Ala Ile Ile Lys
                565                 570                 575
Phe Arg Pro Lys Asn Pro Gly Tyr Trp Phe Leu His Cys His Phe Leu
            580                 585                 590
Tyr His Val Ala Thr Gly Met Ser Val Val Leu Gln Val Gly Glu Thr
        595                 600                 605
Ser Asp Tyr Pro Pro Thr Pro Asp Gly Phe Pro Lys Cys Gly Ser Phe
610                 615                 620
Thr Pro Pro Val Asn Thr Asn Gly Gly His His His His His His
625                 630                 635

<210> SEQ ID NO 55
<211> LENGTH: 27
<212> TYPE: DNA
<213> ORGANISM: Artificial sequence
<220> FEATURE:
<223> OTHER INFORMATION: AKR truncated forward primer

<400> SEQUENCE: 55
tctagaatgg cgtttaagct agaaaaa                                      27

<210> SEQ ID NO 56
<211> LENGTH: 31
<212> TYPE: DNA
<213> ORGANISM: Artificial sequence
<220> FEATURE:
<223> OTHER INFORMATION: GHF7-3 forward primer

<400> SEQUENCE: 56
gatcagatct taatcaggat ttcacctaca c                                 31

<210> SEQ ID NO 57
<211> LENGTH: 30
<212> TYPE: DNA
<213> ORGANISM: Artificial sequence
<220> FEATURE:
<223> OTHER INFORMATION: GHF7-3 reverse primer

<400> SEQUENCE: 57
gatcggtacc ataagtgcta tcaatcggac                                   30

<210> SEQ ID NO 58
<211> LENGTH: 27
<212> TYPE: DNA
<213> ORGANISM: Artificial sequence
<220> FEATURE:
<223> OTHER INFORMATION: Beta-glu cellulase forward primer

<400> SEQUENCE: 58
gtcgacatga ggttacagac ggtttgc                                      27

<210> SEQ ID NO 59
<211> LENGTH: 47
<212> TYPE: DNA
```

<210> SEQ ID NO 59
<211> LENGTH: 47
<212> TYPE: DNA
<213> ORGANISM: Artificial sequence
<220> FEATURE:
<223> OTHER INFORMATION: Beta-glu cellulase reverse primer

<400> SEQUENCE: 59
ctgcagttag tgatgatggt gatgatggtc taggaagcgt tctggaa          47

<210> SEQ ID NO 60
<211> LENGTH: 89
<212> TYPE: DNA
<213> ORGANISM: Artificial sequence
<220> FEATURE:
<223> OTHER INFORMATION: GHF9 Cell-1 forward primer

<400> SEQUENCE: 60
ctagtctaga ctagatgaag atactccttg ctattgcatt aatgttgtca acagtaatgt     60
gggtgtcaac agctgcttac gactataag                                      89

<210> SEQ ID NO 61
<211> LENGTH: 56
<212> TYPE: DNA
<213> ORGANISM: Artificial sequence
<220> FEATURE:
<223> OTHER INFORMATION: GHF9 Cell-1 reverse primer

<400> SEQUENCE: 61
tttccttttg cggccgctta gtgatgatgg tgatgatgca cgccagcctt gaggag         56

<210> SEQ ID NO 62
<211> LENGTH: 28
<212> TYPE: DNA
<213> ORGANISM: Artificial sequence
<220> FEATURE:
<223> OTHER INFORMATION: Laccase forward primer

<400> SEQUENCE: 62
tctagaatgt tgccttgcgt cctgcttg                                       28

<210> SEQ ID NO 63
<211> LENGTH: 54
<212> TYPE: DNA
<213> ORGANISM: Artificial sequence
<220> FEATURE:
<223> OTHER INFORMATION: Laccase reverse primer

<400> SEQUENCE: 63
cggccgttag tgatgatggt gatgatgacc tccgttggtg ttcacgggag gtgt           54

LIGNASES AND ALDO-KETO REDUCTASES FOR CONVERSION OF LIGNIN-CONTAINING MATERIALS TO FERMENTABLE PRODUCTS

CROSS-REFERENCE TO RELATED APPLICATIONS

This application is the 35 U.S.C. §371 national stage of PCT Application No. PCT/US2013/025515, filed Feb. 11, 2013, which is entirely incorporated herein by reference and which also claims priority to, and the benefit of, U.S. provisional application entitled "NOVEL LIGNASES AND ALDO-KETO REDUCTASES FOR CONVERSION OF LIGNIN-CONTAINING MATERIALS TO FERMENTABLE PRODUCTS", having Ser. No. 61/602,149, filed on Feb. 23, 2012, which is entirely incorporated herein by reference.

STATEMENT REGARDING FEDERALLY SPONSORED RESEARCH OR DEVELOPMENT

This invention was made with Government support under Grant No. DE-FC03-97ER62402, awarded by the United States Department of Energy. The Government has certain rights in the invention.

SEQUENCE LISTING

The present application includes a sequence listing incorporated herein by reference in its entirety. The information recorded in computer readable form on the electronic version referenced herein is identical to the written sequence listing published with the referenced PCT application.

TECHNICAL FIELD

The present disclosure is generally related to enzymes, and to recombinant nucleic acid molecules encoding and/or expressing said enzymes, of the gut of the termite *Reticulitermes flavipes*. The disclosure further relates to a system combining said enzymes for converting a plant lignocellulose to a fermentable sugar-based product.

BACKGROUND

Lignocellulose is a sustainable global resource with a great deal of relevance to renewable energy production. In plants, lignocellulose provides key structural support for cell walls. Because it is plant-derived, lignocellulose is the most abundant and widespread bioenergy feedstock available on Earth. However, a major limitation in plant biomass utilization as a renewable energy source is the inefficiency of industrial lignocellulose depolymerization. This inefficiency increases energy inputs, reduces product yields, drives production costs higher, encourages political skepticism, and ultimately limits acceptance of cellulose-based renewable bioenergy. With respect to the problem of lignocellulose recalcitrance, it is germane that a number of invertebrate animals, and to some extent, their symbiotic gut fauna, have evolved specialized enzymes that cooperate in lignocellulose processing. In particular, endogenous lignocellulases encoded in marine and terrestrial invertebrate genomes can often confer high degrees of digestion capabilities to these organisms. When endogenous insect lignocellulases work synergistically with symbiont-derived enzymes, this can confer extremely high efficiency in lignocellulose processing. Termites (order Isoptera) are one of the most well recognized examples of an organism that subsists on lignocellulose; and thus, lignocellulase enzymes from termites and their gut symbionts have many potential bioenergy applications that warrant consideration.

Termites are social insects that subsist on sugars and other micronutrients obtained from nutritionally-poor lignocellulose diets (Ohkuma M., (2006) *Appl. Microbiol. Biotechnol.* 61: 1-9; Scharf & Tartar (2008) *Biofuels Bioprod. Birefin.* 2: 540-552). Lignocellulose is a natural complex of the biopolymers cellulose, hemicellulose, and lignin. Cellulose is composed of long $\beta$-1,4-linked polymers of glucose that are held together in bundles by hemicellulose (Ljungdahl & Erickson (1985) *Adv. Micro. Ecol.* 8: 237-299; Lange J. P., (2007) *Biofuels Bioprod. Bioref.* 1: 39-48). Hemicellulose is composed of shorter $\beta$-1,4-linked polymers of mixed sugars such as mannose, xylose, galactose, rhamnose, arabinose, glucuronic acid, mannuronic acid, and galacturonic acid (Saha B. C., (2003) *J. Indust. Microbiol. Biotechnol.* 30: 279-291). Lignin is a 3-dimensional polymer of phenolic compounds that are linked to each other and to hemicellulose by ester bonds. Lignin is composed of three "monolignol" monomers (p-coumaryl alcohol, coniferyl alcohol, and sinapyl alcohol), which are combined in different ratios depending on the plant species. Another important characteristic of hemicellulose is its esterification with monomers and dimers of phenolic acid esters, which are identical to the mono-lignols that compose lignin (Saha B. C., (2003) *J. Indust. Microbiol. Biotechnol.* 30: 279-291; Crepin et al., (2004) *Appl. Microbiol. Biotechnol.* 63, 647-652; Benoit et al., (2008) *Biotechnol. Letters* 30: 387-396).

Termites digest lignocellulose with the assistance of endogenous and symbiont-produced digestive enzymes and co-factors (Breznak & Brune (1995) *Appl. Env. Microbiol.* 61: 2681-2687; Watanabe et al., (1998) *Nature* 394: 330-331; Ohkuma et al., (2006) *Appl. Microbiol. Biotechnol.* 61: 1-9; Scharf & Tartar (2008) *Biofuels Bioprod. Birefin.* 2: 540-552). Termite gut endosymbionts include a diversity of microorganisms that include protozoa, bacteria, spirochetes, fungi, and yeast, among others (Breznak & Brune (1995) *Appl. Env. Microbiol.* 61: 2681-2687; Warnecke et al., (2007) *Nature* 450: 560-565). The order Isoptera is divided into the higher and lower termites based mostly on symbiont composition. Lower termites, including *Reticulitermes flavipes*, possess cellulolytic protozoa in addition to a host of hydrogenic, methanogenic, and nitrogen-fixing bacteria and spirochetes. Higher termites lack protozoa altogether, but instead possess cellulolytic bacteria. The roles of endosymbiotic fungi in higher and lower termites are not well defined; however, some higher termites cultivate fungus gardens in their nests that assist in lignocellulose digestion by producing cellulases, hemicellulases and lignases (Taprab et al., (2005) *Appl. Env. Microbiol.* 71: 7696-7704; Okhuma M., (2006) *Appl. Microbiol. Biotechnol.* 61: 1-9).

SUMMARY

Lignin is an obstacle to the economical production of biofuels from non-food lignocellulose feedstocks. Termites have specialized digestive systems that overcome the lignin barrier in wood to release fermentable simple sugars. The termite gut is thus considered a bioreactor model for enzyme-based production of biofuels from lignocellulose feedstocks. For this reason, using the termite *Reticulitermes flavipes* and its gut symbionts, high throughput titanium pyrosequencing and proteomics approaches experimentally compared the effects of lignin-containing diets on host-symbiont digestome composition. Over 9,000 distinct host and symbiont transcripts that are differentially expressed in response to diets with varying degrees of lignin complexity, including over 300 responsive cellulase, hemicellulase and candidate lignase transcripts, were identified. Proteomic investigations and functional digestive studies with recombinant lignocellulases conducted in parallel provided strong evidence of congruence at the transcription and translational levels and provide enzymatic strategies for overcoming recalcitrant lignin barriers in biofuel feedstocks.

Briefly described, therefore, one aspect of the disclosure provides embodiments of a system for generating a fermentable product from a lignified plant material, the system comprising a cooperating series of at least two catalytically active polypeptides, where said catalytically active polypeptides are selected from the group consisting of: cellulase Cell-1, β-glu cellulase, an aldo-keto-reductase, a catalase, a laccase, and an endo-xylanase.

In the embodiments of this aspect of the disclosure, the catalytically active polypeptides can have at least 90% sequence similarity with the amino acid sequence of a cellulase according to SEQ ID NOS.: 33, 34, 39, 40, 45, 48, and 50; a β-glucosidase according to SEQ ID NOS.: 42 and 43; an aldo-keto reductase according to SEQ ID NOS.: 21, 28, and 29; a catalase according to SEQ ID NO.: 23; or a laccase according to SEQ ID NOs.: 51-54.

In some embodiments of this aspect of the disclosure, the cooperating series of at least two catalytically active polypeptides can consist essentially of the isolated catalytically active domains of cellulases Cell-1 and β-glu and a catalytically active domain of at least one enzyme selected from the group consisting of an aldo-keto reductase, a catalase, and a laccase.

In some embodiments of this aspect of the disclosure, the catalytically active domains, or polypeptides comprising said catalytically active domains, are from a Cell-1, β-glu, and cellulase GHF7-3, and either an aldo-keto-reductase or a catalase.

In some embodiments of this aspect of the disclosure, the system consists essentially of the catalytically active domains, or polypeptides comprising said catalytically active domains, of an endo-xylanase and a laccase.

In some embodiments of this aspect of the disclosure, the cooperating series of at least two catalytically active peptides can consist essentially of the isolated catalytically active domains of an endo-xylanase and a laccase.

In some embodiments of this aspect of the disclosure, at least one of the Cell-1, the β-glu, the cellulase, the aldo-keto-reductase, the catalase, the laccase, and the endo-xylanase is derived from a termite.

In some embodiments of this aspect of the disclosure, at least one of the Cell-1, the β-glu, the cellulase, the aldo-keto-reductase, the catalase, the laccase, and the endo-xylanase is derived from a termite symbiont.

In some embodiments of this aspect of the disclosure, the catalytically active domains, or polypeptides comprising said catalytically active domains, can be expressed from a recombinant expression vector or vectors of a recombinant expression system.

In some embodiments of this aspect of the disclosure, the recombinant expression system is a eukaryotic cell-based system.

In some embodiments of this aspect of the disclosure, the catalytically active polypeptides or the isolated catalytically active domains thereof cooperate to provide a sugar from a lignified plant material.

In some embodiments of this aspect of the disclosure, the catalytically active polypeptides or the isolated catalytically active domains thereof cooperate to provide glucose from a lignified plant material.

In some embodiments of this aspect of the disclosure, the catalytically active polypeptides or the isolated catalytically active domains thereof cooperate to provide a pentose from a lignified plant material.

In some embodiments of this aspect of the disclosure, the laccase is LacA.

In some embodiments of this aspect of the disclosure, the system comprises the isolated catalytically active domains, or polypeptides comprising said catalytically active domains, of: (i) Cell-1, β-glu, cellulase GHF7-3, LacA, aldo-keto-reductase, and a catalase; (ii) Cell-1, β-glu, cellulase GHF7-3, and a catalase; (iii) Cell-1, β-glu, cellulase GHF7-3, and aldo-keto-reductase; (iv) Cell-1, β-glu, cellulase GHF7-3, and LacA; (v) Cell-1, β-glu, and cellulase GHF7-3; (vi) Cell-1, β-glu, and a catalase; (vii) Cell-1, β-glu, and aldo-keto-reductase; or (viii) LacA and GHF11-1.

Another aspect of the disclosure encompasses embodiments of a method of converting a lignified plant material to a fermentable product, the method comprising the steps of: (a) obtaining a system of isolated catalytically active domains, or polypeptides comprising said catalytically active domains, according to the disclosure; and (b) incubating the system with a source of lignified plant material, under conditions allowing the polypeptides to cooperatively produce a fermentable product from the lignified plant material.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A schematically illustrates a termite gut. SG, salivary gland; FG, Foregut; MG, midgut; MT, Malpighian tubules; HG, hindgut. Cellulolytic symbionts reside mainly in the HG region account for about ⅔ of lignocellulose digestion; host tissues (SG, FG and MG) account for about ⅓.

FIG. 1B is a table summarizing pyrosequencing data.

FIG. 1C illustrates a Venn diagram showing sequence distributions among the cellulose-subtracted wood and lignin libraries.

FIGS. 5A-5C are graphs illustrating sequence similarity distributions for the wood (FIG. 5A), lignin (FIG. 5B), and combined (wood+lignin) (FIG. 5C) datasets.

FIGS. 7A-7C provides a series of graphs illustrating BLASTx result distributions for the wood (FIG. 7A), lignin (FIG. 7B) and combined (wood+lignin) (FIG. 7C) datasets.

FIGS. 8A and 8B are bar graphs illustrating taxonomic hit summaries for the combined (wood+lignin) dataset. FIG. 8A: overall species hit distribution; FIG. 8B: top-hit species distributions.

FIG. 17A is a digital image of a two-dimensional PAGE analysis of soluble termite gut proteins from worker termites fed a diet of paper+lignin alkali. Highlighted spots were those chosen for analysis by tandem MS (n=26). Approximately 35 kDa protein spots were identified as being the most highly up-regulated in association with lignin alkali feeding.

FIG. 17B illustrates the amino acid sequences of aldo-keto reductase (AKR) sequenced peptides (SEQ ID NOS.: 1-19) (spots 1820, 1829, 1834).

FIG. 18 illustrates the nucleotide sequence (SEQ ID NO.: 20) of the assembled aldo-keto reductase nucleotide contig, which represents a cDNA sequence (1737 nucleotides). Two candidate start codons (ATG) are underlined, as well as the stop codon TAA, polyadenylation signal (AATAA) and poly-A tail (AAAAA$_n$).

FIG. 19 illustrates the translated AKR cDNA sequence (SEQ ID NO.: 21) and peptides sequenced by tandem MS. Nucleotides are shown in lower case letters and the amino acid translation (SEQ ID NO.: 20) is shown above nucleotides in capital letters. Gray highlighting indicates peptide sequences (SEQ ID NOS.: 1-19) as shown in FIG. 17B. Black highlighting indicates potential amino acid glycosylation sites. Dotted underlining indicates a putative signal peptide sequence (possible signal cleavage site indicated by "▼"). Two putative ATG start codons and the TAA stop codon are shown by underlined and bold font, as well as polyadenylation sites (AAATAAA) and poly A tails (AAAAAAAA).

FIG. 23A illustrates the synthetic nucleotide sequence (SEQ ID NO.: 22), codon-optimized for the host *Trichoplusia ni*, of catalase.

FIG. 23B illustrates the recombinant protein sequence (SEQ ID NO.: 23) of catalase. The mature protein sequence of the catalase lacks the first Met.

FIG. 24A illustrates the native nucleotide sequence of aldo-keto reductase (AKR) (SEQ ID NO.: 24). Positions of ATG start codons and a TAA termination codon are in bold.

Figure 2:
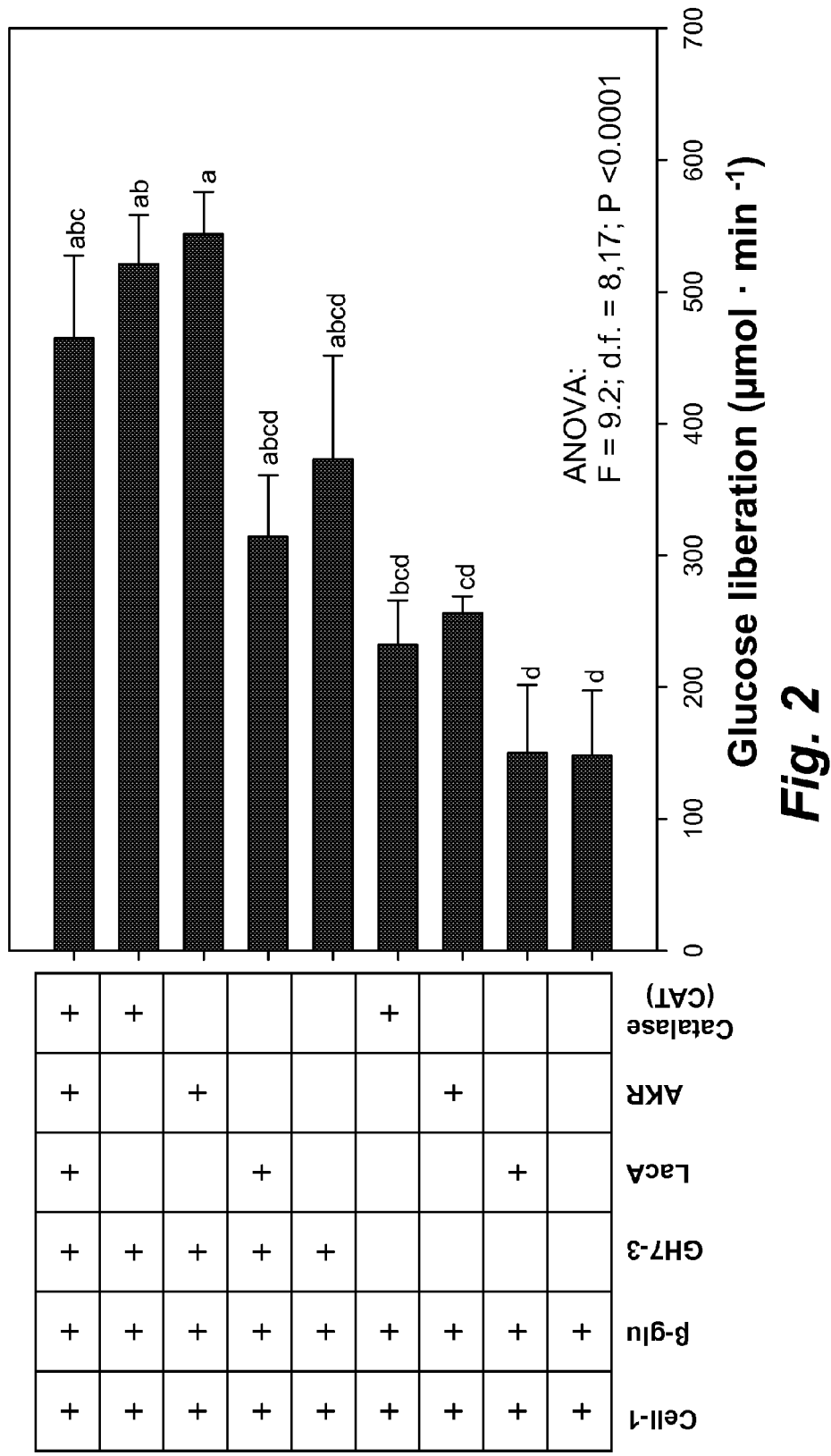
FIG. 2 is a bar graph illustrating glucose release from pine wood lignocellulose by recombinant enzyme cocktails. Bars represent micromoles of glucose released per minute (±std. error) for various combinations of recombinant enzymes encoded by differentially expressed genes identified in the present study. Six recombinant enzymes were tested: Cell-1, β-glu, GHF7-3, LacA, AKR and CAT. The first three enzymes are cellulases from Glycosyl Hydrolase Families (GHF) 9, 1 and 7; the latter three are lignase/phenol oxidase candidates from the laccase, aldo-keto reductase, and catalase families, respectively. All incubations lasted 18 hr.

The forward primer 3 (SEQ ID NO.: 25) and the reverse primer 5 (SEQ ID NO.: 26) positions are underlined.

FIG. 24B illustrates the synthetic nucleotide sequence, codon-optimized for the host *Trichoplusia ni*, of aldo-keto reductase (AKR) (SEQ ID NO.: 27).

FIG. 24C illustrates the recombinant protein sequence (SEQ ID NO.: 28) and the mature protein sequence of aldo-keto reductase (AKR) (SEQ ID NO.: 29).

FIG. 25 illustrates the nucleotide sequence (SEQ ID NO.: 30) of catalase (CAT).

FIG. 26 illustrates the nucleotide sequence (SEQ ID NO.: 31) of GHF7-3 cellulase.

FIG. 27A illustrates the synthetic nucleotide sequence (SEQ ID NO.: 32), codon-optimized for the host *Trichoplusia ni*, of GHF11-1 hemicellulase.

FIG. 27B illustrates the recombinant protein sequence (SEQ ID NO.: 33) and the mature protein sequence (SEQ ID NO.: 34) of GHF11-1 hemicellulase.

FIG. 28 illustrates the nucleotide sequence (SEQ ID NO.: 35) of LacA laccase. Positions of ATG start codons and a TAA termination codon are in bold and the positions of PCR primers (SEQ ID NOS.: 36 and 37) used for insertion into a baculovirus expression vector are underlined.

FIG. 29A illustrates the cloning strategy and the nucleotide sequence (SEQ ID NO.: 38) of GHF9 Cell-1 cellulase.

FIG. 29B illustrates the recombinant protein sequence (SEQ ID NO.: 39) and the mature protein sequence (SEQ ID NO.: 40) of GHF9 Cell-1 cellulase.

FIG. 30A illustrates the cloning strategy and full-length nucleotide sequence (SEQ ID NO.: 41) of β-glu cellulase.

FIG. 30B illustrates the recombinant protein sequence (SEQ ID NO.: 42) and the mature protein sequence (SEQ ID NO.: 43) of β-glu cellulase.

FIG. 31 illustrates the nucleotide sequence (SEQ ID NO.: 44) encoding GHF7-3 (SEQ ID NO.: 45) encompassing the region PCR amplified for cloning into the baculovirus expression vector. The natural ATG start codon, TAG stop codon, and the forward and reverse PCR primer positions (SEQ ID NOS.: 46 and 47, respectively) are indicated in bold and underlining.

FIG. 32 illustrates the amino acid sequence (SEQ ID NO.: 48) of the recombinant GHF7-3 protein sequence with a leader sequence and the thrombin-cleavable (His)6 terminus sequence GTLVPRGSHHHHHH (SEQ ID NO.: 49).

FIG. 33 illustrates the amino acid sequence (SEQ ID NO.: 50) of the recombinant GHF7-3 mature protein sequence.

FIG. 34 illustrates the recombinant protein sequence (SEQ ID NO.: 51) and the mature protein sequence (SEQ ID NO.: 52) of Laccase 6.

FIG. 35 illustrates the recombinant protein sequence (SEQ ID NO.: 53) and the mature protein sequence (SEQ ID NO.: 54) of Laccase 12.

The details of some exemplary embodiments of the methods and systems of the present disclosure are set forth in the description below. Other features, objects, and advantages of the disclosure will be apparent to one of skill in the art upon examination of the following description, drawings, examples and embodiments. It is intended that all such additional systems, methods, features, and advantages included within this description be within the scope of the present disclosure.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates, which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a support" includes a plurality of supports. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure, refer to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods compared to those of the corresponding compositions or methods disclosed herein.

Prior to describing the various embodiments, the following definitions are provided and should be used unless otherwise indicated.

DEFINITIONS

In describing the disclosed subject matter, the following terminology will be used in accordance with the definitions set forth below.

The term "termite gut" as used herein refers to the gut of *R. flavipes* workers. The gut of *R. flavipes* workers is composed of three main regions: foregut, midgut, and hindgut. The foregut region includes the esophagus, crop, and attached salivary gland. The salivary glands secrete endogenous (termite-derived) digestive factors and enzymes into the digestive tract. The midgut is a slender, tubular region that secretes a peritrophic matrix around food materials and, presumably, is a location where some lignocellulose degradation occurs. The Malpighian tubules connect at the junction of the midgut and hindgut and participate in waste excretion. The hindgut includes a fermentation chamber that is generally anaerobic in its core, but it does possess a micro-oxic zone around its periphery. The hindgut houses gut symbionts, and it is the location where most lignocellulose degradation, as well as fermentation and nutrient assimilation, are thought to occur.

The fermentation chamber of the hindgut is a source of microbial diversity. Microorganisms from various taxa present in the termite gut include bacteria/spirochetes and protozoans. In lower termites such as *R. flavipes*, protozoan symbionts are considered to be primarily involved in cellulose/hemicellulose degradation, while bacteria are considered important to nitrogen economy and simple sugar fermentation. Spirochetes, which are difficult to culture, are found in the hindguts of all termites. Spirochetes play roles in acetogenesis and nitrogen fixation, and they and other endomicrobionts also occur as cytoplasmic symbionts of hindgut protozoa.

The term "lignocellulose" as used herein refers to a natural complex of the three biopolymers: cellulose, hemicellulose and lignin. Cellulose is composed of rigid, high-molecular-weight, β-1,4-linked polymers of glucose that are held together in bundles by hemicellulose. Hemicellulose is composed of shorter β-1,4-linked polymers of mixed sugars. Mannose is usually the dominant sugar present in hemicelluloses of softwoods fed upon by termites, with lesser amounts of xylose, galactose, rhamnose, arabinose, glucuronic acid, mannuronic acid and galacturonic acid.

The term "lignin" as used herein refers to a 3-dimensional polymer of phenolic compounds that are linked to each other and to hemicellulose by ester bonds. Lignin is composed of the three mono-lignol monomers p-coumaryl alcohol, coniferyl alcohol, and sinapyl alcohol combined in different ratios depending on the plant species. Another noteworthy aspect of hemicellulose is its high degree of esterification with monomers and dimers of phenolic acid esters, which are analogous to the mono-lignols noted above. Phenolic acid esters are derived mostly from the mono-lignols p-coumaryl and coniferyl alcohol (i.e., coumaric acid and ferulic acid). The three individual lignocellulose components, cellulose, hemicellulose and lignin, compose approximately 40%, 25%, and 20%, respectively, of lignocellulose.

The term "pentose" as used herein refers to a monosaccharide with five carbon atoms. Pentoses are organized into two groups: aldopentoses having an aldehyde functional group at position 1; and ketopentoses have a ketone functional group in position 2 or 3. The aldopentoses have three chiral centers and therefore eight different stereoisomers are possible and include arabinose, xylose, and ribose. Ketopentoses have two chiral centers, and, therefore, four different stereoisomers are possible, and include ribulose and xylulose. The term "pentose" as used herein can refer to, but is not limited to, rhamnose, a naturally occurring deoxy sugar classified as a methyl-pentose or a 6-deoxy-hexose. Rhamnose occurs in nature in its L-form as L-rhamnose.

The term "catalase" as used herein refers to an enzyme that catalyzes the decomposition of hydrogen peroxide to water and oxygen. Catalase has one of the highest turnover numbers of all enzymes; one catalase molecule can convert millions of molecules of hydrogen peroxide to water and oxygen each second. Catalase is a tetramer of four polypeptide chains, each over 500 amino acids long. It contains four porphyrin heme (iron) groups that allow the enzyme to react with the hydrogen peroxide.

The term "aldo-keto reductase" as used herein refers to a family of enzymes that includes a number of related monomeric NADPH-dependent oxidoreductases, such as aldehyde reductase, aldose reductase, prostaglandin F synthase, xylose reductase, rho crystallin, and the like. All possess a similar structure, with a beta-alpha-beta fold characteristic of nucleotide binding novel NADP-binding motif. The hydrophobic nature of the pocket favors aromatic and apolar substrates over highly polar ones. Binding of the NADPH coenzyme causes a massive conformational change, reorienting a loop, effectively locking the coenzyme in place. This binding is more similar to FAD-than to NAD(P)-binding oxidoreductases.

The term "xylanase" as used herein refers to a class of enzymes which degrade the linear polysaccharide beta-1,4-xylan into xylose, thus breaking down hemicellulose, one of the major components of plant cell walls. As such, it plays a major role in micro-organisms thriving on plant sources. Xylanases are present in fungi for the degradation of plant matter into usable nutrients.

Esterases are hydrolytic enzymes that cleave ester bonds in a diversity of biomolecules (Oakeshott et al., (2005) in Gilbert et al., (eds.) Comprehensive Molecular Insect Science, Vol. 5, Elsevier-Pergamon, New York, pp. 309-382). Some insect esterases have very well defined biological functions, such as those involved in xenobiotic, lipid, acetylcholine, and juvenile hormone metabolism. However, many other insect esterases have largely undefined functions yet are extremely efficient at metabolizing model substrates such as naphthyl and p-nitrophenyl esters. This latter category of esterases is referred to as the "general esterases." Because of the highly esterified structure of lignin, it is possible that some general esterases may also contribute to lignin depolymerization in wood feeding insects such as termites.

The term "catalytically active domain" as used herein refers to an isolated region of an enzyme that retains the catalytic activity of the enzyme polypeptide found in the native cell. The size of the domain can vary according to the enzyme and the need to retain amino acid sequences that allow or maintain the three-dimensional structure of the enzymatically-active domain.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present disclosure include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, insect viruses (baculovirus), and the like, vectors derived from bacteriophage nucleic acid, and synthetic oligonucleotides like chemically synthesized DNA or RNA. The term "nucleic acid" further includes modified or derivatized nucleotides and nucleosides such as, but not limited to, halogenated nucleotides such as, but not only, 5-bromouracil, and derivatized nucleotides such as biotin-labeled nucleotides.

The term "isolated nucleic acid" as used herein refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present disclosure can include, for example, natural allelic variants as well as nucleic acid molecules modified by nucleotide deletions, insertions, inversions, or substitutions.

The term "enriched" as used herein in reference to nucleic acid is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased. The other DNA may, for example, be derived from a yeast or bacterial genome, or a cloning vector, such as a plasmid or a viral vector. The term "significant" as used herein is used to indicate that the level of increase is useful to the person making such an increase.

It is advantageous for some purposes that a nucleotide sequence is in purified form. The term "purified" in reference to nucleic acid represents that the sequence has increased purity relative to the natural environment.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

The terms "polypeptide" and "protein" as used herein refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or non-covalently linked to labeling ligands.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The terms "gene" or "genes" as used herein refer to nucleic acid sequences (including both RNA and DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes." The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and are, therefore, not naturally expressed in the cell.

The terms "expressed" or "expression" as used herein refer to the transcription from a gene to give an RNA nucleic acid molecule at least complementary in part to a region of one of the two nucleic acid strands of the gene. The terms "expressed" or "expression" as used herein also refer to the translation from said RNA nucleic acid molecule to give a protein, a polypeptide, or a portion or fragment thereof.

The term "operably linked" refers to an arrangement of elements wherein the components so described are configured so as to perform their usual function. Control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "cooperate to provide" and "cooperative" and the like as used herein refer to at least two enzymes, or functional fragments thereof, that convert a substrate compound to a product compound by a series of reactions catalyzed by the enzymes or fragments thereof. In cooperating, it is contemplated that the enzymes or functional fragments thereof may be physically associated as a single polypeptide expressed from a single nucleotide sequence, as a complex of the at least two polypeptides, a system wherein the enzymatically active polypeptides are not in association with one another, or partially so.

The terms "transcription regulatory sequences" and "gene expression control regions" as used herein refer to nucleotide sequences that are associated with a gene nucleic acid sequence and which regulate the transcriptional expression of the gene. Exemplary transcription regulatory sequences include enhancer elements, hormone response elements, steroid response elements, negative regulatory elements, and the like. The "transcription regulatory sequences" may be isolated and incorporated into a vector nucleic acid to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "promoter" as used herein refers to the DNA sequence that determines the site of transcription initiation from an RNA polymerase. A "promoter-proximal element" may be a regulatory sequence within about 200 base pairs of the transcription start site.

The term "coding region" as used herein refers to a continuous linear arrangement of nucleotides that may be translated into a protein. A full length coding region is translated into a full length protein (a complete protein as would be translated in its natural state absent any post-translational modifications). A full length coding region may also include any leader protein sequence or any other region of the protein that may be excised naturally from the translated protein.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein may further comprise modified bases wherein a modified adenine may form hydrogen bonds with a thymine or modified thymine, and a modified cytosine may form hydrogen bonds with a guanine or a modified guanine.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, chemiluminescent moieties, biotin, and the like that are well known in the art.

The terms "unique nucleic acid region" and "unique protein (polypeptide) region" as used herein refer to sequences present in a nucleic acid or protein (polypeptide) respectively that is not present in any other nucleic acid or protein sequence. The term "conserved nucleic acid region" as referred to herein is a nucleotide sequence present in two or more nucleic acid sequences to which a particular nucleic acid sequence can hybridize under low, medium or high stringency conditions. The greater the degree of conservation between the conserved regions of two or more nucleic acid sequences, the higher the hybridization stringency that will allow hybridization between the conserved region and a particular nucleic acid sequence.

The term "sense strand" as used herein refers to a single stranded DNA molecule from a genomic DNA that may be transcribed into RNA and translated into the natural polypeptide product of the gene. The term "antisense strand" as used herein refers to the single strand DNA molecule of a genomic DNA that is complementary with the sense strand of the gene.

The term "nucleic acid vector" as used herein refers to a natural or synthetic single or double stranded plasmid or viral nucleic acid molecule that can be transfected or transformed into cells and replicate independently of, or within, the host cell genome. A circular double stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that comprises a gene expression control region operably linked to a nucleotide sequence coding at least one polypeptide. As used herein, the term "regulatory sequences" includes promoters, enhancers, and other elements that may control gene expression. Standard molecular biology textbooks (for example, Sambrook et al., eds., 1989, "Molecular Cloning: A Laboratory Manual," 2nd ed., Cold Spring Harbor Press) may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only, a calcium or magnesium salt, an electric field, detergent, or liposome mediated transfection, to render the host cell competent for the uptake of the nucleic acid molecules, and by such methods as sperm-mediated and restriction-mediated integration.

The term "transfecting agent" as used herein refers to a composition of matter added to the genetic material for enhancing the uptake of heterologous DNA segment(s) into a eukaryotic cell including, but not limited to, an insect host cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell. Other preferred transfecting agents include, but are not limited to, lipofectin, lipofectamine, DIMRIE C, Supeffect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecytammonium bromide), DHDEAB (N,N-di-n-hexadecyl-N,N-dihydroxyethyl ammonium bromide), HDEAB (N-n-hexadecylN,N-dihydroxyethylammonium bromide), polybrene, poly(ethylenimine) (PEI) and the like.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, a single prokaryotic cell, or a mammalian cell. The recombinant cell may harbor a vector that is extragenomic. An extragenomic nucleic acid vector does not insert into the cell's genome. A recombinant cell may further harbor a vector or a portion thereof that is intragenomic. The term intragenomic defines a nucleic acid construct incorporated within the recombinant cell's genome.

The terms "recombinant nucleic acid" and "recombinant DNA" as used herein refer to combinations of at least two nucleic acid sequences that are not naturally found in a eukaryotic or prokaryotic cell. The nucleic acid sequences include, but are not limited to, nucleic acid vectors, gene expression regulatory elements, origins of replication, suitable gene sequences that when expressed confer antibiotic resistance, protein-encoding sequences, and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

The techniques used to isolate and characterize the nucleic acids and proteins of the present disclosure are well known to those of skill in the art, and standard molecular biology and biochemical manuals may be consulted to select suitable protocols without undue experimentation (see, for example, Sambrook et al., "Molecular Cloning: A Laboratory Manual," 2nd ed., 1989, Cold Spring Harbor Press; the content of which is incorporated herein by reference in its entirety).

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

"Denaturation" of a template molecule refers to the unfolding or other alteration of the structure of a template so as to make the template accessible to duplication. In the case of DNA, "denaturation" refers to the separation of the two complementary strands of the double helix, thereby creating two complementary, single stranded template molecules. "Denaturation" can be accomplished in any of a variety of ways, including by heat or by treatment of the DNA with a base or other denaturant.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR), which is defined and described in later sections below. The PCR process of Mullis is described in U.S. Pat. Nos. 4,683,195 and 4,683,202. PCR involves the use of a thermostable DNA polymerase, known sequences as primers, and heating cycles that separate the replicating deoxyribonucleic acid (DNA) strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves an enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

"DNA" refers to the polymeric form of deoxyribonucleotides (adenine, guanine, thymine, or cytosine) in either single stranded form or as a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

The terms "enzymatically amplify" or "amplify" as used herein refer, for the purposes of the specification or embodiments, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction), which utilizes DNA ligase, and a probe consisting of two halves of a DNA segment that is complementary to the sequence of the DNA to be amplified, enzyme Qβ replicase and a ribonucleic acid (RNA) sequence template attached to a probe complementary to the DNA to be copied, which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

As used herein, the term "genome" refers to all the genetic material in the chromosomes of a particular organism. Its size is generally given as its total number of base pairs.

Within the genome, the term "gene" refers to an ordered sequence of nucleotides located in a particular position on a particular chromosome that encodes a specific functional product (e.g., a protein or RNA molecule). In general, a patient's genetic characteristics, as defined by the nucleotide sequence of its genome, are known as its "genotype," while the patient's physical traits are described as its "phenotype."

The term "polymerase chain reaction" or "PCR" refers to a thermocyclic, polymerase-mediated, DNA amplification reaction. A PCR typically includes template molecules, oligonucleotide primers complementary to each strand of the template molecules, a thermostable DNA polymerase, and deoxyribonucleotides, and involves three distinct processes that are multiply repeated to effect the amplification of the original nucleic acid. The three processes (denaturation, hybridization, and primer extension) are often performed at distinct temperatures, and often in distinct temporal steps. In many embodiments, however, the hybridization and primer extension processes can be performed concurrently. The nucleotide sample to be analyzed may be PCR amplification products provided using the rapid cycling techniques described in U.S. Pat. Nos. 6,569,672; 6,569,627; 6,562,298; 6,556,940; 6,569,672; 6,569,627; 6,562,298; 6,556,940; 6,489,112; 6,482,615; 6,472,156; 6,413,766; 6,387,621; 6,300,124; 6,270,723; 6,245,514; 6,232,079; 6,228,634; 6,218,193; 6,210,882; 6,197,520; 6,174,670; 6,132,996; 6,126,899; 6,124,138; 6,074,868; 6,036,923; 5,985,651; 5,958,763; 5,942,432; 5,935,522; 5,897,842; 5,882,918; 5,840,573; 5,795,784; 5,795,547; 5,785,926; 5,783,439; 5,736,106; 5,720,923; 5,720,406; 5,675,700; 5,616,301; 5,576,218 and 5,455,175, the disclosures of which are incorporated by reference in their entireties. Other methods of amplification include, without limitation, NASBR, SDA, 3SR, TSA and rolling circle replication. It is understood that, in any method for producing a polynucleotide containing given modified nucleotides, one or several polymerases or amplification methods may be used. The selection of optimal polymerization conditions depends on the application.

A "polymerase" is an enzyme that catalyzes the sequential addition of monomeric units to a polymeric chain, or links two or more monomeric units to initiate a polymeric chain. In advantageous embodiments of this disclosure, the "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers.

A "primer" is an oligonucleotide, the sequence of at least a portion of which is complementary to a segment of a template DNA which is to be amplified or replicated. Typically primers are used in performing the polymerase chain reaction (PCR). A primer hybridizes with (or "anneals" to) the template DNA and is used by the polymerase enzyme as the starting point for the replication/amplification process. By "complementary" is meant that the nucleotide sequence of a primer is such that the primer can form a stable hydrogen bond complex with the template, i.e., the primer can hybridize or anneal to the template by virtue of the formation of base-pairs over a length of at least ten consecutive base pairs.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the term "protein" refers to a large molecule composed of one or more chains of amino acids in a specific order. The order is determined by the base sequence of nucleotides in the gene coding for the protein. Proteins are required for the structure, function, and regulation of the body's cells, tissues, and organs. Each protein has a unique function.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such DNA strand may be single-stranded or it may be part of a double-stranded DNA template. In applications of the present disclosure requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UITma, and variations and derivatives thereof.

Typically, the annealing of the primers to the target DNA sequence is carried out for about 2 min at about 37-55° C., extension of the primer sequence by the polymerase enzyme (such as Taq polymerase) in the presence of nucleoside triphosphates is carried out for about 3 min at about 70-75° C., and the denaturing step to release the extended primer is carried out for about 1 min at about 90-95° C. However, these parameters can be varied, and one of skill in the art would readily know how to adjust the temperature and time parameters of the reaction to achieve the desired results. For example, cycles may be as short as 10, 8, 6, 5, 4.5, 4, 2, 1, 0.5 min or less.

Also, "two temperature" techniques can be used where the annealing and extension steps may both be carried out at the same temperature, typically between about 60-65° C., thus reducing the length of each amplification cycle and resulting in a shorter assay time.

Typically, the reactions described herein are repeated until a detectable amount of product is generated. Often, such detectable amounts of product are between about 10 ng and about 100 ng, although larger quantities, e.g. 200 ng, 500 ng, 1 mg or more, can also be detected. In terms of concentration, the amount of detectable product can be from about 0.01 pmol, 0.1 pmol, 1 pmol, 10 pmol, or more. Thus, the number of cycles of the reaction that are performed can be varied; the more cycles performed, the more amplified product produced. In certain embodiments, the reaction comprises 2, 5, 10, 15, 20, 30, 40, 50, or more cycles.

For example, the PCR reaction may be carried out using about 25-50 µl samples containing about 0.01 to 1.0 ng of template amplification sequence, about 10 to 100 pmol of each generic primer, about 1.5 units of Taq DNA polymerase (Promega Corp.), about 0.2 mM dDATP, about 0.2 mM dCTP, about 0.2 mM dGTP, about 0.2 mM dTTP, about 15 mM $MgCl_2$, about 10 mM Tris-HCl (pH 9.0), about 50 mM KCl, about 1 µg/ml gelatin, and about 10 µl/ml Triton X-100 (Saiki, 1988).

Those of skill in the art are aware of the variety of nucleotides available for use in the cyclic polymerase mediated reactions. Typically, the nucleotides will consist at least in part of deoxynucleotide triphosphates (dNTPs), which are readily commercially available. Parameters for optimal use of dNTPs are also known to those of skill, and are described in the literature. In addition, a large number of nucleotide derivatives are known to those of skill and can be used in the present reaction. Such derivatives include fluorescently labeled nucleotides, allowing the detection of the product including such labeled nucleotides, as described below. Also included in this group are nucleotides that allow the sequencing of nucleic acids including such nucleotides as chain-terminating nucleotides, dideoxynucleotides and boronated nuclease-resistant nucleotides. Commercial kits containing the reagents most typically used for these methods of DNA sequencing are available and widely used. Other nucleotide analogs include nucleotides with bromo-, iodo-, or other modifying groups, which affect numerous properties of resulting nucleic acids including their antigenicity, their replicatability, their melting temperatures, their binding properties, etc. In addition, certain nucleotides include reactive side groups, such as sulfhydryl groups, amino groups, or N-hydroxysuccinimidyl groups, that allow the further modification of nucleic acids comprising them.

For the purposes of the present disclosure, sequence identity or homology is determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul (1990) *Proc. Natl. Acad. Sci. USA* 87: 2264-2268, modified as in Karlin & Altschul (1993) *Proc. Natl. Acad. Sci. USA* 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman (1988) *Proc. Natl. Acad. Sci. USA* 85: 2444-2448.

Advantageous for use according to the present disclosure is the WU-BLAST (Washington University BLAST) version 2.0 software. This program is based on WU-BLAST version 1.4, which in turn is based on the public domain NCBI-BLAST version 1.4 (Altschul & Gish, 1996, Local alignment statistics, Doolittle ed., *Methods Enzymol.* 266: 460-480; Altschul et al., (1990) *J. Mol. Biol.* 215: 403-410; Gish & States (1993) *Nature Genetics* 3: 266-272; Karlin & Altschul (1993) *Proc. Natl. Acad. Sci. USA* 90: 5873-5877; all of which are incorporated by reference herein).

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity" for instance, with respect to a nucleotide or amino acid sequence, can indicate a quantitative measure of homology between two sequences. The percent sequence homology can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$). "Homology" or "identity" can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman (1983) *Proc. Natl. Acad. Sci. U.S.A.* 80: 726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the disclosure and can be derived from DNA sequences by thymidine (T) in the DNA sequence being considered equal to uracil (U) in RNA sequences. Without undue experimentation, the skilled artisan can consult with many other programs or references for determining percent homology.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

The primers and probes described herein may be readily prepared by, for example, directly synthesizing the fragment by chemical means or by introducing selected sequences into recombinant vectors for recombinant production. Methods for making a vector or recombinants or plasmid for amplification of the fragment either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6,312,683; U.S. patent application Ser. No. 920,197, filed Oct. 16, 1986; WO 90/01543; WO91/11525; WO 94/16716; WO 96/39491; WO 98/33510; EP 265785; EP 0 370 573; Andreansky et al., (1996) *Proc. Natl. Acad. Sci. U.S.A.* 93: 11313-11318; Ballay et al., (1993) *EMBO J.* 4: 3861-3865; Feigner et al., (1994) *J. Biol. Chem.* 269: 2550-2561; Froto et al., (1996) *Proc. Natl. Acad. Sci. USA* 93: 11371-11377; Graham (1990) *Tibtech* 8: 85-87; Grunhaus et al., (1992) *Sem. Virol.* 3: 237-252; Ju et al., (1998) *Diabetologia* 41: 736-739; Kitson et al., (1991) *J. Virol.* 65: 3068-3075; McClements et al., (1996) *Proc. Natl. Acad. Sci. USA* 93: 11414-11420; Moss (1996) *Proc. Natl. Acad. Sci. USA* 93: 11341-11348; Paoletti (1996) *Proc. Natl. Acad. Sci. USA* 93: 11349-11353; Pennock et al., (1984) *Mol. Cell. Biol.* 4: 399-406; Richardson, ed., (1995) Methods in Molecular Biology, 39, "Baculovirus Expression Protocols," Humana Press Inc.; Smith et al., (1983) *Mol. Cell. Biol.* 3: 2156-2165; Robertson et al., (1996) *Proc. Natl. Acad. Sci. USA* 93: 11334-11340; Robinson et al., (1997) *Sem. Immunol.* 9: 271; and Roizman (1996) *Proc. Natl. Acad. Sci. USA* 93: 11307-11312.

DESCRIPTION

Figure 3:
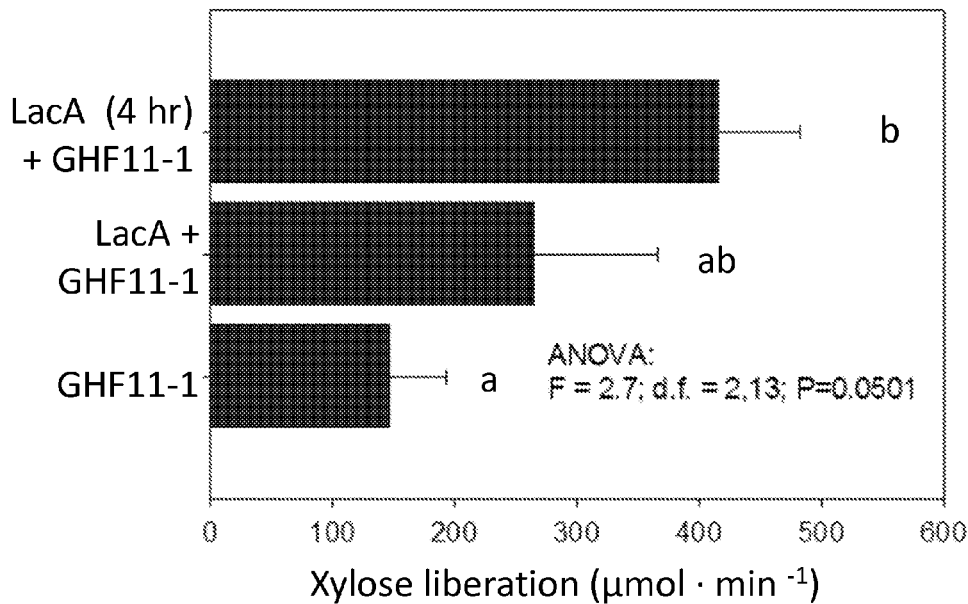
FIG. 3 is a bar graph illustrating xylose release from pine lignocellulose by recombinant GHF11-1 xylanase and LacA laccase enzyme cocktails. Bars represent micromoles of xylose released per minute (±std. error) for three treatments: (1) GHF11-1 alone, (2) co-incubation of GHF11-1+LacA, and (3) incubation with LacA for 4 hr before addition of GHF11-1. All GHF11-1 incubations lasted 18 hr.

The present disclosure encompasses systems and methods of use of said systems for the generation of fermentable compounds from lignified plant material using enzymes, or catalytically active domains thereof, derived from the gut of termites, whether encoded by the termite genome or by that of a symbiont organism. The systems comprise at least two termite-derived enzymes or the catalytically active domains thereof, that can cooperate to degrade lignified plant material to a fermentable compound such as, but not limited to, glucose, xylose, and the like. In particular, but not limiting, a combination of Cell-1, β-glucosidase, and GHF7 and a catalase release significant levels of glucose from lignified plant material. It is, however, contemplated to be within the scope of the disclosure for other combinations of enzyme activities to be formed based on the core pairing of the Cell-1, (β-glucosidase, as shown in FIGS. 2 and 3.

While enzymes or active fragments thereof may be isolated from tissues of termites, it is contemplated that nucleotide sequences encoding such polypeptides may be inserted into suitable expression vectors for the expression of the proteins in an in vitro system such as cultured cells. The enzymes or derivatives of such may then be isolated by methods well known in the art and combined with plant material under conditions allowing the enzymes to catalyze the breakdown of the lignin, cellulose, or hemicellulose into small sugar moieties.

The vast majority of termite digestive research has focused on cellulose digestion. However, the present disclosure provides an integrative approach to specifically resolve the question of how termites cope with their lignin-rich lignocellulose diets. Using a selective feeding approach and diets containing differing degrees of lignin complexity, over 9,000 differentially expressed host and symbiont transcripts that include over 300 responsive lignase/antioxidant, cellulase and hemicellulase transcripts were sequenced. Using protein-based approaches, congruence between our transcription and translation-level results was shown. The complex enzymatic machinery termites use to digest dietary lignocellulose was shown and support the idea that lignin and its degradation products present termites with significant xenobiotic challenges. Clearly, these challenges must be effectively overcome for termites and their gut symbiota to survive.

In addition to a previously identified LacA protein, embodiments of the present disclosure provide two candidate lignase/phenol oxidase enzyme families not previously considered in connection with lignocellulose saccharification: AKR and CAT. Recombinant AKR, CAT and LacA proteins, which apparently play no roles in cellulose and hemicellulose metabolism, have transcripts that are inducible by lignin feeding. Each significantly enhances lignocellulose saccharification by host and symbiont cellulases and/or xylanases. Thus, the present disclosure provides several important new enzyme families useful in the production of biofuels and other biomass-based goods.

The present disclosure encompasses systems of isolated enzymes derived from a termite or symbionts of a termite that are able to degrade the molecular structures of the components of lignified plant material to provide fermentable compounds, particularly sugars, that are useful for the production of biofuels. The methods of the disclosure allow the isolation of nucleic acid sequences encoding enzymes, or fragments thereof, that are used by termites or symbionts resident in the gut of termites and which are associated with the breakdown in vivo of ingested plant material to provide nutrients and energy sources for the insect. While it is possible to obtain polypeptides that encompass the entire amino acid sequences of the enzymes of the systems herein disclosed, it is further contemplated that truncated variants of the polypeptides may be produced by suitably locating PCR amplification primers such that the fore-shortened polypeptides may retain the catalytic activity of the native enzymes.

The enzymes identified by the methods of the disclosure may be provided as expressed products from in vitro or heterologous expression systems that allow for the isolation of the expressed products and their substantial purification. Thereafter, the isolated enzymatically active polypeptides of the disclosure may be combined in vitro to provide systems suitable for the digestion of plant material into fermentable products.

While not intended to be limiting, examples of termite-encoded enzymatically active polypeptides include Cell-1, β-glu, cellulase GHF7-3, an aldo-keto-reductase, a catalase, and a laccase. The isolated polypeptides (recombinant intact or variant forms thereof) may be combined in a range of systems, including, but not limited to, (i) Cell-1, β-glu, cellulase GHF7-3, LacA, aldo-keto-reductase, and a catalase; (ii) Cell-1, β-glu, cellulase GHF7-3, and a catalase; (iii) Cell-1, β-glu, cellulase GHF7-3, and aldo-keto-reductase; (iv) Cell-1, β-glu, cellulase GHF7-3, and LacA; (v) Cell-1, β-glu, and cellulase GHF7-3; (vi) Cell-1, β-glu, and a catalase; (vii) Cell-1, β-glu, and aldo-keto-reductase; or (viii) LacA AND GHF11-1.

For example, in one embodiment of the systems of the disclosure, PCR primers 3 and 5 (SEQ ID NOS.: 25 and 26, respectively) may be used to PCR amplify the entire aldo-keto reductase (AKR) polypeptide-encoding region or, by using the primers 4 and 5 (SEQ ID NOS.: 36 and 37), an N-terminus truncated variant thereof. It has been determined that each variant so generated and expressed in a suitable expression system, a baculovirus vector-lepidopteran larva host, exhibits similar enzymatic activity with a suitable substrate, and either variant may be included in the systems of the present disclosure for the generation of fermentable products from plant material.

One aspect of the disclosure, therefore, provides embodiments of a system for generating a fermentable product from a lignified plant material, the system comprising a cooperating series of at least two catalytically active polypeptides, where said catalytically active polypeptides are selected from the group consisting of cellulase Cell-1, β-glu cellulase, an aldo-keto-reductase, a catalase, a laccase, and an endo-xylanase.

In the embodiments of this aspect of the disclosure, the catalytically active polypeptides can have at least 90% sequence similarity with the amino acid sequence of a cellulase according to SEQ ID NOS.: 33, 34, 39, 40, 45, 48, and 50; a beta-glucosidase according to SEQ ID NOS.: 42 and 43; an aldo-keto reductase according to SEQ ID NOS.: 21, 28, and 29; a catalase according to SEQ ID NO.: 23; or a laccase according to SEQ ID NOs.: 51-54.

In some embodiments of this aspect of the disclosure, the cooperating series of at least two catalytically active polypeptides can consist essentially of the isolated catalytically active domains of cellulases Cell-1 and β-glu, and a catalytically active domain of at least one enzyme selected from the group consisting of an aldo-keto-reductase, a catalase, and a laccase.

In some embodiments of this aspect of the disclosure, the catalytically active domains, or polypeptides comprising said catalytically active domains, are from a Cell-1, β-glu, and cellulase GHF7-3, and either an aldo-keto-reductase or a catalase.

In some embodiments of this aspect of the disclosure, the catalytically active domains, or polypeptides comprising said catalytically active domains, can be an endo-xylanase and a laccase.

In some embodiments of this aspect of the disclosure, the cooperating series of at least two catalytically active peptides can consist essentially of the isolated catalytically active domains of an endo-xylanase and a laccase.

In some embodiments of this aspect of the disclosure, at least one of the Cell-1, the β-glu, the cellulase, the aldo-keto-reductase, the catalase, the laccase, and the endo-xylanase is derived from a termite.

In some embodiments of this aspect of the disclosure, at least one of the Cell-1, the β-glu, the cellulase, the aldo-keto-reductase, the catalase, the laccase, and the endo-xylanase is derived from a termite symbiont.

In some embodiments of this aspect of the disclosure, the catalytically active domains, or polypeptides comprising said catalytically active domains, can be expressed from a recombinant expression vector or vectors of a recombinant expression system. In some embodiments of this aspect of the disclosure, the recombinant expression system is a eukaryotic cell-based system.

In some embodiments of this aspect of the disclosure, the catalytically active polypeptides or the isolated catalytically active domains thereof cooperate to provide a sugar from a lignified plant material.

In some embodiments of this aspect of the disclosure, the catalytically active polypeptides or the isolated catalytically active domains thereof cooperate to provide glucose from a lignified plant material.

In some embodiments of this aspect of the disclosure, the catalytically active polypeptides or the isolated catalytically active domains thereof cooperate to provide a pentose from a lignified plant material.

In some embodiments of this aspect of the disclosure, the laccase is LacA.

In some embodiments of this aspect of the disclosure, the system comprises the isolated catalytically active domains, or polypeptides comprising said catalytically active domains, of (i) Cell-1, β-glu, cellulase GHF7-3, LacA, aldo-keto-reductase, and a catalase; (ii) Cell-1, β-glu, cellulase GHF7-3, and a catalase; (iii) Cell-1, β-glu, cellulase GHF7-3, and aldo-keto-reductase; (iv) Cell-1, β-glu, cellulase GHF7-3, and LacA; (v) Cell-1, β-glu, and cellulase GHF7-3; (vi) Cell-1, β-glu, and a catalase; (vii) Cell-1, β-glu, and aldo-keto-reductase; or (viii) LacA and GHF11-1.

Another aspect of the disclosure encompasses embodiments of a method of converting a lignified plant material to a fermentable product, the method comprising the steps of (a) obtaining a system of isolated catalytically active domains, or polypeptides comprising said catalytically active domains, according to the disclosure; and (b) incubating the system with a source of lignified plant material, under conditions allowing the polypeptides to cooperatively produce a fermentable product from the lignified plant material.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Figure 4:
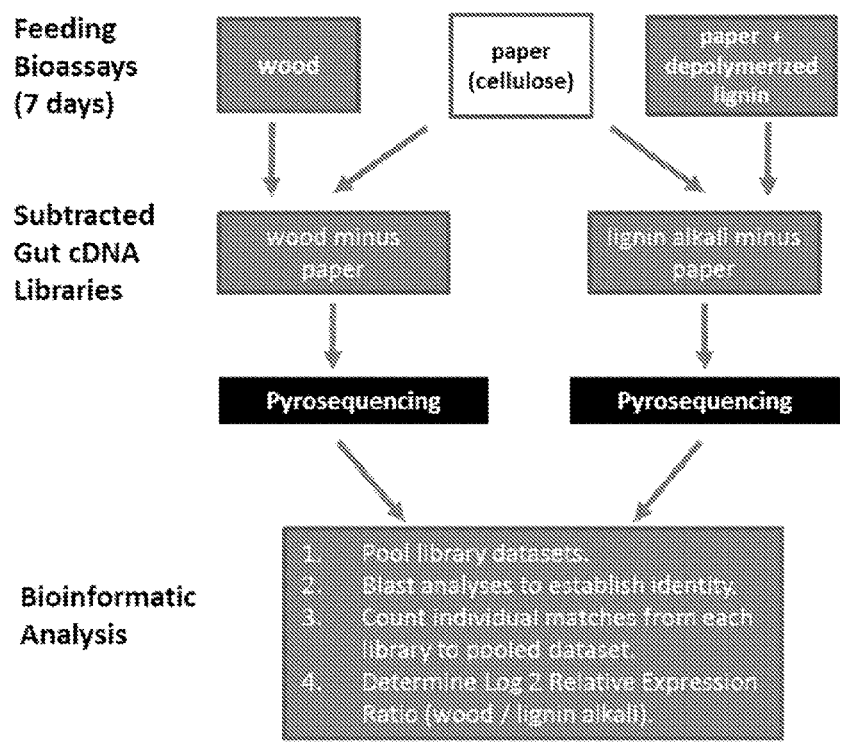
FIG. 4 schematically illustrates an experimental design flow chart over-viewing bioassay, molecular biology and bioinformatic procedures.
Figure 6A:
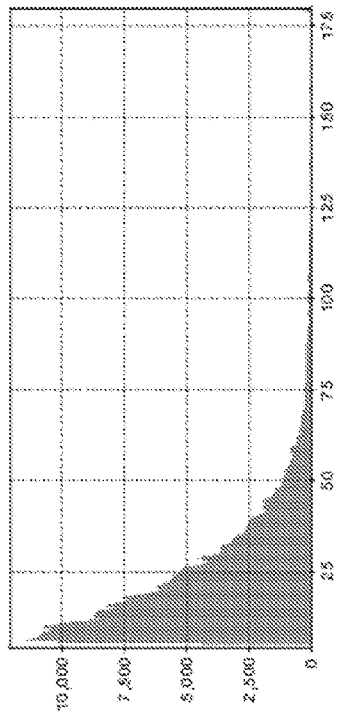
FIGS. 6A-6C provides a series of graphs illustrating E-value distributions for the wood (FIG. 6A), lignin (FIG. 6B) and combined (wood+lignin) (FIG. 6C) datasets.
Figure 6B:
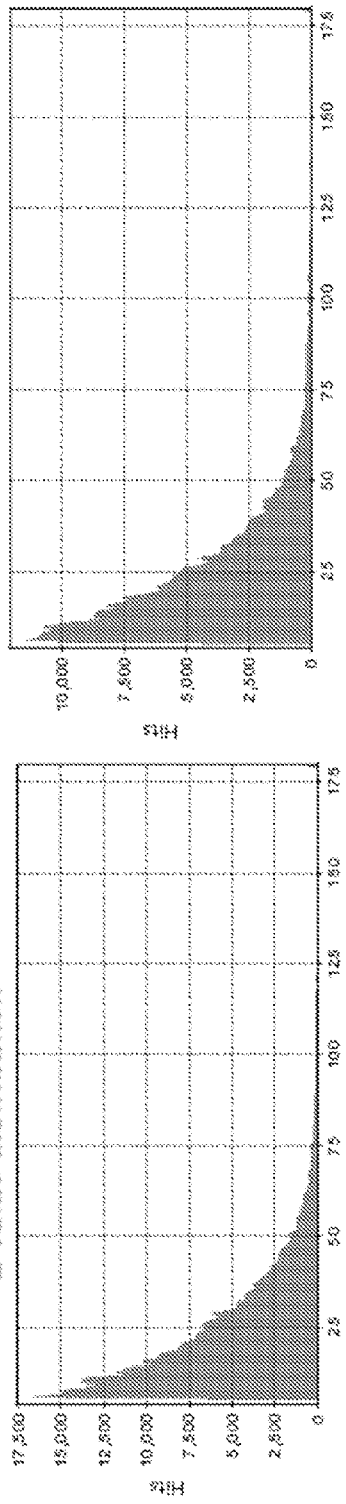
Figure 6C:
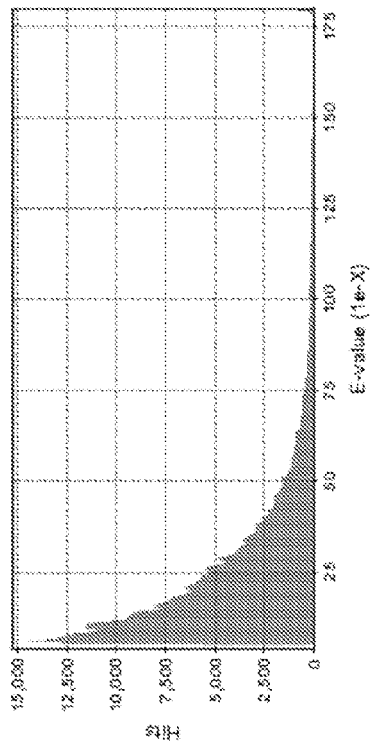

Groups of *R. flavipes* workers (200 per treatment; 50 from each of four colonies) received three diet treatments for 7 days before isolation of total gut RNA (FIG. 4). Diet treatments included highly pure cellulose (filter paper), complex lignocellulose (pine wood), and cellulose+depolymerized lignin (i.e., lignin alkali), which is an industrial de-lignification byproduct containing depolymerized lignin and related phenolic compounds. The isolation of whole-gut RNA after 7 days enabled digestome-wide sampling for expressed transcripts from host termite gut tissue and eukaryotic protist gut symbionts (FIG. 1A). One mRNA pool was isolated for each feeding treatment. To enrich for lignin- and other phenolic-responsive transcripts, the cellulose-fed mRNA pool was subtracted from the wood and depolymerized lignin preparations to create two "subtracted" cDNA libraries. The two subtracted libraries were subjected to 454 titanium pyrosequencing using established parameters and the contig sequences were assembled de novo under genome settings.

Sequencing Overview:

From the two subtracted libraries, 346,798 sequencing reads were obtained that provided 98,960,499 nucleotide bases with an average read length of 285 nucleotide bases (FIG. 1B). Resulting sequences were assembled into 9,552 multiple-read contigs and 97,254 single-read singletons. Of the 9,552 differentially expressed contigs, 3,444 were uniformly represented in the two cellulose-subtracted libraries, and thus were considered to be phenolic-responsive (FIG. 1C). A total of 3,436 contigs were unique to the wood library and 2,763 to the depolymerized lignin library. The wood-library transcripts are considered to be responsive to intact/polymerized lignin and hemicellulose, whereas the depolymerized lignin-library transcripts are considered to be responsive to depolymerized lignin and related degradation products. Sequence similarity length assessments showed a normal distribution with median values of 60-75 bases (FIGS. 5A-5C).

Example 2

BLAST Summaries

Figure 8B:
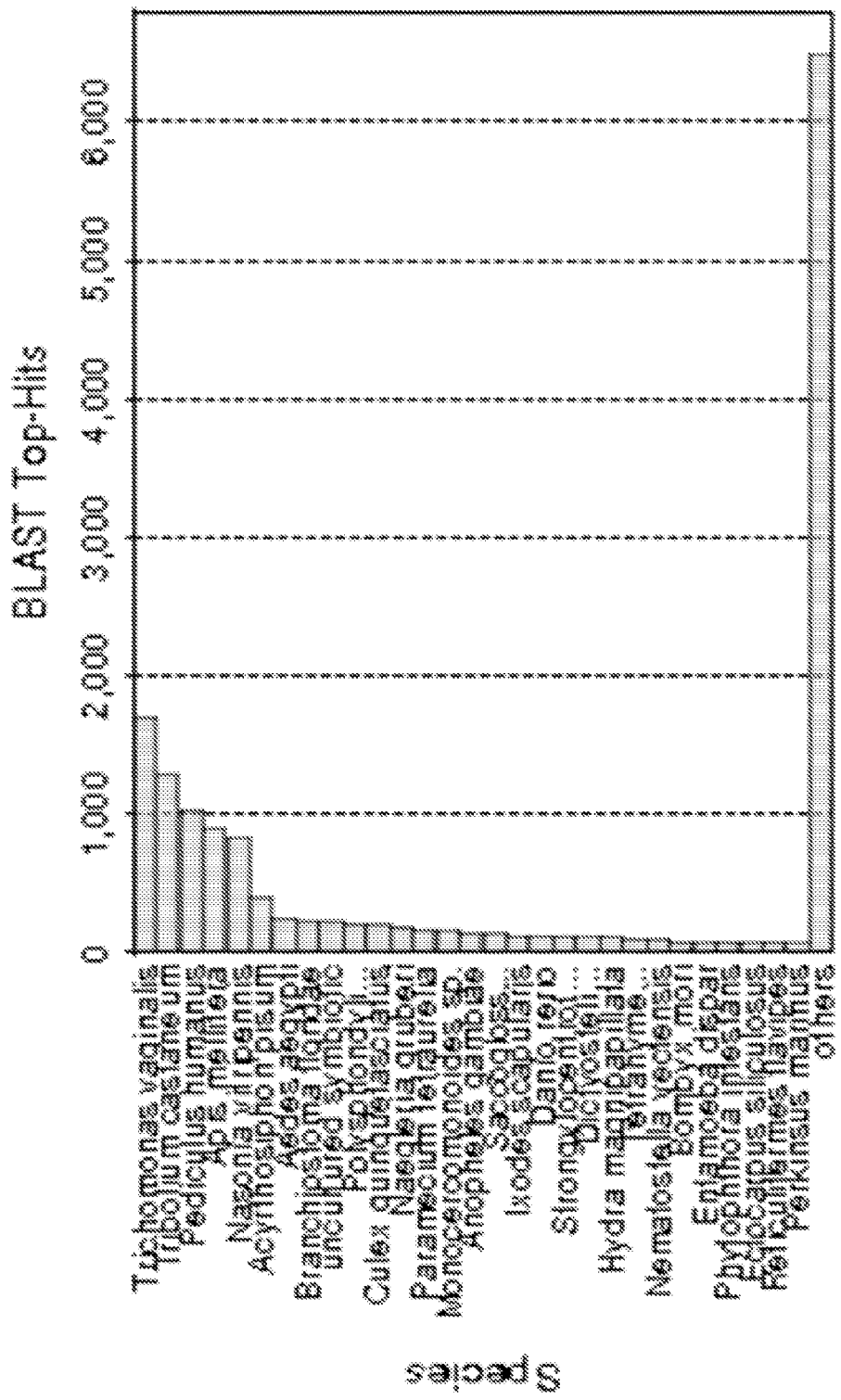

Consistent with a previous *R. flavipes* sequencing project (Tartar et al., (2009) *Biotechnol. Biofuels* 2: 25), e-value distributions for sequence database matches indicated most individual sequence reads had no translated BLASTx database matches (FIGS. 6A-6C and 7A-7C). However, the number of translated (BLASTx) database matches improved when using contigs generated from the combined wood and lignin libraries, i.e., 45% of the combined dataset contigs (n=4,337) had significant matches. Genome database matches from the pyrosequence dataset included multiple insect genomes, as well as the genome of the protist *Trichomonas vaginalis* and a number of insect symbiont genomes and metagenomes (FIGS. 8A and 8B). Comparatively fewer prokaryote and euryarchaeota sequences were identified. These taxonomic characteristics reflect the eukaryotic poly-A RNA targeted approach, as well as the unique eukaryotic host-symbiont relationship that exists in *R. flavipes*.

Example 3

Gene Ontology (GO) Summaries

Figure 9A:
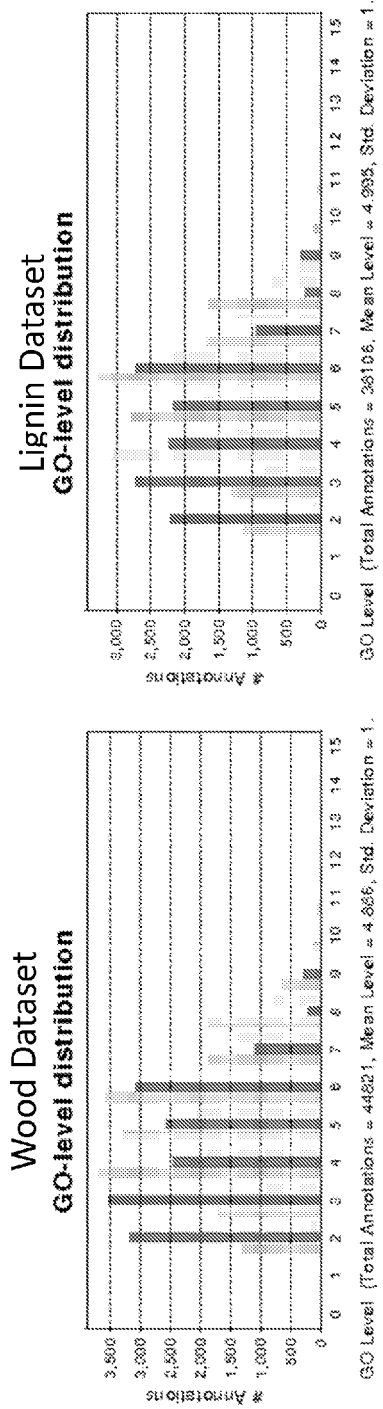
FIGS. 9A-9C provides a series of graphs illustrating GO-level distributions for the wood (FIG. 9A), lignin (FIG. 9B) and combined (wood+lignin) (FIG. 9C) datasets. P: biological process; F: molecular function; C: cellular location.
Figure 9B:
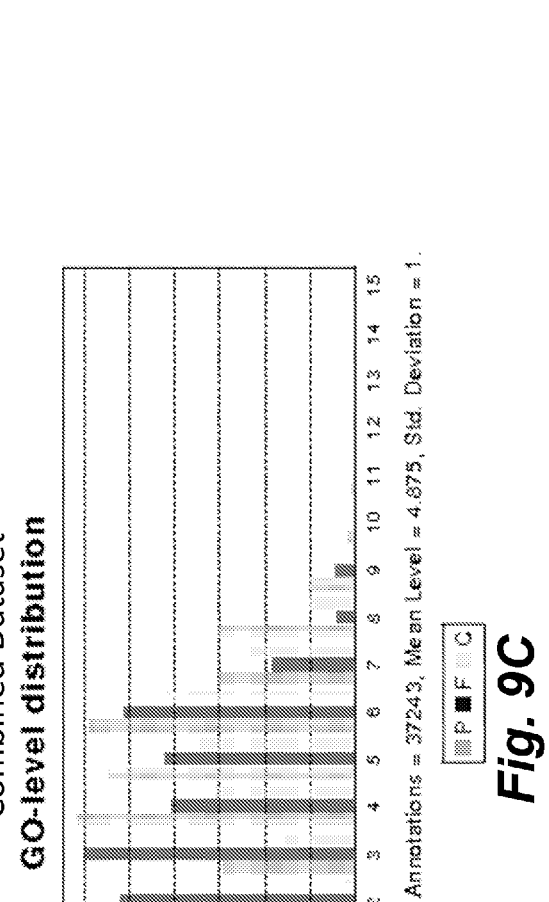
Figure 9C:
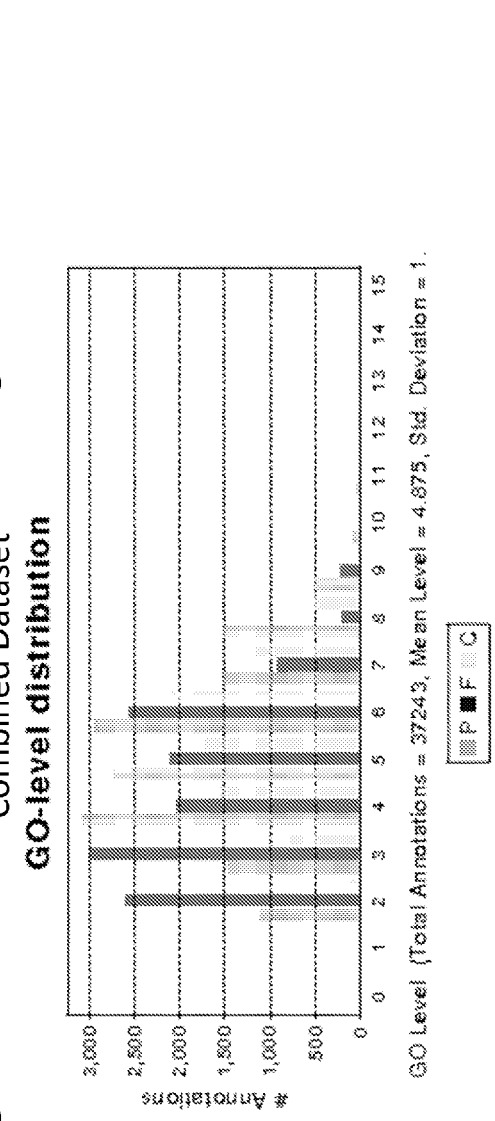
Figure 10A:
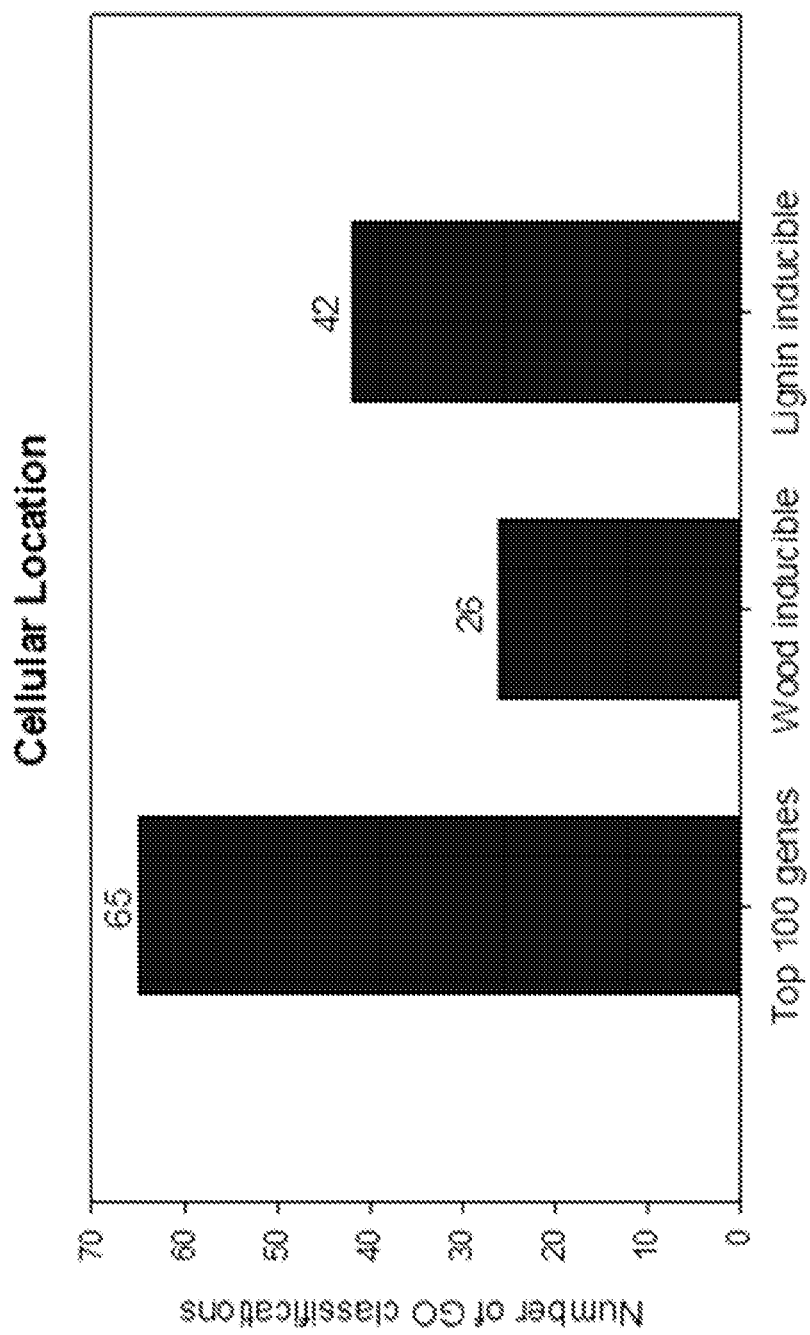
FIG. 10A is a bar graph illustrating cellular location GO comparisons among the top 100 overall expressed transcripts.
Figure 10D:
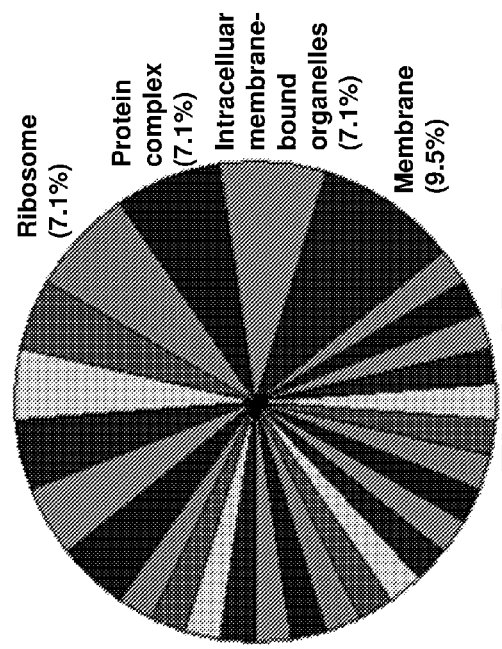
FIGS. 10B-10D provides a series of pie charts illustrating the cellular location GO comparisons among the top 100 overall expressed transcripts (FIG. 10B); top 100 wood-library transcripts (FIG. 10C), and top 100 lignin-library transcripts (FIG. 10D).
Figure 10B:
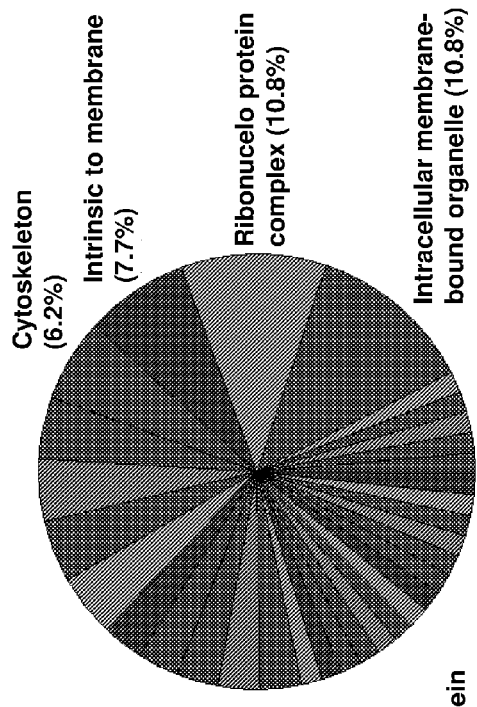
Figure 10C:
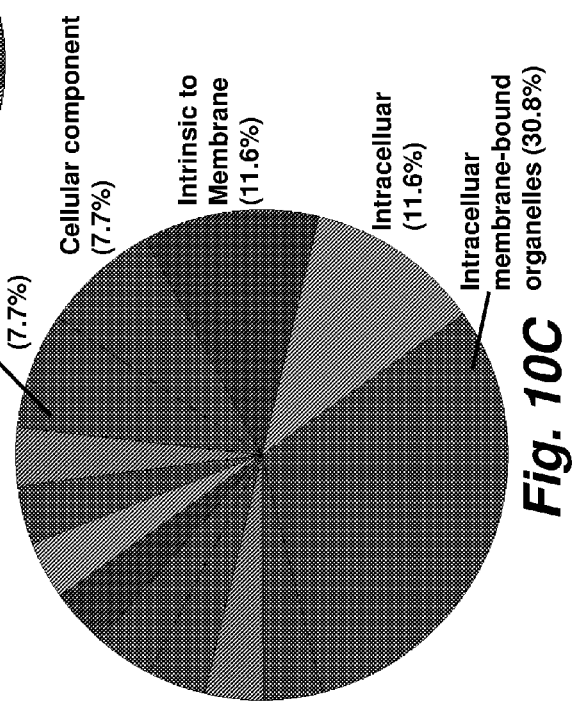
Figure 11A:
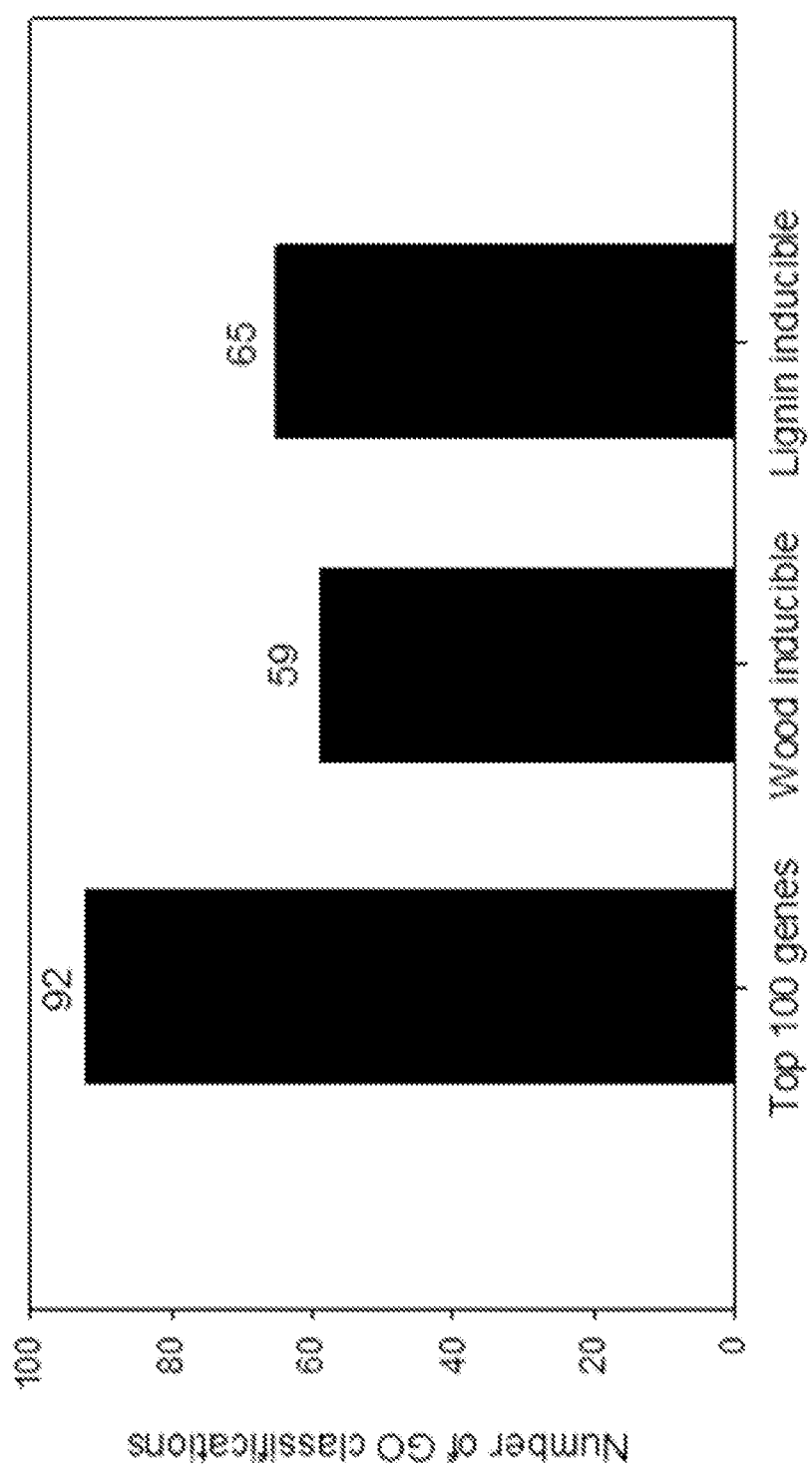
FIG. 11A is a graph illustrating molecular function GO comparisons among the top 100 overall expressed transcripts.
Figure 11D:
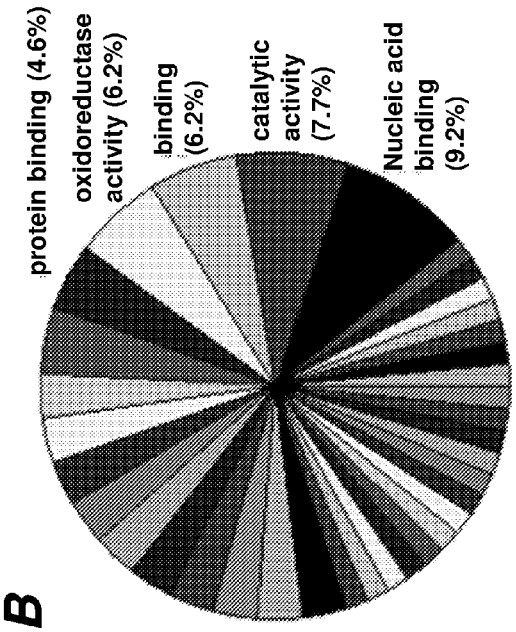
FIGS. 11B-11D provides a series of pie charts illustrating the molecular function GO comparisons among the top 100 overall expressed transcripts (FIG. 11B); top 100 wood-library transcripts (FIG. 11C), and top 100 lignin-library transcripts (FIG. 11D).
Figure 11B:
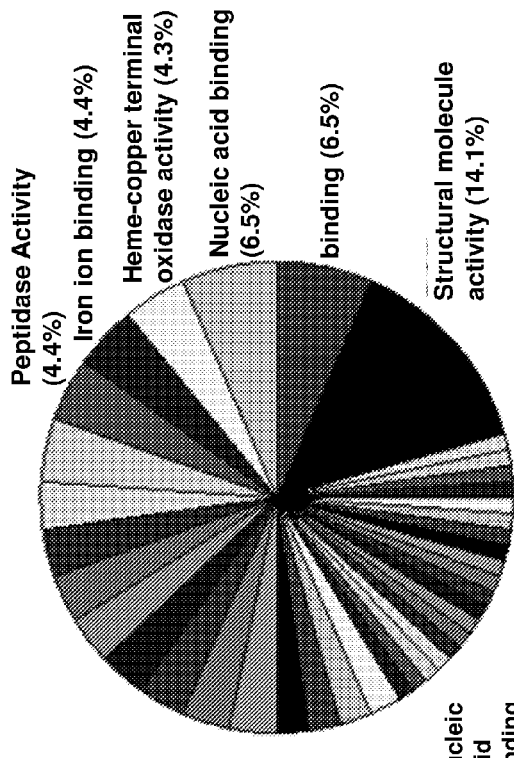
Figure 11C:
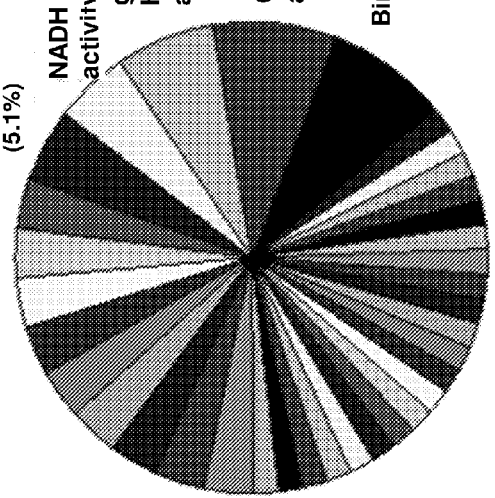
Figure 12A:
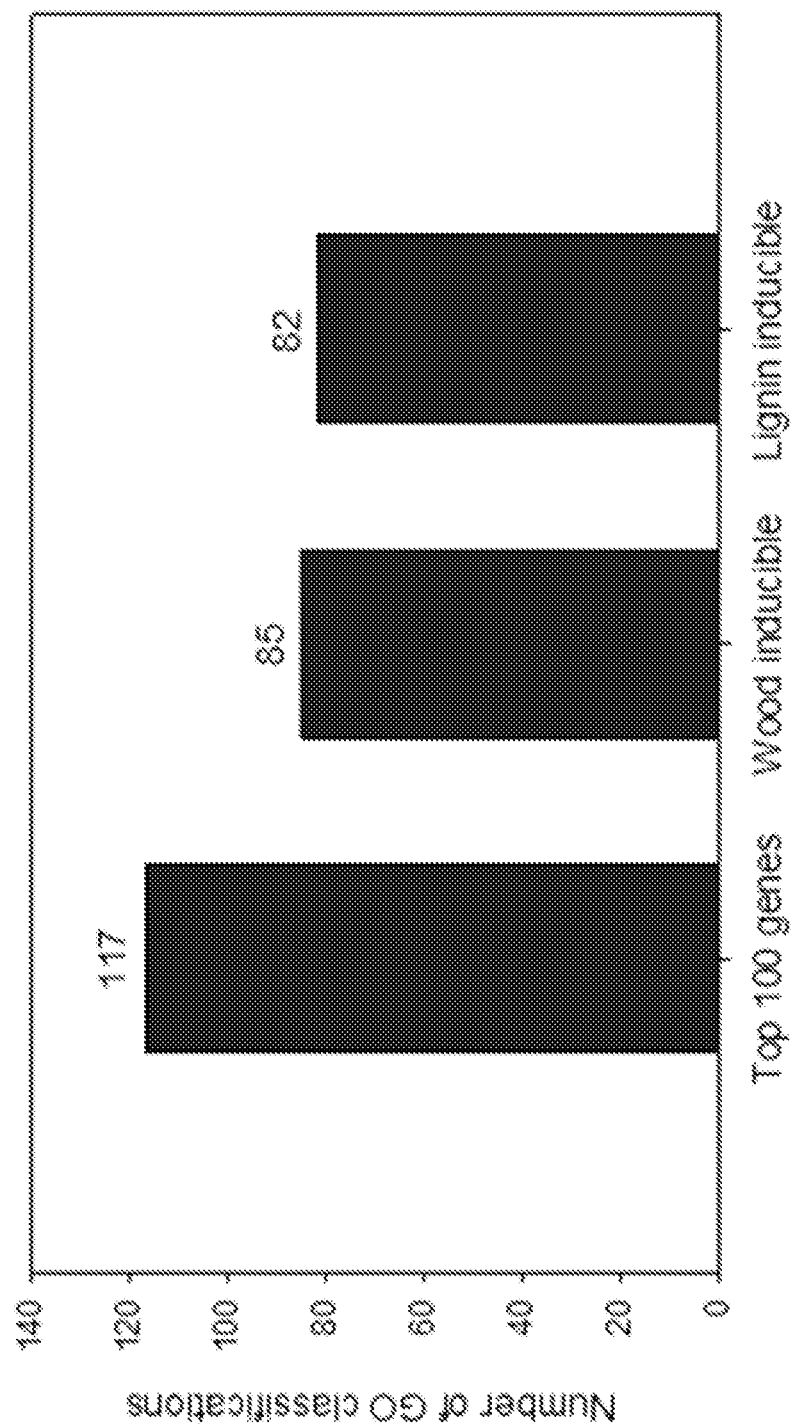
FIG. 12A is a graph illustrating biological process GO comparisons among the top 100 overall expressed transcripts.
Figure 12B:
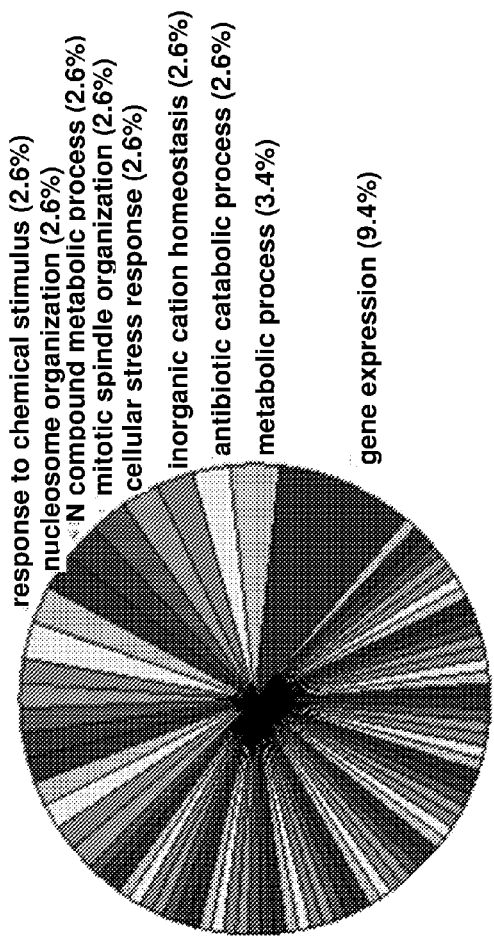
FIGS. 12B-12D provides a series of pie charts illustrating the biological process GO comparisons among the top 100 overall expressed transcripts (FIG. 12B); top 100 wood-library transcripts (FIG. 12C), and top 100 lignin-library transcripts (FIG. 12D).
Figure 12C:
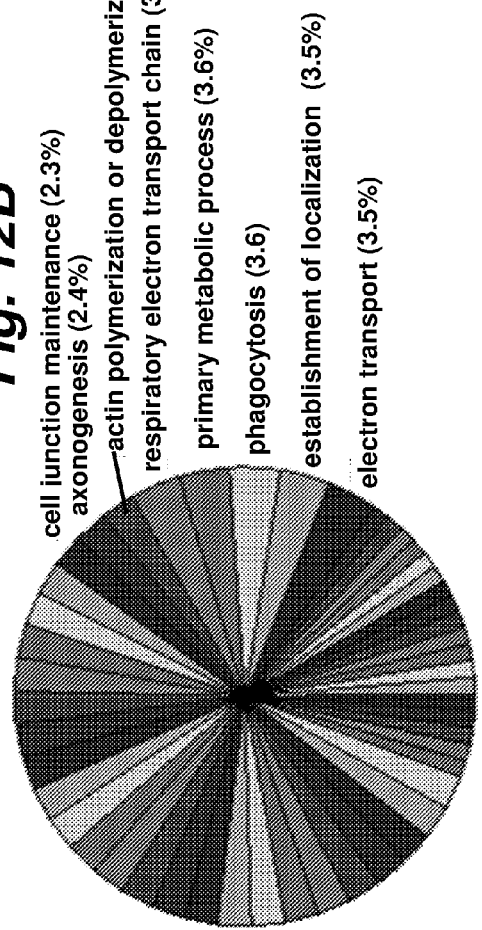
Figure 12D:
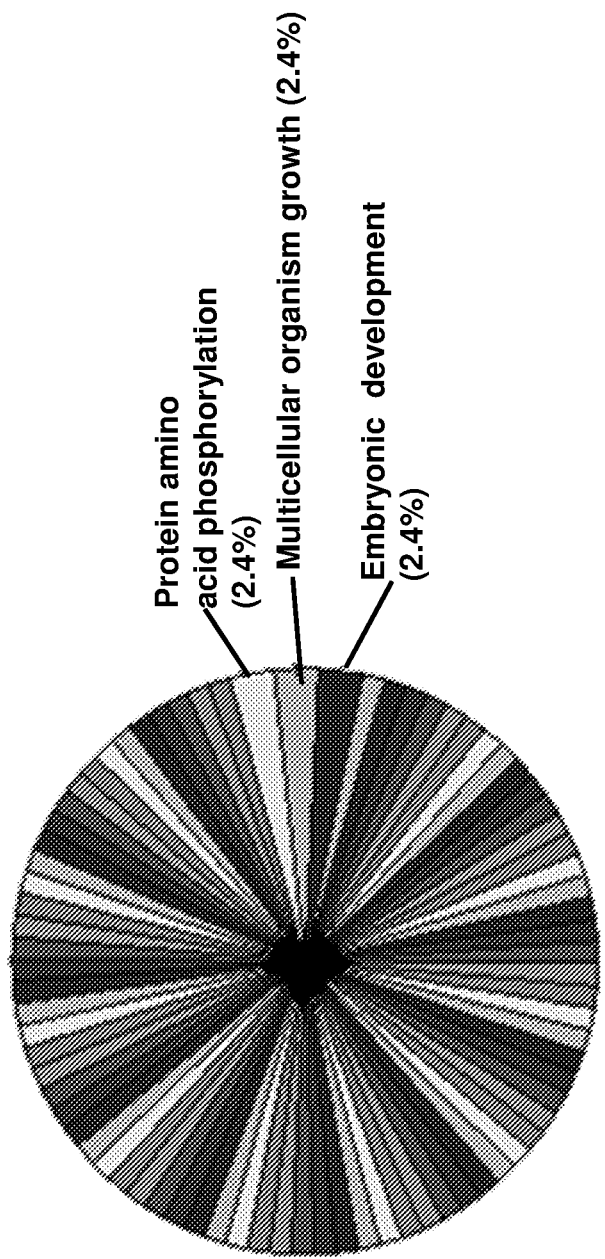
Figure 13A:
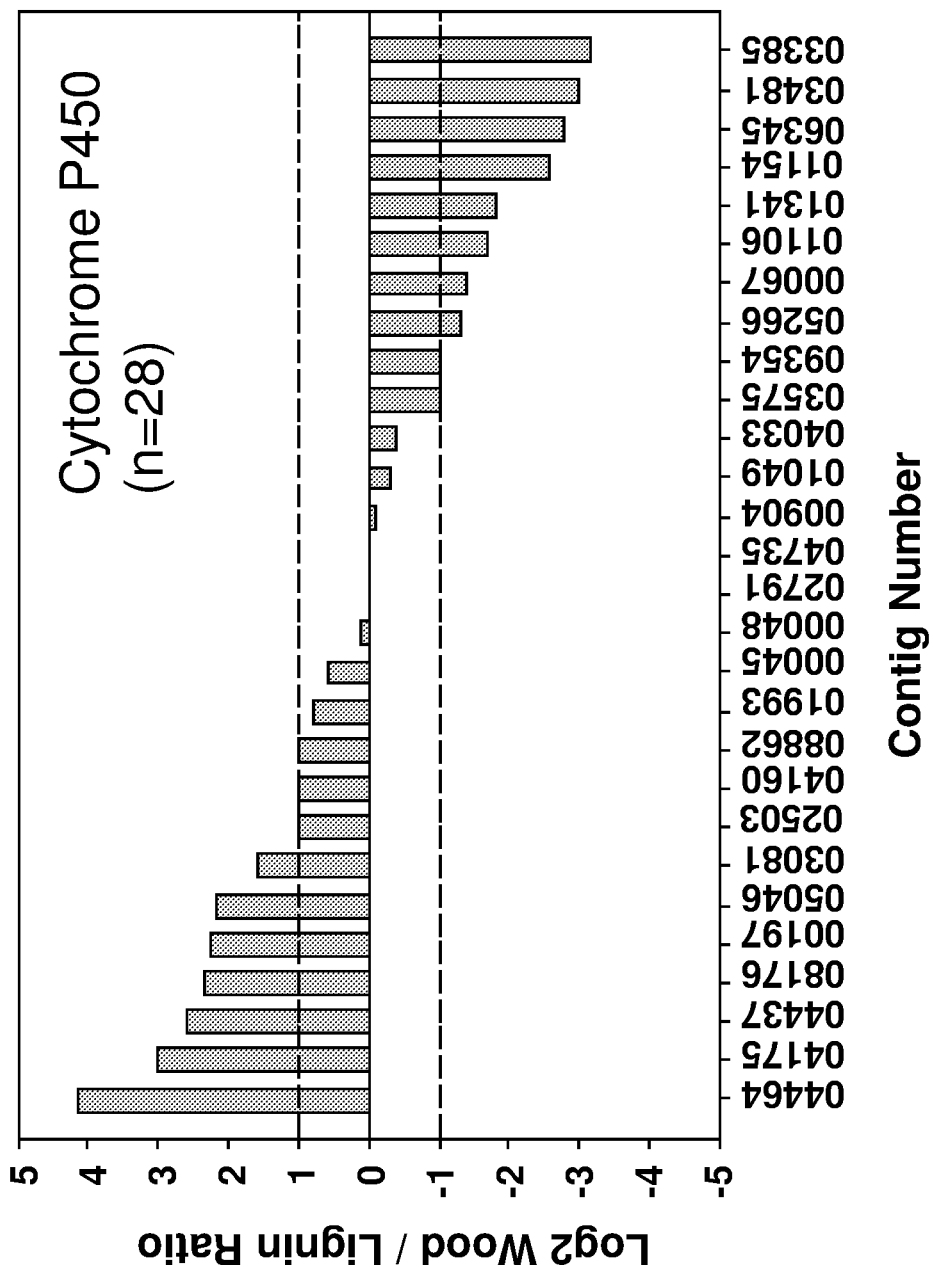
FIGS. 13A-13I provides a series of bar graphs illustrating expression summaries and contig numbers for differentially expressed lignase and detoxification candidate genes. Bars indicate Log 2 transformed wood library:lignin library expression ratios. Values >1=wood inducible, values <1=lignin inducible, and values between +1 and −1=general phenolic responsive (i.e., shared among both libraries).
Figure 13B:
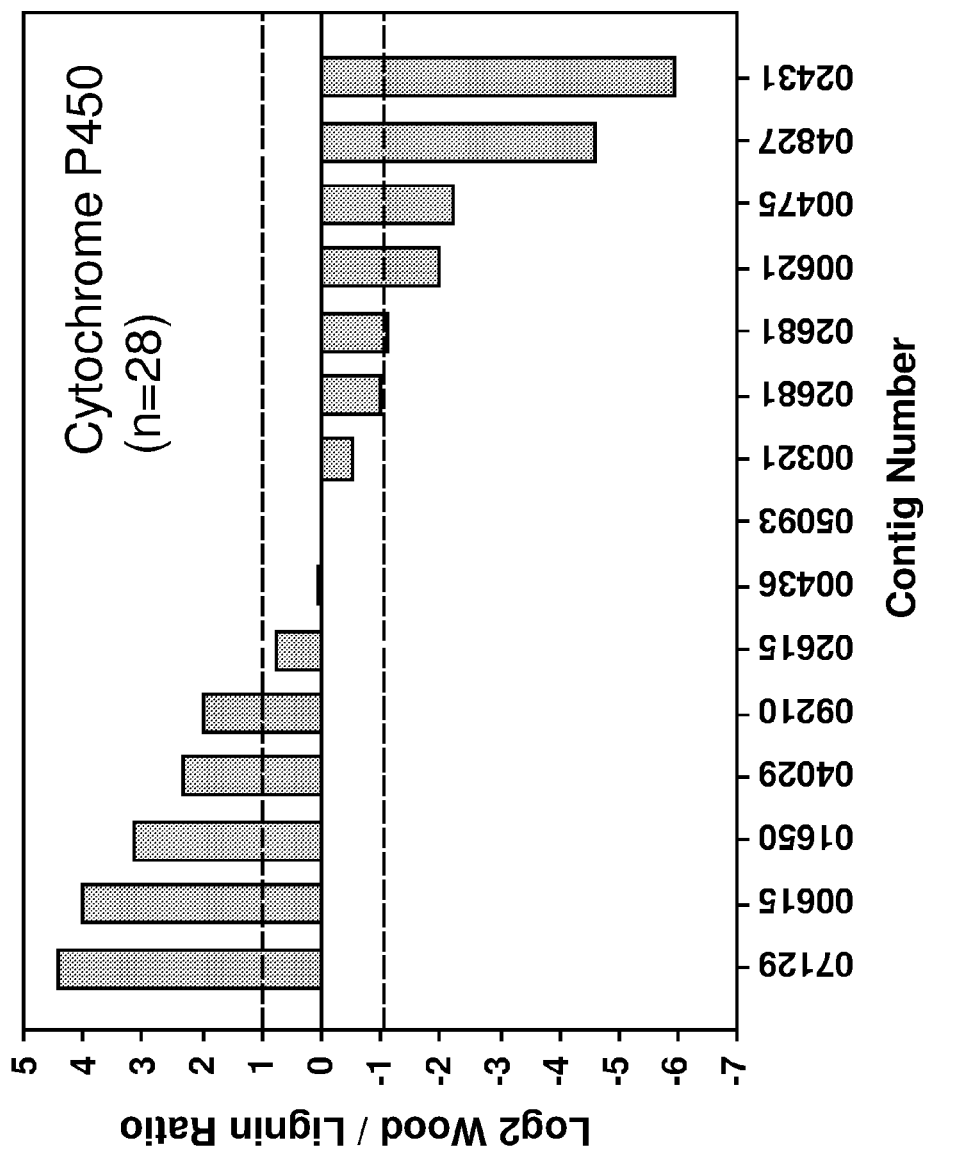
Figure 13C:
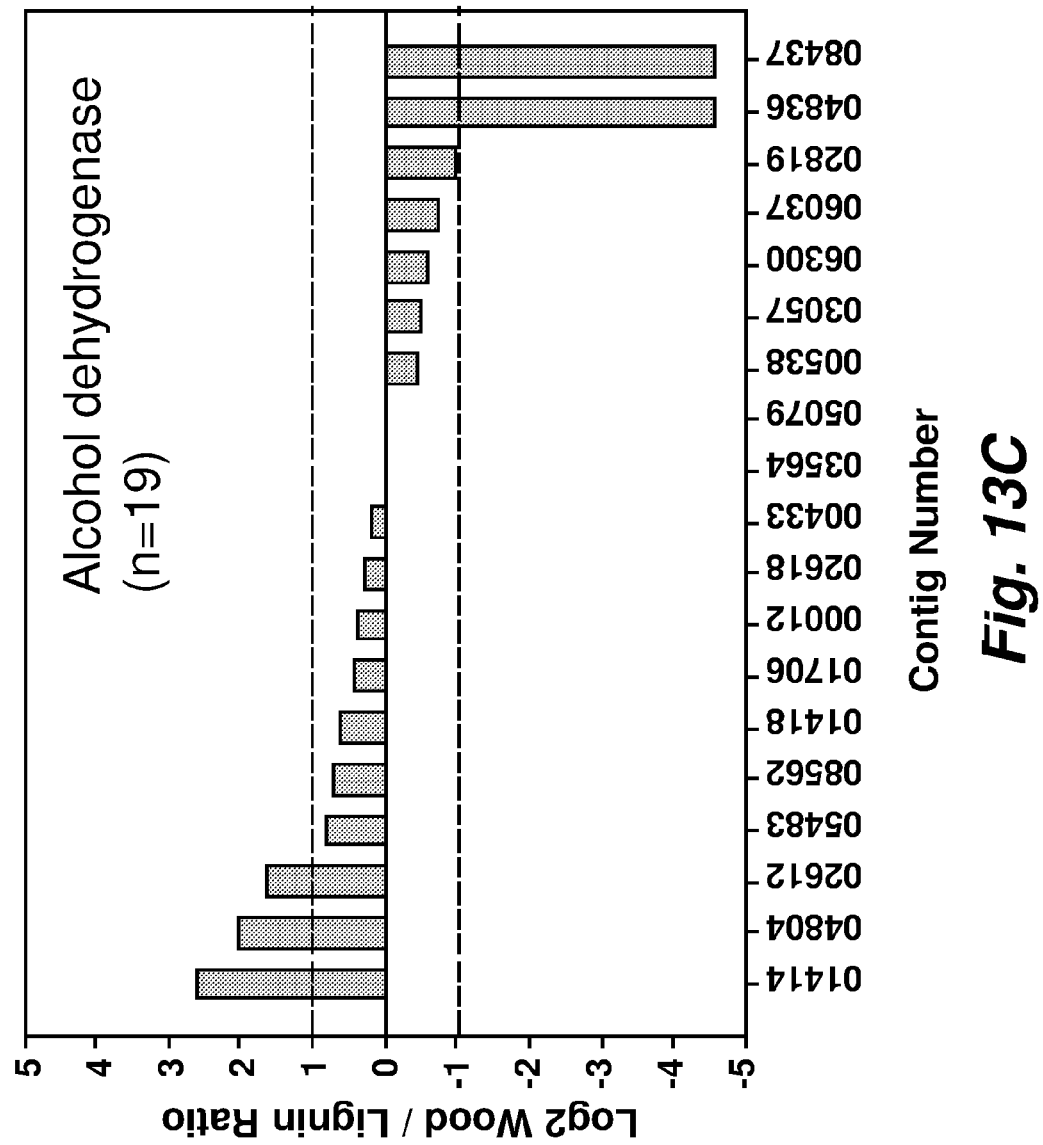
Figure 13D:
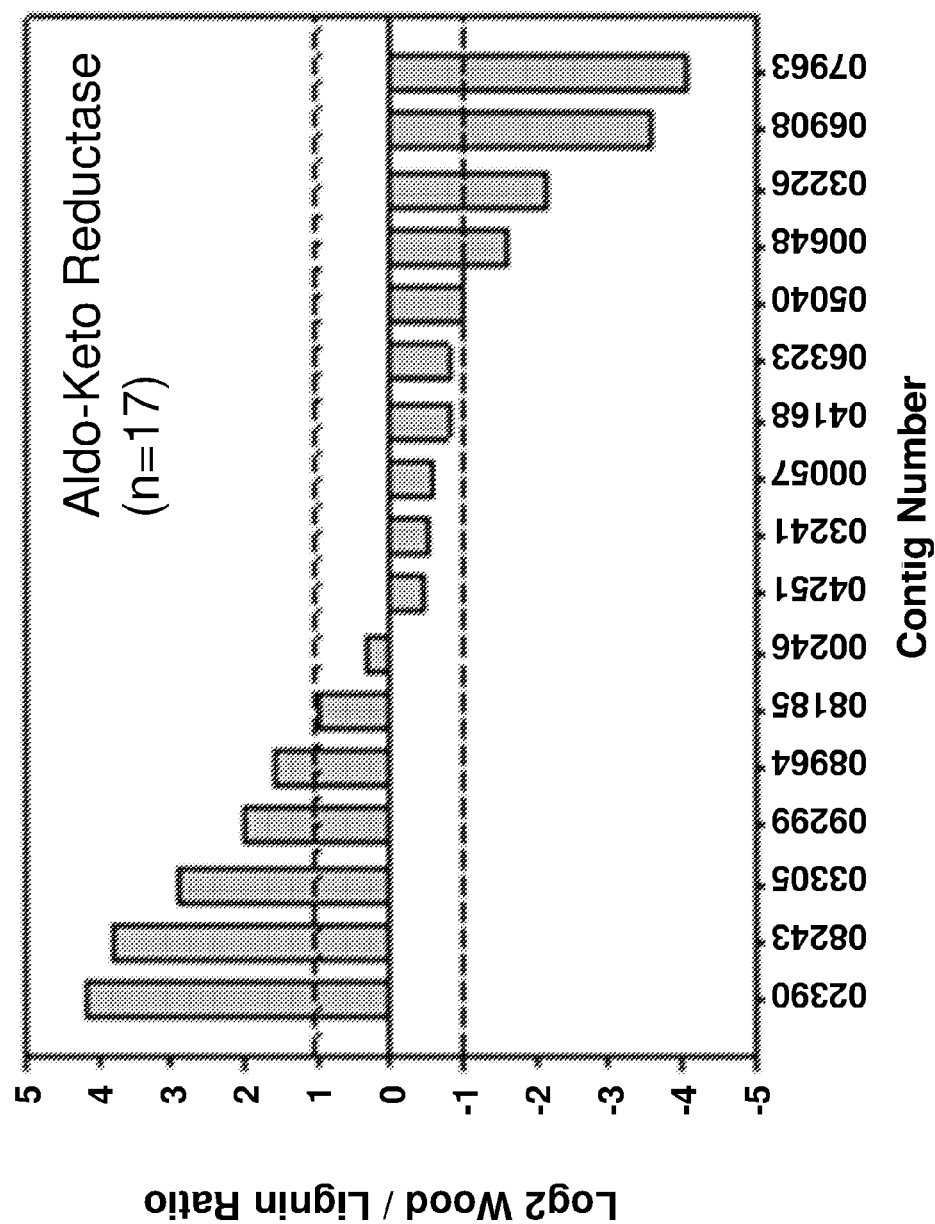
Figure 13F:
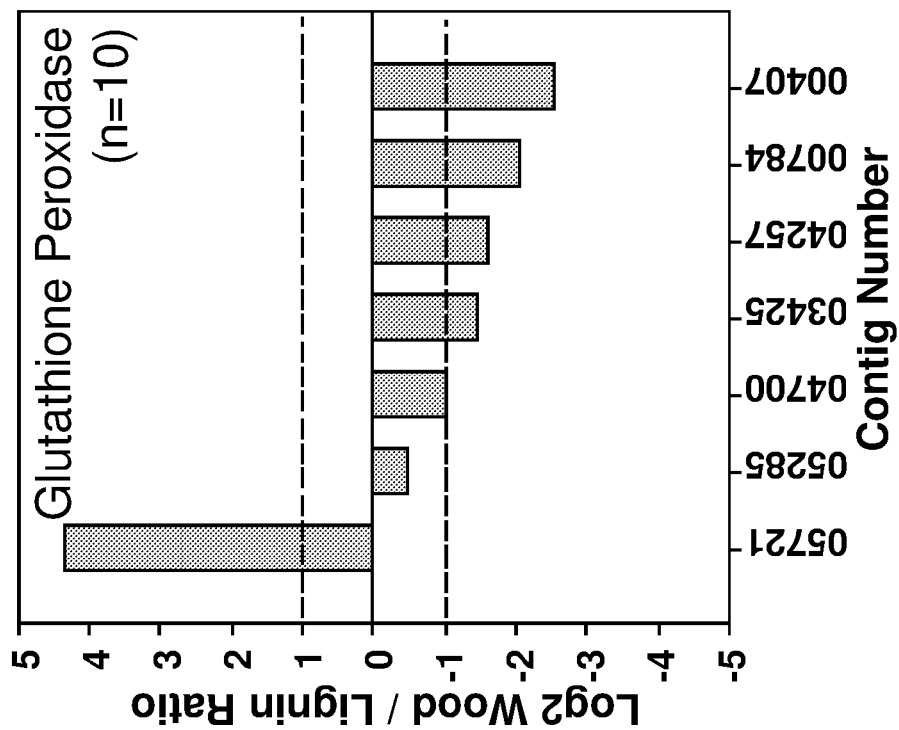
Figure 13E:
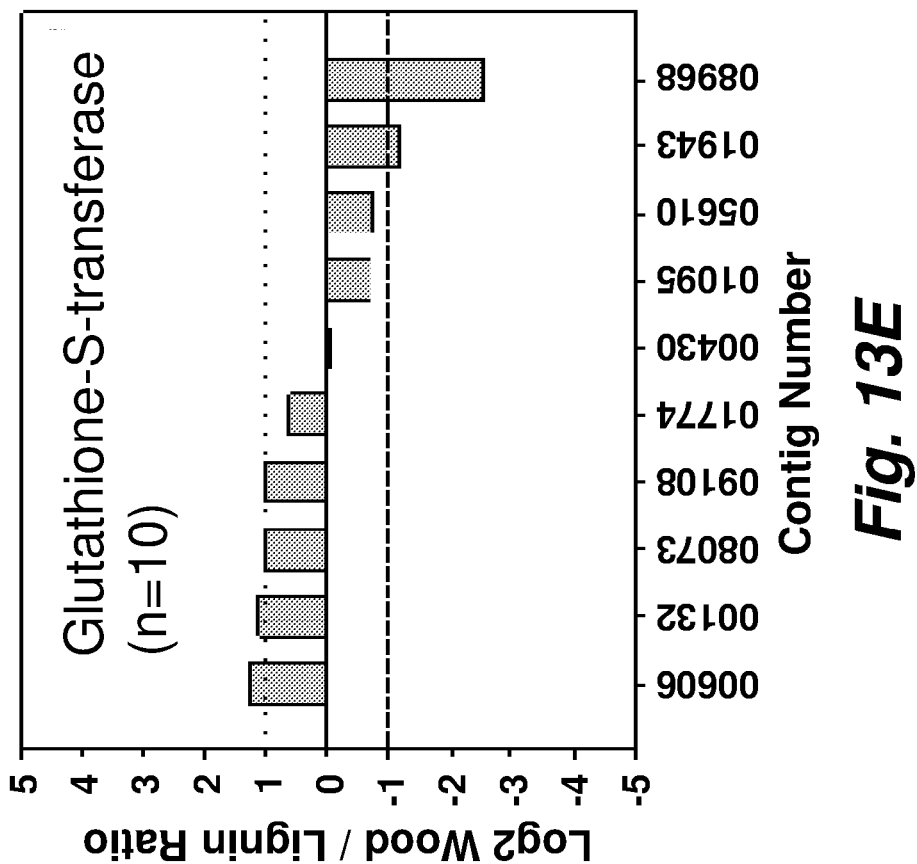
Figure 13I:
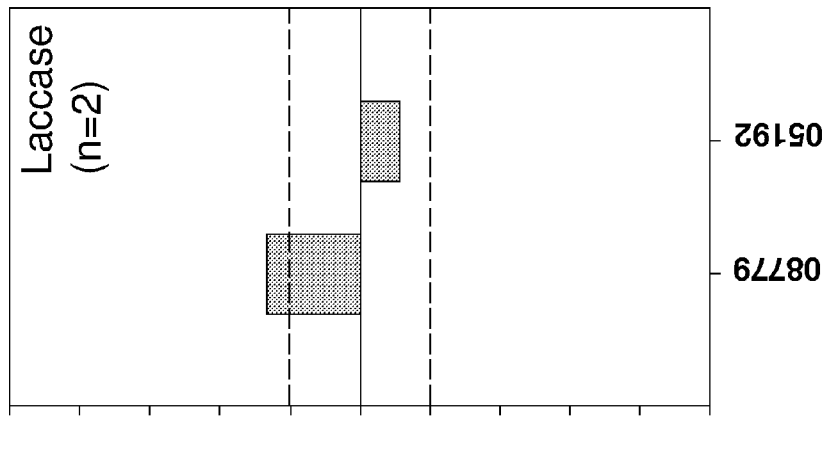
Figure 13H:
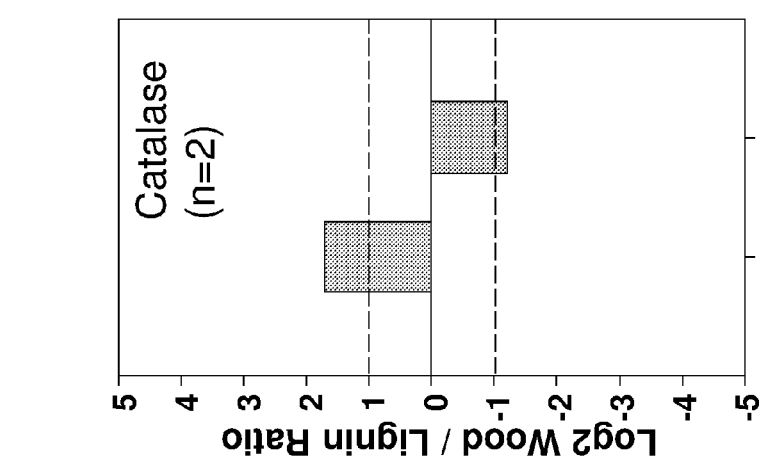
Figure 13G:
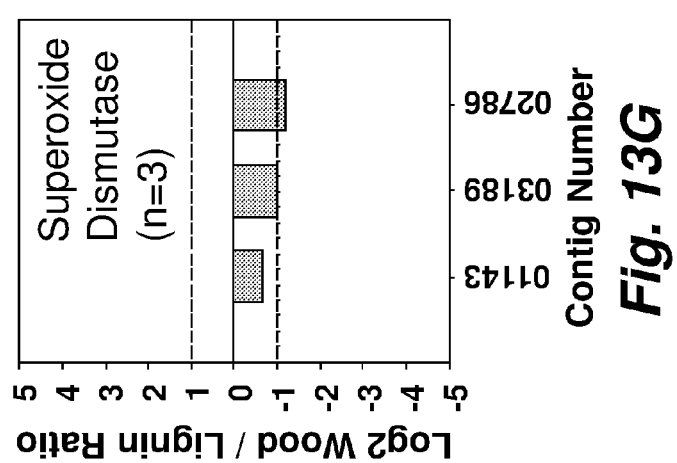
Figure 14A:
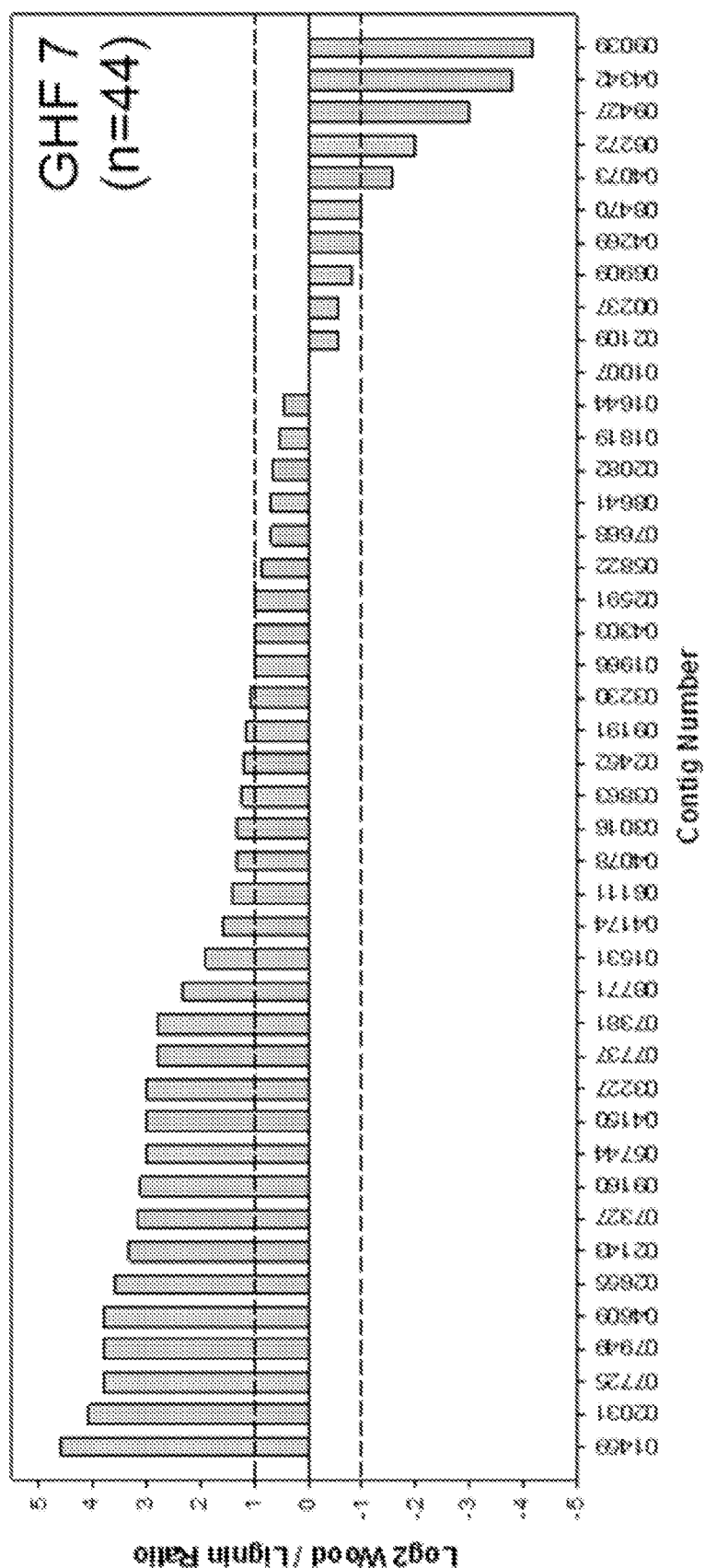
FIGS. 14A-14E provides a series of bar graphs illustrating expression summaries and contig numbers for differentially expressed cellulase genes from GHF families 7 (FIG. 14A), 45 (FIG. 14B), 1 (FIG. 14C), 9 (FIG. 14D) and 2 (FIG. 14E). Bars indicate Log 2 transformed wood library/lignin library expression ratios. Values >1=wood inducible, values <1=lignin inducible, and values between +1 and −1=general phenolic responsive (i.e., shared among both libraries).
Figure 14C:
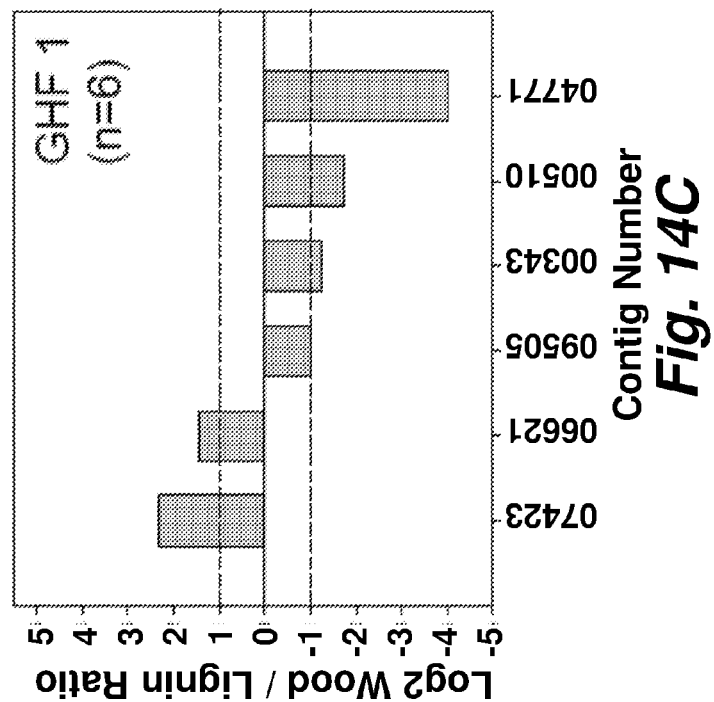
Figure 14B:
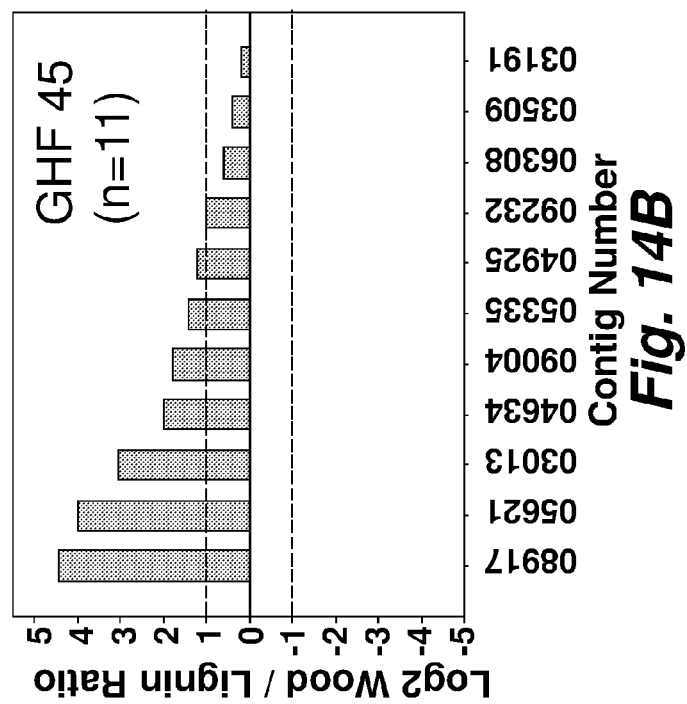
Figure 14E:
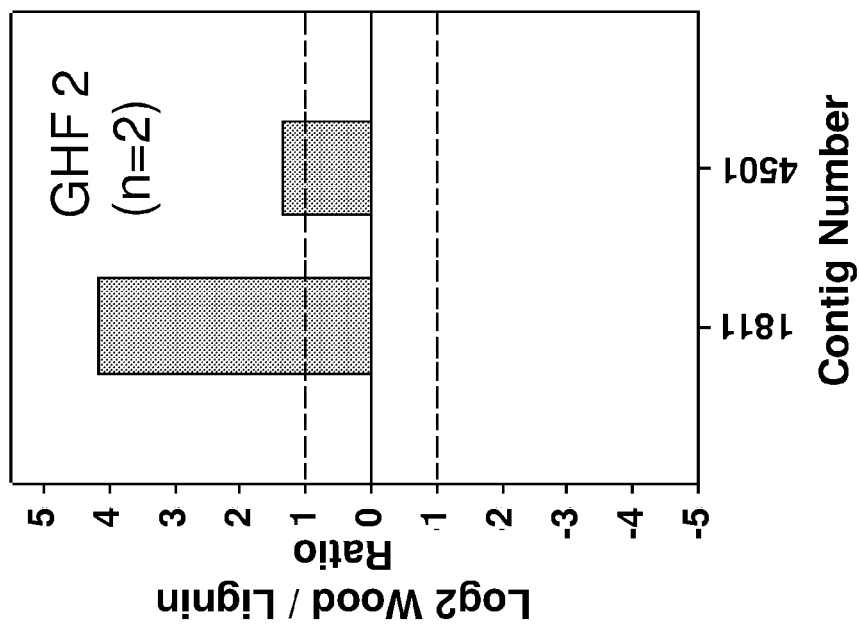
Figure 14D:
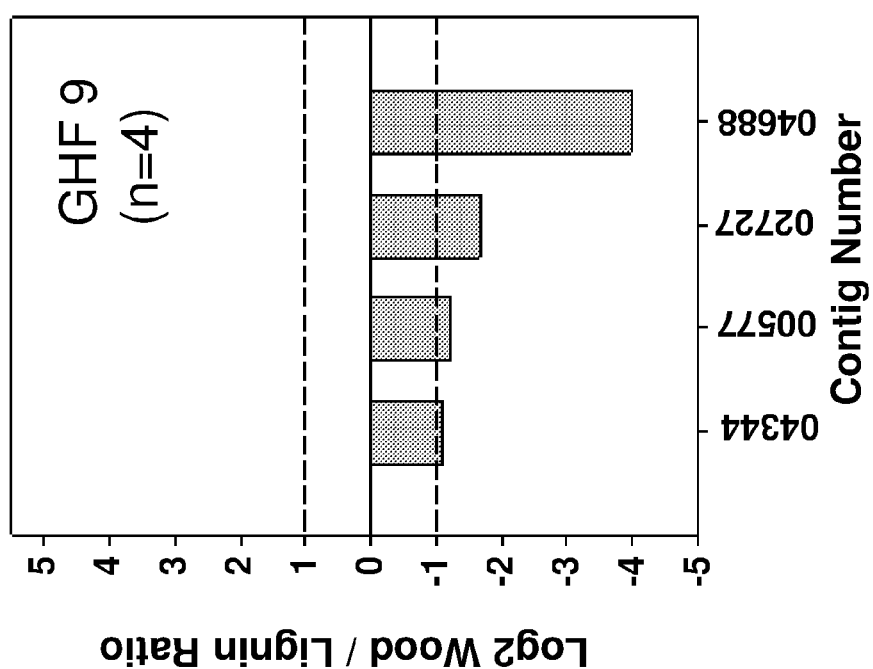
Figure 15A:
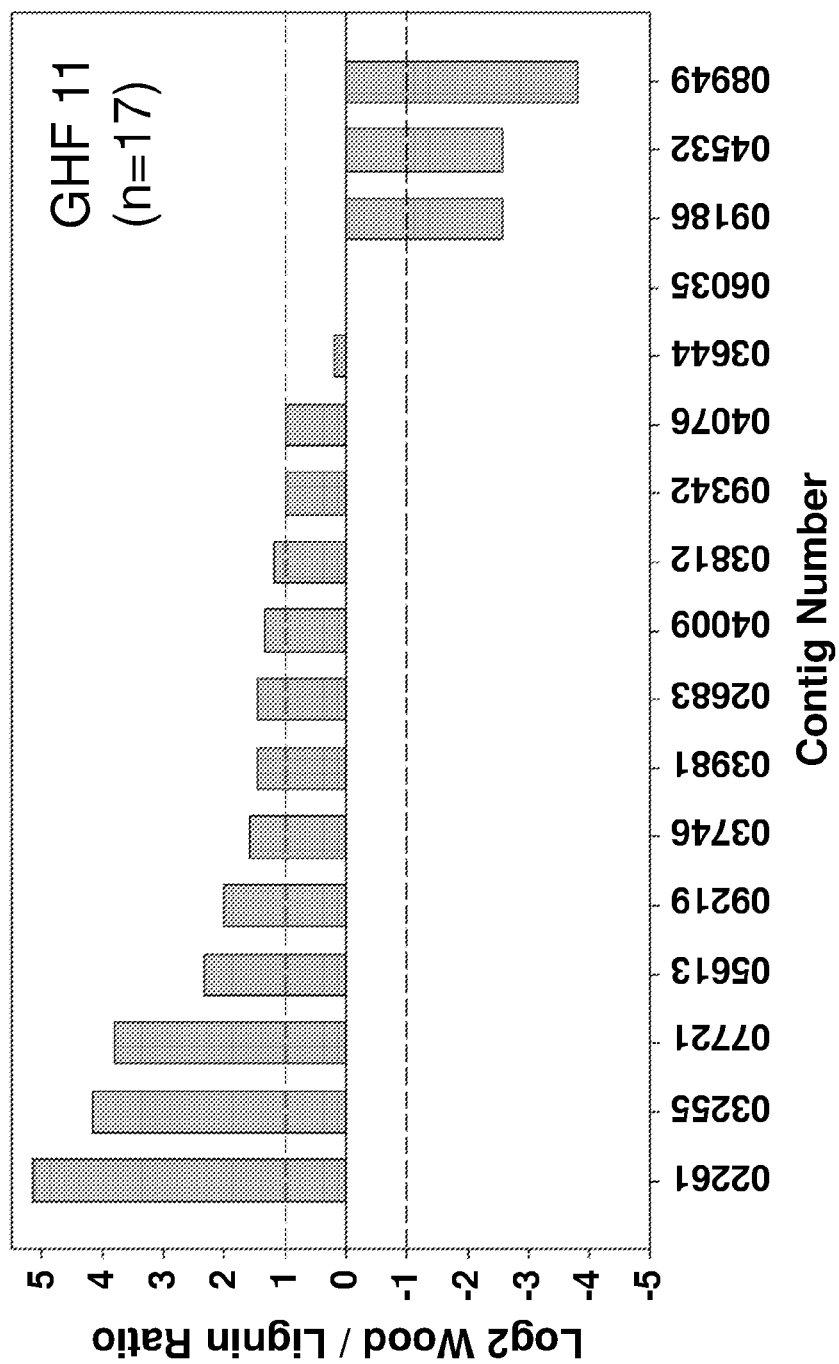
FIGS. 15A-15F provides a series of bar graphs illustrating expression summaries and contig numbers for differentially expressed hemicellulase genes from GHF families 11 (FIG. 15A), 3 (FIG. 15B), 5 (FIG. 15C), 26 (FIG. 15D), 43 (FIG. 15E) and 28 (FIG. 15F). Bars indicate Log 2 transformed wood library/lignin library expression ratios. Values >1=wood inducible, values <1=lignin inducible, and values between +1 and −1=general phenolic responsive (i.e., shared among both libraries).
Figure 15B:
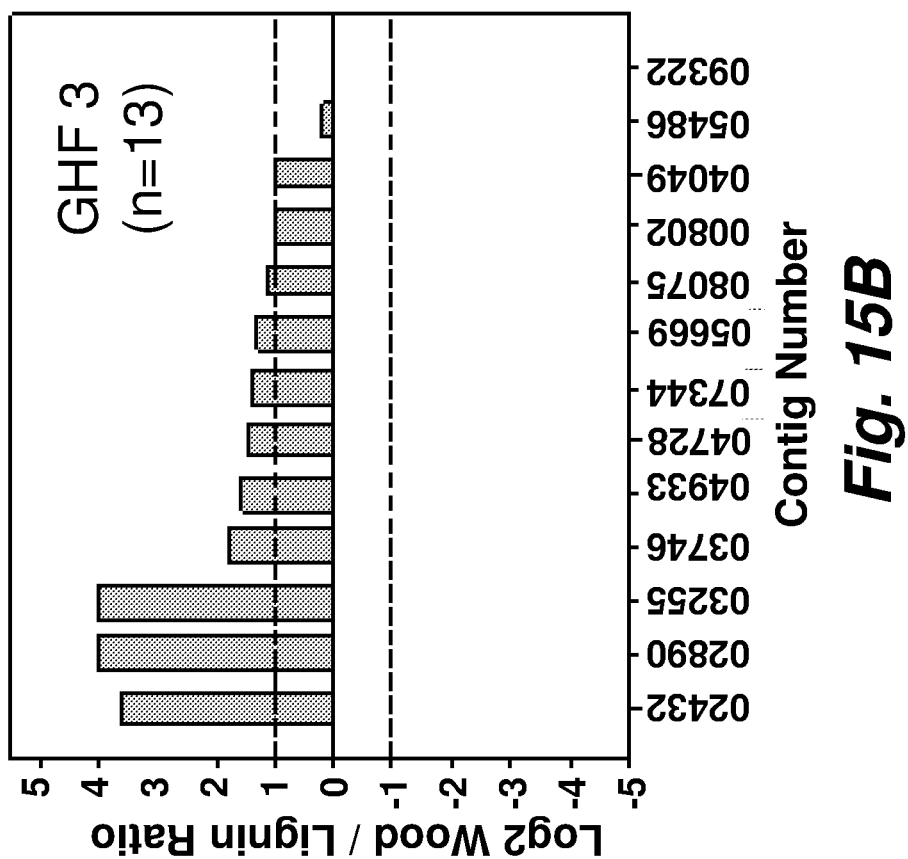
Figure 15D:
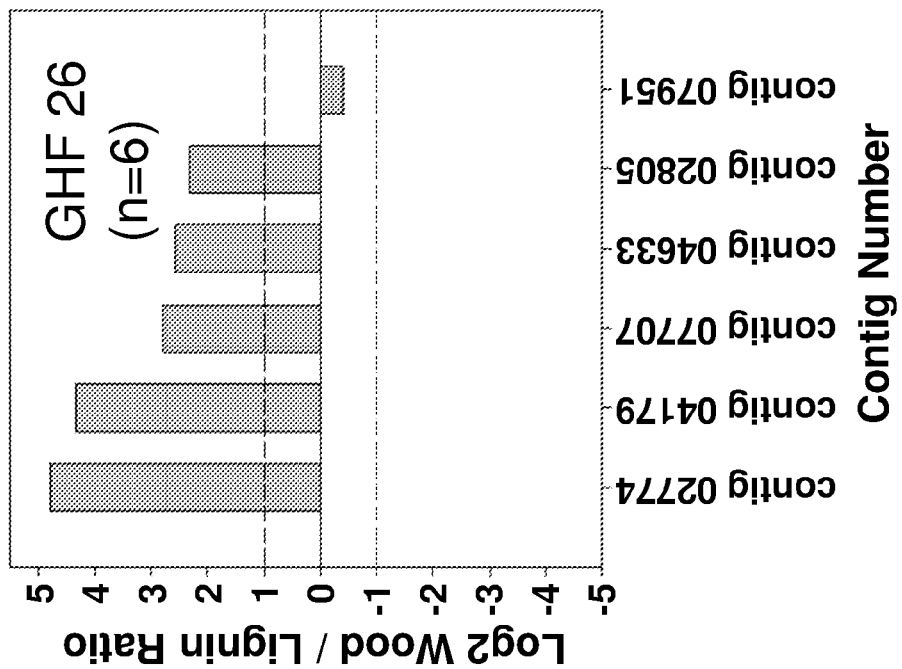
Figure 15C:
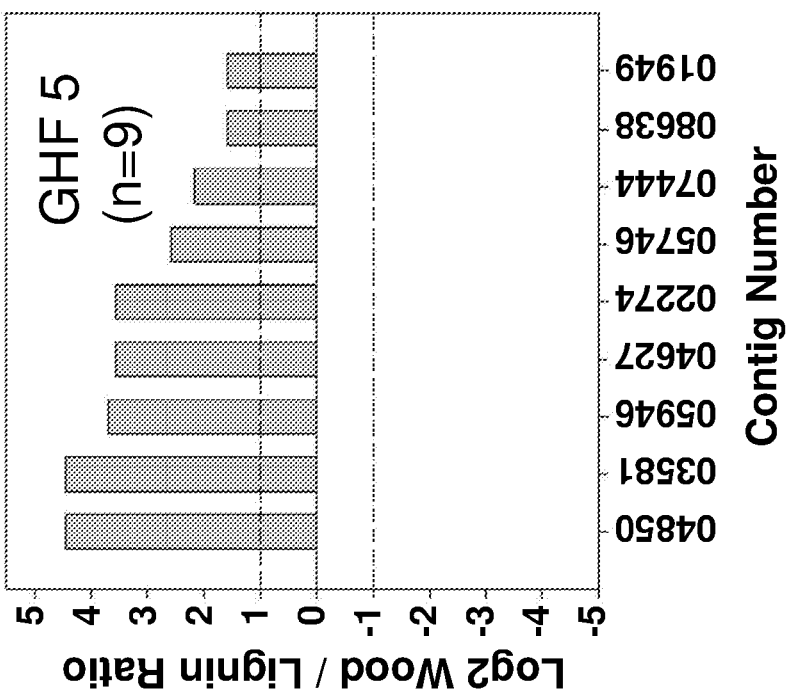
Figures 15E, 15F:
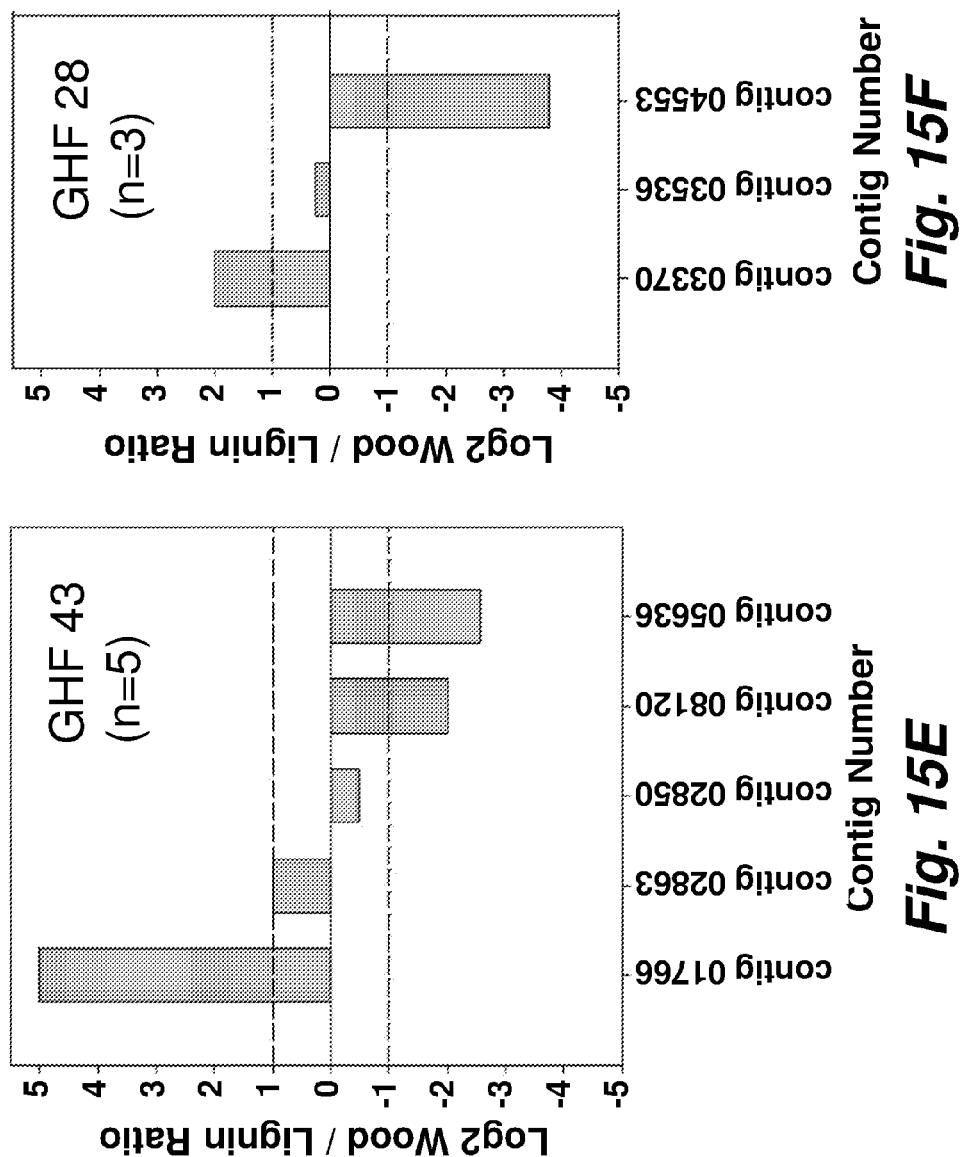
Figure 16:
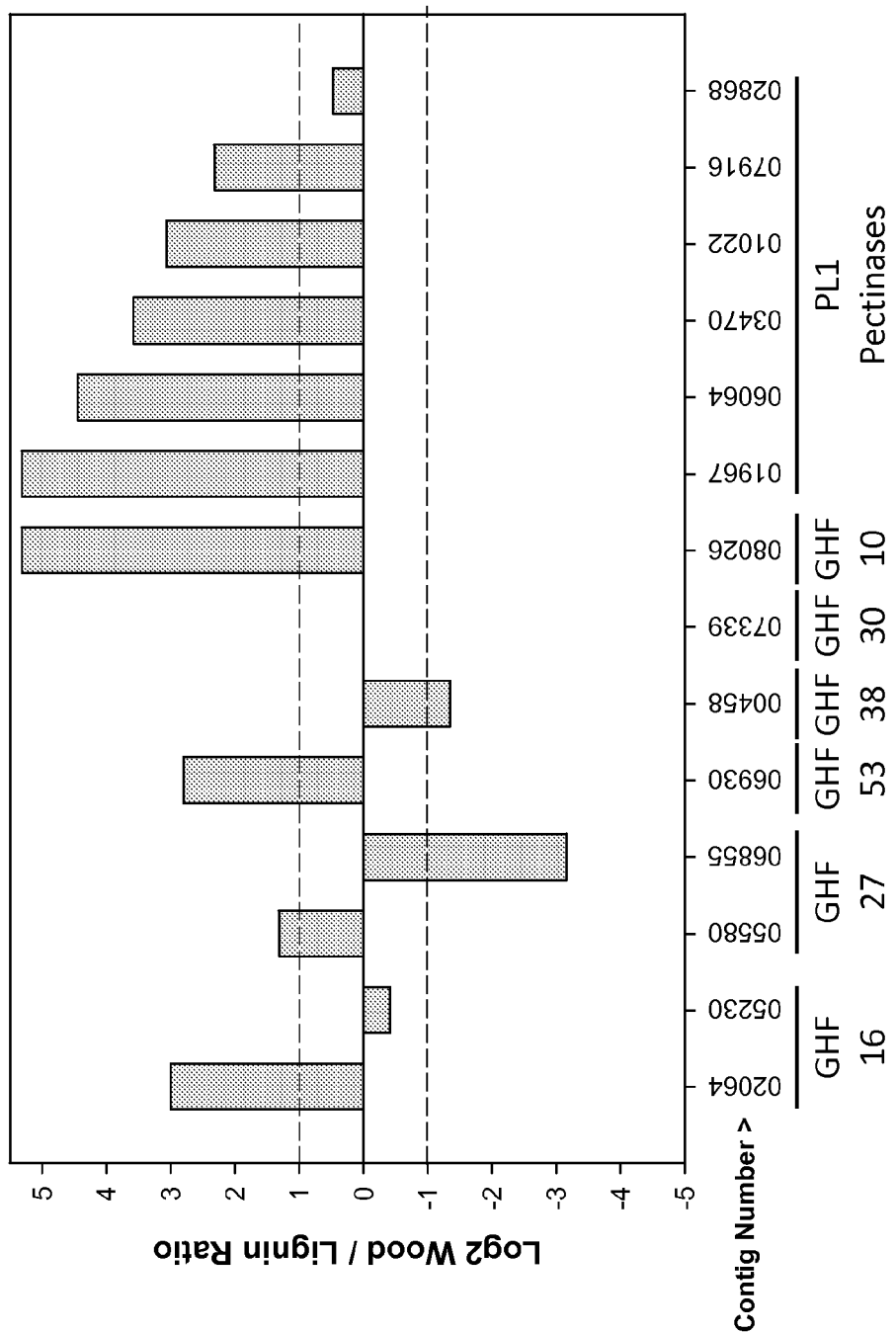
FIG. 16 is a bar graph illustrating expression summaries and contig numbers for differentially expressed hemicellulase and pectinase genes from GHF families 16, 27, 53, 38, 30, 10 and PL1. Bars indicate Log 2 transformed wood library/lignin library expression ratios. Values >1=wood inducible, values <1=lignin inducible, and values between +1 and −1=general phenolic responsive (i.e., shared among both libraries).

A total of 37,243 Gene Ontology (GO) terms were assigned to the combined wood- and lignin-feeding dataset based on BLAST matches to sequences with known function (FIGS. 9A-9C).

GO results for the top 100 most expressed transcripts overall were compared to the top 100 most expressed transcripts from the wood and depolymerized lignin libraries in the three GO categories: cellular location (FIGS. 10A-10D), molecular function (FIGS. 11A-11D) and biological process (FIGS. 12A-12D). There were fewer GO classifications represented in the wood and lignin libraries resulting from all three database searches, suggesting the wood and depolymerized lignin-fed transcript pools are less diverse and more specialized than the general sequence pool. With respect to cellular location, both libraries were enriched in protein complex and membrane-associated GO categories, particularly the wood library, in which nearly half of annotations were membrane associated. This result is consistent with the membrane-bound nature of insect xenobiotic detoxification systems and the idea that lignin and other compounds present in wood are toxic to termites and their gut microbiota.

Molecular function GO searches revealed enriched binding and catalytic capabilities in association with wood and depolymerized lignin feeding. For example, the wood library was enriched for glycosyl hydrolases, which is consistent with the carbohydrate content of wood. Also, the depolymerized lignin library was enriched in oxidoreductase activity, which is consistent with lignin degradation and xenobiotic metabolism requiring oxygen and associated redox systems.

Biological process was the most diverse GO category overall, but again the wood and depolymerized lignin libraries were less diverse than the general "top 100" sequence pool, implying specialization. Most noteworthy of biological process GO searches were phagocytosis-related transcript expression in the wood library and glycolysis-related transcript expression in the lignin library. Phagocytosis is a protist symbiont-associated function that is well documented in association with wood feeding (Cleveland, L. R. (1923) *Proc. Natl. Acad. Sci. USA* 9: 424). Lignin metabolism would likely require more initial energy input and this is suggested by increased synthesis of glycolysis-related proteins such as glyceraldehyde-3-phosphate dehydrogenase and *enolase*. There was also increased production of arginine kinase which is important for energy metabolism in insects.

Example 4

Target Genes (Candidate Lignases and Glycosyl Hydrolases)

In agreement with GO annotations above and predictions resulting from a previous gut digestome EST project (Tartar et al., (2009) *Biotechnol. Biofuels* 2: 25), 262 relevant lignocellulase transcripts were differentially enriched in the two subtracted libraries (96 lignase/detox enzymes and 166 carbohydrate active proteins, as shown in Table 1).

TABLE 1

Summary of differentially expressed transcripts from the lignase/detoxification (n = 96; TOP) and carbohydrate-active (n = 166; BOTTOM) functional categories. Numbers indicate the number of transcript contigs occurring in the wood-fed and lignin-fed libraries, or shared among both libraries (i.e., "general phenolic responsive").

| Functional categories | | Gene family | Wood inducible | Depolymerized lignin inducible | General phenolic responsive | TOTAL |
|---|---|---|---|---|---|---|
| Candidate lignase, antioxidant and detoxification enzymes | | P450 | 7 | 8 | 13 | 28 |
| | | ADH | 3 | 2 | 14 | 19 |
| | | AKR | 5 | 4 | 8 | 17 |
| | | EST | 5 | 5 | 5 | 15 |
| | | GST | 2 | 2 | 6 | 10 |
| | | GSP | 1 | 4 | 2 | 7 |
| | | SOD | | 1 | 2 | 3 |
| | | CAT | 1 | 1 | | 2 |
| | | LAC | 1 | | 1 | 2 |
| | | | total: 24 | total: 25 | total: 47 | 96 |
| Carbohydrate active | Cellulase | GHF 7 | 24 | 15 | 5 | 44 |
| | | GHF 45 | 7 | | 4 | 11 |
| | | GHF 1 | 2 | 1 | 3 | 6 |
| | | GHF 9 | | | 4 | 4 |
| | | GHF 2 | 3 | | | 3 |
| | Hemicellulase | GHF 11 | 10 | 4 | 3 | 17 |
| | | GHF 3 | 10 | 3 | | 13 |
| | | GHF 5 | 9 | | | 9 |
| | | GHF 26 | 5 | | 1 | 6 |
| | | GHF 43 | 1 | 2 | 2 | 5 |
| | | GHF 28 | 1 | 1 | 1 | 3 |
| | | GHF 16 | 1 | 1 | | 2 |
| | | GHF 27 | 1 | 1 | | 2 |
| | | GHF 53 | 1 | | | 1 |
| | | GHF 38 | | 1 | | 1 |
| | | GHF 30 | 1 | | | 1 |
| | | GHF 10 | 1 | | | 1 |
| | Chitinase | GHF 8 | 2 | 1 | | 3 |
| | | GHF 18 | 1 | | | 1 |
| | Ceramidase | GHF 30 | | 1 | | 1 |
| | Pectinase | PL1 | 5 | | 1 | 6 |
| | Amylase | GHF13 | | | 2 | 2 |
| | Laminarinase | GHF17 | | | 3 | 3 |
| | Carbohydrate Binding | CBM2 | 4 | 1 | 1 | 6 |
| | | CBM1 | 1 | | 1 | 2 |
| | | EF Hand | 3 | | 2 | 5 |
| | | Lectin | 1 | 5 | 2 | 8 |
| | | | total: 94 | total: 37 | total: 35 | 166 |

Abbreviations: P450, cytochrome P450;
AKR, aldo-keto reductase;
EST, esterase;
ADH, alcohol dehydrogenase;
GST, glutathione-S-transferase;
SOD, superoxide dismutase;
GSP, glutathione peroxidase;
CAT, catalase;
LAC, laccase;
GHF, glycohydrolase family;
PL, pectin lyase;
CBM, carbohydrate binding module.

The lignase/detox transcripts were distributed across the two libraries (24 wood library, 25 lignin library, and 47 common to both libraries; Table 1). In contrast, glycosyl hydrolase expression profiles were skewed towards the wood library (94 wood library, 37 lignin library, and 35 common to both libraries; Table 1).

Example 5

Lignase & Detox Candidates

Differentially expressed lignase and detox transcripts, identified based on previous studies (Tartar et al., (2009) *Biotechnol. Biofuels* 2: 25; Coy et al., (2010) *Insect Biochem. Mol. Biol.* 40: 723; Scharf et al., *PLoS One* 6, e21709) include cytochrome P450s (P450), esterases (EST), alcohol dehydrogenases (ADH), glutathione-S-transferases (GST), superoxide dismutases (SOD), glutathione peroxidases (GSP), catalases (CAT), and laccases (LAC) (Table 1; FIGS. 13A-13I).

The enrichment of transcripts encoding these enzyme families in the wood and depolymerized lignin-fed libraries strongly indicates that wood and lignin contain xenobiotic constituents that must be detoxified and/or metabolized in the termite gut. P450s are important oxidative xenobiotic-metabolizing enzymes; a total of 28 were enriched among the two subtracted libraries. P450 families represented in order of abundance are Cyp6 (n=13), Cyp4 (8), Cyp9 (2), Cyp12 (2), Cyp15 (2) and Cyp49 (1). These results expand the known number of P450s in *R. flavipes* to over 40 (Zhou et al., (2006) *Insect Mol. Biol.* 15: 749; Tartar, A. et al., (2009) *Biotechnol. Biofuels* 2: 25; Tarver et al., (2010) *BMC Mol. Biol.* 11: 28), which approaches the total number of known P450s in other eusocial insects such as honey bees (Honeybee Genome Sequencing Consortium 2006) and xylophagous leaf-cutter ants (Suen et al., (2010) *PLoS Genetics* 7, e1002007).

Fifteen differentially responsive esterase transcripts were also identified, which supports earlier work suggesting esterases, e.g., ferruloyl esterases, as a potentially relevant family (Wheeler et al., (2010) *Arch. Insect Biochem. Physiol.* 73: 30). Similarly, 39 other antioxidant enzymes from the ADH (19), GST (10), SOD (3), GSP (7) and CAT (2) classes that play important roles in xenobiotic defense were also identified.

Two laccases were also identified, which is in agreement with previous recombinant protein studies showing significant roles by termite gut laccases in catalyzing lignin related phenol-oxidase activity and hemicellulose digestion. One laccase transcript was enriched in each of the two subtracted libraries, the lignin-alkali-associated laccase (contig 05192). These laccase results provide supporting evidence to substantiate the selective feeding approach and use of differential transcript abundance data to identify novel lignase candidates.

Seventeen aldo-keto reductases (AKRs) with differential expression in both libraries were also identified, as shown in Table 1. The AKRs are known to act on lignin and other phenolic byproducts in ligno-cellulolytic yeast (Kuhn et al., (1995) *Appli. Environ. Microbiol.* 61: 1580; Ford et al., (2001) *Chem Biol. Interact.* 685: 130-132). With 448 total reads, one AKR was the 18$^{th}$ most highly expressed transcript identified (contig 00057), had 1.6-fold higher expression in the lignin library, and its protein product increased with lignin feeding, indicating that AKR plays important physiological roles in the termite gut, and more specifically, in lignin/phenolic metabolism. Additionally, 126 novel candidate lignase and associated cofactor transcripts were discovered based on 56 microbial lignase literature references and related sequence databases. These additional auxiliary enzymes include: 54 dehydrogenases, 18 oxidases, 4 peroxidases, 1 transhydrogenase, 13 reductases, 5 hydratases, 9 hydrolases, 2 dioxygenases, 4 hydroxylases, 2 thiolases, 5 synthetases and 13 redoxins.

Example 6

Transcripts Encoding Carbohydrate-Active Enzymes

Three categories of carbohydrate-active transcripts were differentially expressed among the wood and depolymerized lignin libraries, as shown in Table 1 and FIGS. 14A-14E, 15A-15F, and 16, specifically: glycosyl hydrolases (cellulases, hemicellulases, chitinases, ceramidase, amylases and laminarinases); carbohydrate binding proteins (carbohydrate binding, EF hand, and lectin); and pectin lyases. Many (57%) of differentially expressed carbohydrate active transcripts (94 of 166) were enriched in the wood library. Surprisingly, some (21%) of carbohydrate active transcripts (35 of 166) were enriched in the depolymerized-lignin library.

Hemicellulase-coding GH transcripts would likely be enriched when paper (cellulose)-associated transcripts were subtracted from the wood- and lignin-fed libraries. Indeed, transcripts matching hemicellulases from glycosyl hydrolase families (GHF) 11, 3, 5, 26, 43 and 28 were most abundant in the wood library. However, protist symbiont cellulases from GHF 7 and 45 were also enriched in the wood library, in part supporting previous predictions that protist GH enzymes are required to degrade more recalcitrant cellulose forms and/or play dual roles in cellulose and hemicellulose depolymerization.

Chitinases (GHF 8 and 18) were also enriched in the wood-fed library, possibly in association with termite defense against wood-associated fungi that contain chitin polymers as a component of their cell walls.

In the depolymerized lignin library, enriched GHF transcripts included cellulases from GHF 7, 45, 1 and 9, and hemicellulases from GHF 11, 26, 43 and 28. Two *R. flavipes* cellulases from GHF 1 and 9 have been functionally characterized: the Cell-1 cellulase from GHF9 and β-glu beta glucosidase from GHF1 (Zhou et al., (2007) *Gene* 395: 29; Zhou et al., (2010) *Arch. Insect Biochem. Physiol.* 74: 147; Scharf et al., (2010) *Insect Biochem. Mol. Biol.* 40: 611). These are both endogenous host enzymes with high expression in symbiont-free salivary gland tissue; recombinant forms of both enzymes were found to act synergistically in saccharification of complex lignocellulose and hemicellulose substrates.

Interestingly, induction of GHF members by depolymerized lignin (a non-carbohydrate phenylpropanoid-derived material) suggests that termites and their gut symbiota compensate for phenol-associated lignocellulose recalcitrance by producing more cellulases. In this respect, the results support that a rich pool of symbiont cellulases is produced to maximize release of available sugars and provide metabolic energy to overcome the lignin barrier.

While not wishing to be bound by any one hypothesis, as initially suggested by functional studies with a recombinant laccase, cellulase and β-glucosidase, and supported by the current transcriptomic findings, host cellulases appear to be part of a detoxification pathway in which free sugars released from cellulose/hemicellulose are conjugated to toxic mono-lignols released from lignin. The latter "conjugative detoxification" hypothesis would transform the view of host-symbiont collaboration in termite lignocellulose digestion (because it would indicate that host cellulases play broader roles in detoxification of lignin by-products, in addition to their stereotypical roles in cellulose digestion and nutrition).

Example 7

Proteomics

Proteomics was used to determine lignin-feeding impacts at the post-translational level. For this purpose, depolymerized lignin and cellulose feeding assays occurred under identical conditions as described above for pyrosequencing. After bioassays, soluble gut protein fractions were subjected to 2D SDS-PAGE, followed by LC-MS/MS analysis. In this analysis, the focus was on soluble proteins and, therefore, mitochondrial and microsomal protein fractions having membranous detoxification enzymes such as P450s were excluded.

Several depolymerized lignin-inducible proteins were identifiable by comparison to (1) the pyrosequencing database resulting from the present study, and (2) an existing termite gut EST database. Ten differentially expressed proteins were identified, including: aldo-keto reductase, profilin, ELF-1, G3P dehydrogenase, arginine kinase, Cell-1 endoglucanase (apparent multimers and degradation products), pyruvate phosphate dikinase, thaumatin, angiotensin converting enzyme, and cyclophilin.

Among the proteins identified by homology searches, the most differentially expressed protein was aldo-keto reductase (AKR) (contig 00057). This lignin-induced AKR was chosen for further study because AKRs can be oxidative detoxification enzymes involved in the metabolism of phenolic compounds like those found in lignin.

Figure 19:
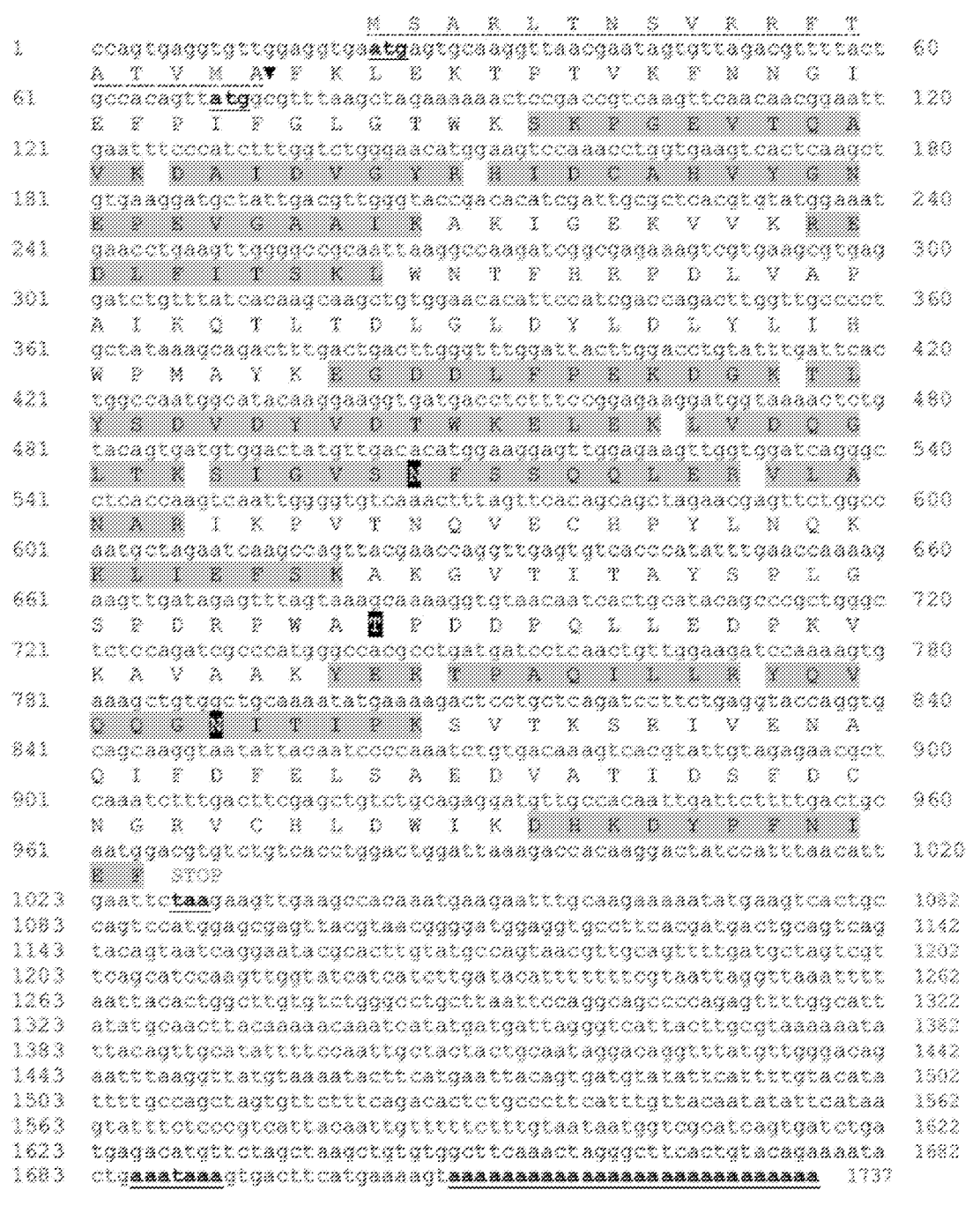

The nineteen sequenced AKR peptides ((SEQ ID NOS.: 1-19) as shown in FIG. 17B) match to the translated AKR cDNA sequence (SEQ ID NO.: 21) from the present pyrosequencing work (Table 1, contig 00057 in FIG. 13D) and to a translated R. flavipes cDNA library we published previously (Tartar et al., (2009) Biotechnol. Biofuels 2: 25) (FIG. 18). The translated AKR cDNA (SEQ ID NO.: 21) is shown in FIG. 19 along with sequenced peptide alignments.

There are two predicted translational initiation sites in the AKR cDNA sequence (SEQ ID NO.: 20). The first translational initiation site would produce a protein of 37.9 kDa with pI of 6.46, and the second site would produce a protein of 36.1 kDa with pI of 5.72. The estimated molecular weight and pI values for the AKR peptides in 2D SDS-PAGE gels ranged from 35.5-35.6 kDa and 5.45-5.79, respectively. Thus, it is likely that the second translational initiation site is used.

In silico signal peptide analysis predicted that this AKR does not have a secretion signal peptide, and protein targeting analysis indicates that this AKR is cytoplasmic. These results, therefore, do not suggest that AKR is secreted into the termite gut lumen to interact directly with lignin.

These proteomics findings are significant because they (1) emphasize AKRs as a potentially important family of expressed termite lignocellulases, and (2) show congruence at the transcription and translational levels. The latter result further validates the use of a selective feeding bioassay approach for identification of novel termite lignocellulases.

Example 8

Functional Studies with Recombinant Enzymes

Two host cellulases, Cell-1 and β-glu, whose transcripts were found to be inducible, were shown in previous recombinant enzyme studies to act synergistically in the saccharification of various lignocellulose substrates (Scharf et al., 2011). Also, another inducible transcript identified in the current study, the LacA laccase, was previously found to metabolize lignin phenolic compounds and enhance saccharification of hemicellulose when tested in combination with Cell-1 and β-glu. These results, which initially established that the host transcripts Cell-1, β-glu and LacA play significant digestive roles in the termite gut, are strengthened by the findings of the present disclosure.

Using a modified experimental design that compared wood vs. cellulose feeding, a digestome microarray study has identified a number of the same wood-responsive enzyme-encoding transcripts as the current study; for example, AKR, P450, CAT, EST, GST, SOD, GPX, LAC, GHF7 and GHF11 (Table 1). Based on the combined microarray and current pyrosequencing results, four novel recombinant enzymes were generated and tested in combination with Cell-1 [contig 00577], β-glu [contig 00343] and LacA [contig 05192].

These novel enzymes included a protozoan symbiont GHF7 cellulase (GHF7-3 [contig 00237]), a GHF11 endo-xylanase (GHF11-1 [contig 03644]), a catalase (CAT [contig 01463]), and the aldo-keto reductase noted above (AKR [contig 00057]). Histidine-tagged recombinant enzymes were each engineered into recombinant baculoviruses and expressed in Trichoplusia ni larvae after oral infection.

Construct Generation, Recombinant Protein Production, and Purification:

Recombinant proteins were produced in whole Trichoplusia ni larvae using the PERLXpress procedure described previously (Kovaleva et al., (2009) Biotechnol. Letts. 31: 38, incorporated herein by reference in its entirety). For the Lacasse A, C-terminal tags composed of two glycine and six histidine residues, as well as XbaI and EagI restriction sites, were incorporated into target gene amplicons utilizing the primers shown in Table 2.

TABLE 2

| Primer | Target | PCR Primer Sequence[a] |
|---|---|---|
| 1 | Laccase A (LacA)-forward | 5'-tctagaATGTTGCCTTG CGTCCTGCTTG-3' (SEQ ID NO.: 36) |
| 2 | Laccase A (LacA)-reverse | 5'-cggccgTTAGTGATGAT GGTGATGATGacctccGTTG GTGTTCACGGGAGGTGT-3' (SEQ ID NO.: 37) |
| 3 | AKR-forward | 5'-tctagaATGAGTGCAAG GTTAACGAATAGTG-3' (SEQ ID NO.: 25) |
| 4 | AKR truncated-forward | 5'-tctagaATGGCGTTTAA GCTAGAAAAA-3' (SEQ ID NO.: 55) |
| 5 | AKR-reverse | 5'-cggccgTTAGTGATGAT GGTGATGATGacctccGAAT TCAATGTTAAATGGATAGTC CTTG-3' (SEQ ID NO.: 26) |
| 6 | GHF7-3 forward | 5'-GATCAGATCTTAATCAG GATTTCACCTACAC-3' (SEQ ID NO.: 56) |
| 7 | GHF7-3 reverse | 5'-GATCGGTACCATAAGTG CTATCAATCGGAC-3' (SEQ ID NO.: 57) |

[a]XbaI and EagI sites are underlined in primers 1-5; BglII site underlined in primer 6; KpnI site underlined in primer 7 (SEQ ID NO.: 57; start and stop codons are indicated in bold; His-6 and Gly-2 encoding regions are italicized.

The nucleotide sequences encoding catalytically active GHF11, AKR, and CAT were generated by oligonucleotide synthesis in their entireties and inserted in the expression vector. The GHF7-3 gene was PCR-amplified from the a full-length clone TS51-B10 using primers (see Table 2) introducing Bgl II (forward) and Kpn I (reversed) sites for the cloning of the GHF7-3 gene lacking native signal sequence into a pre-made vector comprising viral signal sequence derived from gp64 envelope protein gene and further including a thrombin-cleavable C-terminal His-tag.

The PCR amplicons or synthetic polynucleotides, including encoded ORF cDNA sequences of target proteins, plus the C-terminal Gly-His tag (for Laccase A), were cloned into the XbaI-EagI sites of the pVL1393 transfer vector, and recombinant baculoviruses were generated using a homologous recombination system in insect Sf9 cells. pVL1393 was used only for cell-1 and laccase A insertion and expression; pBacPAK8 and 9 were used for the catalase, AKR, GHF7-3 and GHF11-1; pFastBac1 was used for βGlu expression.

Plasmid TS51-B10 was used as a template for GHF7-3 amplification. The sequence was not complete, lacking the N-terminal signal sequence and no ATG. Using alignments to several sequences from GenBank it was deduced that 16 nucleotides were likely missing. The gene was expressed with the viral signal sequence, because the complete native signal sequence was unknown.

To confirm protein expression after viral infection, Sf9 cultures were screened by western blotting using an anti-His-specific monoclonal antibody (Novagen, Madison, Wis.). Active viral lines were identified as described previously (Kovaleva et al., (2009), herein incorporated by reference in its entirety) and subsequently injected into *T. ni* larvae for large-scale protein production.

Recombinant protein was recovered from clarified *T. ni* homogenates to near homogeneity, as described previously (Coy et al., (2010) *Insect Biochem. Mol. Biol.* 40: 723; Scharf et al., (2010) *Insect Biochem. Mol. Biol.* 40: 611; Zhou et al., (2010) *Arch. Insect Biochem. Physiol.* 74: 147, each of which is herein incorporated by reference in its entirety) by tandem Ni-IMAC (nickel-immobilized metal affinity chromatography) followed by buffer exchange with Sephadex G-25 chromatography. Protein storage buffer consisted of 0.1 M sodium acetate, 0.15 M sodium chloride, 5 mM calcium chloride, and 5 μM copper sulfate (pH 5.8). Laccase purity was assessed by SDS-PAGE with Coomassie staining and western blotting with anti-His tag antibody. All protein concentrations were determined using a microplate Bradford assay (Bio-RAD; Hercules, Calif.).

Recombinant proteins were used directly in pine sawdust digestion assays with glucose detection following an established protocol. Xylose detection was performed using a commercial D-Xylose assay (Megazyme; Wicklow, Ireland).

(1) The recombinant Cell-1 and β-glu combination liberated significant glucose release relative to negative controls that lacked enzyme, and (2) addition of the LacA laccase caused no significant increase in glucose release from pine lignocellulose, as shown in FIG. 2. For three-enzyme cocktails that included Cell-1 and β-glu plus AKR, CAT or GHF7-3, non-significant (about 1.5-3-fold) increases in glucose release occurred. However, four-enzyme cocktails that included either AKR or CAT plus all three cellulases (Cell-1, β-glu and GHF7-3) significantly increased glucose release by more than 3.5-fold relative to Cell-1 and β-glu alone. Three- and four-enzyme cocktails that included LacA had slightly reduced glucose output relative to identical reactions without LacA. As expected, GHF11-1 did not significantly enhance glucose release when tested alone and in combination against pine lignocellulose; however, GHF11-1 did catalyze significant xylose release from pine lignocellulose, as shown in FIG. 3. Additionally, after a 4-hr pre-incubation period with the LacA laccase, GHF11-1 liberated significantly greater xylose release presumably as a result of LacA-mediated lignin disassociation (FIG. 3). These results show that three non-cellulase enzymes identified through our selective feeding and quantitative pyrosequencing approach (AKR, CAT and LacA) significantly enhance lignocellulose saccharification by host and symbiont cellulases and hemicellulases, including in the termite gut.

Example 9

Bioassays and 1D-PAGE Analysis

Figure 20:
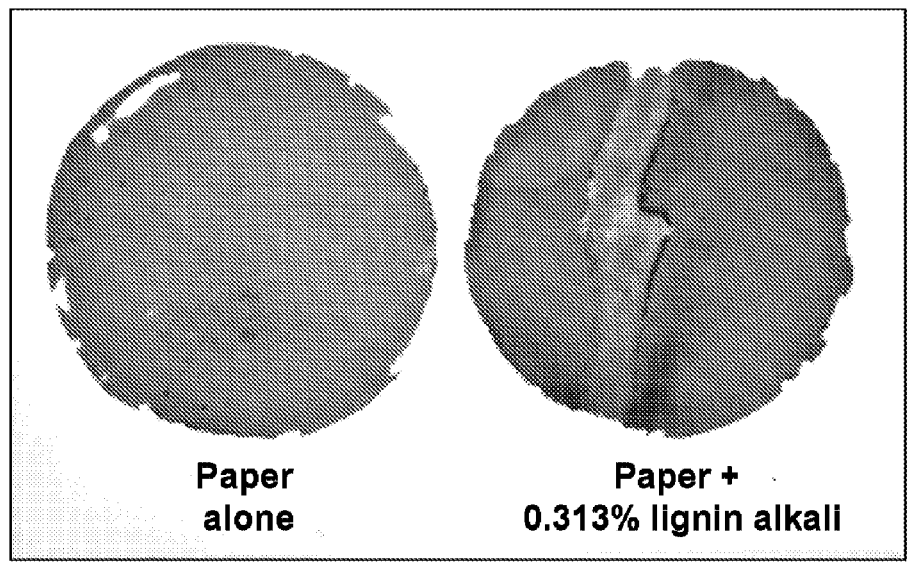
FIG. 20 is a digital image illustrating filter paper feeding by groups of 50 worker termites over 7-day assays (left: paper alone; right: paper+lignin alkali).

Bioassays were conducted with 50 worker termites (*R. flavipes* colony K9) on Whatman #1 filter papers in 50 mm diameter Petri plates. Two treatments were tested: 98% cellulose paper alone and paper+0.313% lignin alkali (Sigma-Aldrich #471003). This concentration was tested based on previous results showing significantly increased gut phenol-oxidase activity after feeding on filter paper+ 0.313% lignin alkali (Tartar et al., (2009) *Biotech. Biofuels* 2: 25). The lignin alkali solution was prepared in water and adjusted to pH 7.4 with acetic acid. After 7 days, considerable feeding occurred on both substrates, as shown in FIG. 20. A surface-feeding pattern was seen in the lignin treatment, which is consistent with "gnawing pheromone" activity elicited by the phenolic compound hydroquinone seen in *Reticulitermes* termites (Reinhard et al., (2002) *J. Chem. Ecol.* 28: 1). Over 90% survival occurred in both treatments.

Figure 21:
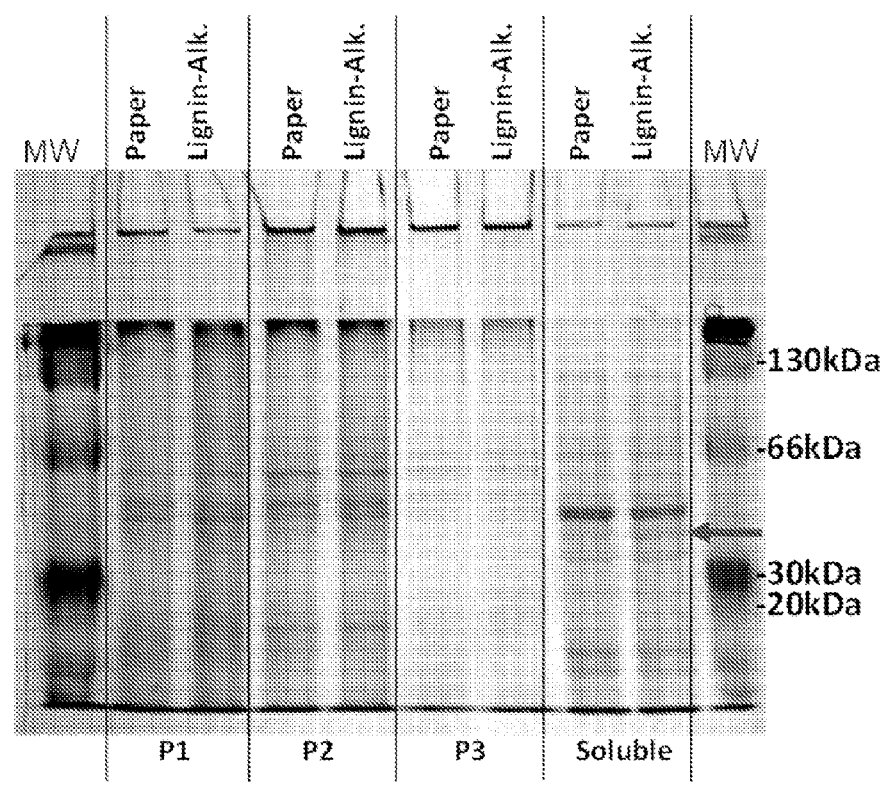
FIG. 21 is a digital image illustrating a one-dimensional SDS-PAGE analysis (10% acrylamide, 1% SDS) of different gut protein fractions with GEL-CODE BLUE® staining. MW: molecular weight markers; P1: 1,000×g nuclear pellet; P2: 10,000×g mitochondrial pellet; P3: microsomal pellet precipitated at 10,000×g in the presence of 8 mM calcium chloride); Soluble: soluble fraction remaining after precipitation of P1, P2 and P3 pellets; kDa: kilodaltons; ←: differentially expressed approximately 35 kDa protein band in the soluble lignin alkali fraction.

Next, whole guts were isolated from all surviving termites, placed in sodium acetate buffer (0.1 M, pH 7) and homogenized using a glass-glass Tenbroeck tissue grinder. Nuclear and mitochondrial fractions were pelleted by centrifugation at 1,000×g and 10,000×g, respectively, and the microsomal fraction pelleted at 10,000×g in homogenization buffer+8 mM calcium chloride (Kupfer & Levine (1972) *Biophys. Biochem. Res. Comm.* 47: 611). All protein fractions from both treatments were assessed for protein content by standard Bradford protein assays. Protein quality was assessed by one-dimensional SDS-PAGE, as shown in FIG. 21. Some differences in mitochondrial and soluble protein composition among treatments were observable, particularly in the range of about 35 kDa in the soluble supernatant fraction.

Example 10

2D-PAGE Analysis

The soluble gut supernatant fractions (FIG. 21, right) were subjected to 2D PAGE analysis as follows:

(a) Protein Preparation for CyDye Labeling:

One ml of gut-soluble protein mixture in 0.1 M sodium acetate pH 7 with 8 mM calcium chloride, from either paper- or lignin-fed termites, was precipitated with 9 volumes of ice cold 10% TCA/acetone overnight at −20° C. The resulting protein pellet was recovered by centrifugation at 20,000 g for 20 min at 4° C. and was washed twice with 80% ethanol then was washed twice with 80% acetone. The protein pellet was air-dried on ice for 5 min and was dissolved in DIGE labeling buffer (8M urea 2M thiourea, 4% CHAPS, 20 mM Tris pH 8.5, 0.2% SDS). Benzonase (Novagen) was added to each dissolved extract to digest large molecules of nucleic acid. The resulting solution was then clarified at 40,000 g for 30 min at 15° C. before protein quantification assay. Protein concentration was determined using EZQ® protein quantification kit (Invitrogen) and ovalbumin as standard.

(b) CyDye Labeling:

Protein labeling with CyDye was modified and performed according to Friedman et al., (2004) *Proteomics* 4: 793-811, using commercially available CyDye technology (GE Healthcare). After adjusting sample solution to pH 8.5, each protein sample was covalently linked to a different CyDye fluorophore, such as Cy2 to reference sample mixture (a mixture of equal amount of protein extracts from both paper and lignin), Cy3 to paper, and Cy5 to lignin. In each case 100 μg of protein was labeled with 400 pmol CyDye for 30 min in darkness on ice. Excess dye was quenched with 1 μl of 10 mM lysine.

(c) 2-D Gel Electrophoresis:

All three different CyDye labeled samples were mixed together with 200 μg of unlabeled mixed sample and increased to 500 µl with IEF buffer (8 M urea, 2M thiourea, 4% CHAPS, 100 mM DDT, 0.2% SDS, 0.5% IPG, buffer pH 3 to 11) before passively rehydrating a 24 cm IPG no-linear gradient strip (pH 3 to 11; GE Healthcare). Labeled proteins in the strip were focused at 19° C. on an IPGphor3 Unit (GE Healthcare) with voltage ramping up to and held at 10,000 Volt for a total 100 kVh. After IEF, the strip was first equilibrated with reducing buffer (50 mM Tris-HCl pH 6.8, 6 M Urea, 30% glycerol, 2% SDS, 100 mM DTT), then equilibrated with alkylation buffer (50 mM Tris-HCl pH 6.8, 6 M Urea, 30% glycerol, 2% SDS, 2.5% iodoacetamide). Both equilibration steps were held at room temperature in darkness for 15 min. After equilibration, the strip was transferred and mounted on top a 24×24 cm, 8 to 16% Tris Glycine polyacrylamide gel (Jule) under a layer of warm 0.5% agarose made in SDS electrophoresis running buffer. Electrophoresis was carried out in Ettan Daitsix Unit (GE Healthcare) at 12° C. at 10 mA/gel for one hr, and then overnight at a constant current of 12 mA/gel and a limit of 150 V until the dye front reached the bottom of the plate.

Figure 22:
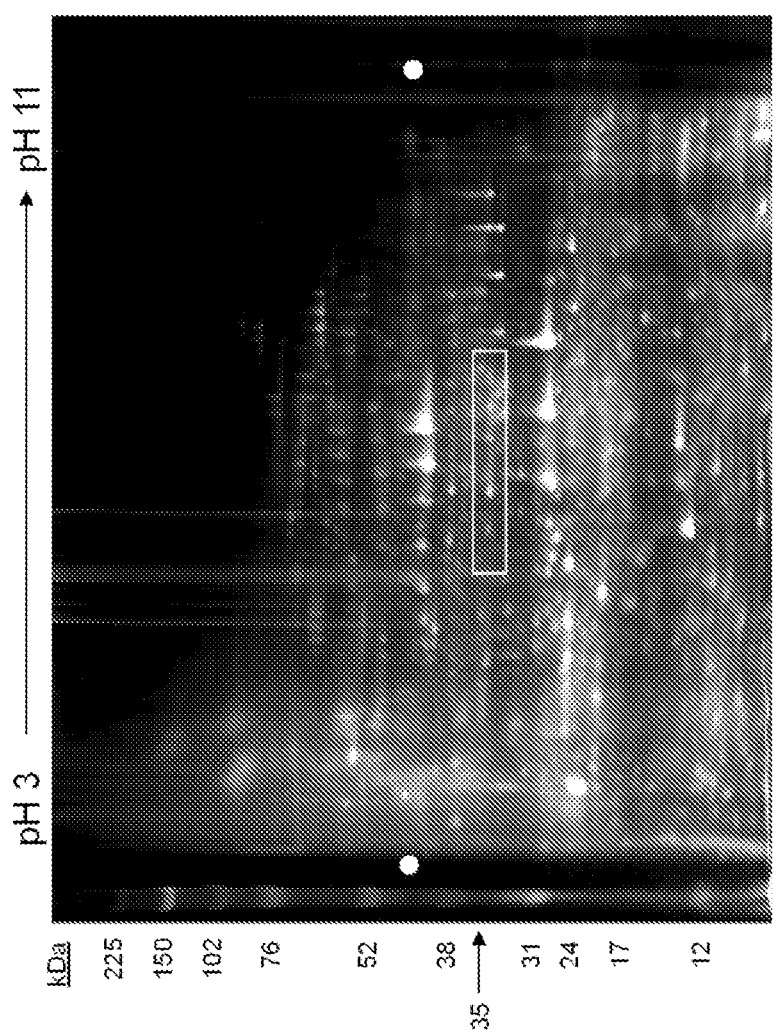
FIG. 22 is a digital image illustrating a two-dimensional separation of the soluble gut protein fraction with two-color imaging to show differentially expressed proteins. The strongest lignin alkali-up-regulated proteins are enclosed in the box

Because the paper and lignin alkali samples were labeled, respectively, with Cy3 (green) and Cy5 (red) dyes, this enabled two-color quantification on single gels as shown, for example, in FIG. 22.

With this approach, green labeled protein spots are up-regulated with paper diet, red labeled spots are up-regulated with lignin diet, and yellow spots are identical between diets. 2D PAGE revealed several candidate lignin-inducible proteins; however, the most prominently up-regulated protein spots had molecular masses near 35 kDa and pI values in the 2-5 range (see box in FIG. 22).

Example 11

Peptide Expression Analysis and Spot Picking

Methods of peptide expression analysis and spot picking are as follows:
Image Acquisition and Data Analysis:

Immediately after gel electrophoresis, CyDye labeled proteins in gels were scanned using a Typhoon 9400 Variable Mode Imager (GE Healthcare). The excitation/emission wavelengths for Cy2, Cy3 and Cy5 were 488/520, 532/580 and 633/670 nm, respectively. Three images (internal standard, paper-fed, and lignin-fed) were acquired. The digital image information acquired was then analyzed with DeCyder 2D software, version 7.0 (GE Healthcare). All spots present in all images in the gel were co-detected, matched, and normalized with the DIA (Differential In-Gel Analysis) Module within the software. There were over 2000 spots detected and matched. Interesting spots were selected by setting the fold difference threshold to 1.5-fold. Specifically, any protein spot from the lignin sample that was expressed above or below 1.5-fold when compared with the identical spot from the paper sample was selected. A pick list was made and the ordinance information obtained from DeCyder software for each interesting protein spot was transferred to an automated ProPic spot picker (Genomic Solutions) using the pick list. The spots then were excised by the picker and transferred to a collecting plate and were used for protein identification as described in the following section.

Over 2000 protein spots were identifiable on 2D gels. Twenty-three spots with greater or less than 2-fold induction or repression in the lignin treatment were selected for robotic spot picking, as shown in FIG. 17A, and subsequent MS/MS analysis. Three spots with similar expression were also selected as controls (#1834, 627 and 628).

Example 12

Protein Identification

Methods for protein identification were as follows:
(a) Protein Identification by LC-MS/MS:

Protein identification was performed by LC-MS/MS. Trypsin-digested samples were injected onto a capillary trap (LC Packings; PepMap Inc.) and desalted for 5 min with a flow rate of 3 µl/min of 0.1% v/v acetic acid. The samples were loaded onto an LC PACKING® C18 Pep Map nano-flow HPLC column. The elution gradient of the HPLC column started at 3% solvent A, 97% solvent B and finished at 60% solvent A, 40% solvent B for 30 min. Solvent A consisted of 0.1% v/v acetic acid, 3% v/v ACN, and 96.9% v/v $H_2O$; Solvent B consisted of 0.1% v/v acetic acid, 96.9% v/v ACN, and 3% v/v $H_2O$.

LC-MS/MS analysis was carried out on a LTQ ORBIT-RAP XL® mass spectrometer (Thermo Scientific). The instrument, under control of Xcalibur 2.07 with LTQ Orbitrap Tune Plus 2.55 software, was operated in the data-dependent mode to automatically switch between MS and MS/MS acquisition. Survey scan MS spectra (from m/z 300-2000) were acquired in the orbitrap with resolution R=60,000 at m/z 400. The five most intense ions were sequentially isolated and fragmented in the linear ion trap by collision-induced dissociation (CID) at a target value of 5,000 or maximum ion time of 150 ms. Dynamic exclusion was set to 60 secs. Typical mass spectrometric conditions include a spray voltage of 2.2 kV, no sheath and auxiliary gas flow, a heated capillary temperature of 200° C., a capillary voltage of 44V, a tube lens voltage of 165V, an ion isolation width of 1.0 m/z, a normalized CID collision energy of 35% for MS2 in LTQ. The ion selection threshold was 500 counts for MS2. An activation q=0.25 and activation time of 30 ms were set.

(b) Protein Search Algorithm:

All MS/MS spectra were analyzed using Mascot (Matrix Science, London, UK; version 2.2.2). Mascot was set up to search *R. flavipes* gut and symbiont EST databases (Genbank Accession Nos. FL634956-FL640828 and FL641015-FL645753) and termite gut 454 contig data sets (present study), assuming the digestion enzyme trypsin. Mascot was searched with a fragment ion mass tolerance of 0.50 Da and a parent ion tolerance of 15 ppm. The iodoacetamide derivative of Cys, deamidation of Asn and Gln, and oxidation of Met are specified in Mascot as variable modifications. Scaffold (version Scaffold-02-03-01, Proteome Software Inc.) was used to validate MS/MS-based peptide and protein identifications. Peptide identifications were accepted if they could be established at greater than 95.0% probability as specified by the Peptide Prophet algorithm. Protein identifications were accepted if they could be established at greater than 99.0% probability and contained at least 2 identified unique peptides. Protein probabilities were assigned by the Protein Prophet algorithm.

Results:

In total, 26 protein spots were selected for analysis, as shown in Table 3. Four spots could not be identified because of limited quantities (#1650, 2890, 1641 and 1607). Several differentially-expressed proteins were identifiable by comparison to existing termite gut EST database (Tartar et al. (2009) Biotech. Biofuels 2: 25) and pyrosequencing database (present study). The differentially-expressed proteins identified included: (1) aldo-keto reductase, (2) profilin, (3) ELF-1, (4) G3P dehydrogenase, (5) arginine kinase, (6) Cell-1 endoglucanase (apparent multimers and degradation products), (7) pyruvate phosphate dikinase, (8) thaumatin, (9) angiotensin converting enzyme, and (10) cyclophilin.

both of the cellulose-subtracted, wood and lignin-alkali libraries. However, while present in both libraries, the AKR sequence was encountered 1.6-fold more frequently in the lignin alkali library (270 lignin alkali library, 178 wood library). Also, with 448 total reads, the AKR transcript was

TABLE 3

Protein identities as determined by tandem MS analysis of trypsin-digested protein spots. Identifications were by comparison of peptide fragments to translated termite gut and symbiont EST and 454 pyrosequencing databases. Aldo-keto reductases highlighted in italics

| spot # | Identity | Spot No. | Abundance | Lignin/paper (Cy5/Cy3) spot Volume Ratio | Max Volume | pI | Mass (kDa) |
|---|---|---|---|---|---|---|---|
| 1 | ?? unknown | 1650 | Increased | 5.71 | 473559 | 5.54 | 37482 |
| 2 | *aldo-keto reductase (contig 572)* | *1820* | *Increased* | *5.72* | *2525836* | *5.45* | *35599* |
| 3 | Profiling | 3190 | Increased | 4.44 | 3827247 | 6.59 | 7157 |
| 4 | ELF-1 | 2310 | Increased | 4.41 | 763914 | 8.75 | 22078 |
| 5 | Profiling | 3218 | Increased | 3.98 | 3917813 | 8.11 | 6874 |
| 6 | *aldo-keto reductase (contig 572)* | *1829* | *Increased* | *3.67* | *11104035* | *5.62* | *35491* |
| 7 | G3P dehydrogenase | 1747 | Increased | 3.42 | 1357365 | 6.73 | 36508 |
| 8 | G3P dehydrogenase | 1837 | Increased | 3.41 | 3336722 | 5.76 | 35408 |
| 9 | G3P dehydrogenase | 1791 | Increased | 3.23 | 1206698 | 6.73 | 35946 |
| 10 | ?? unknown | 2890 | Increased | 3.07 | 1923337 | 4.02 | 11748 |
| 11 | ?? unknown | 1641 | Increased | 2.68 | 525509 | 5.45 | 37614 |
| 12 | Arginine kinase | 1707 | Increased | 2.62 | 415012 | 5.52 | 36814 |
| 13 | Cell-1 | 3091 | Increased | 2.56 | 3581093 | 4.64 | 8447 |
| 14 | Pyruvate phosphate dikinase 2 | 1746 | Increased | 2.46 | 439945 | 5.41 | 36319 |
| 15 | thaumatin | 2590 | Increased | 2.38 | 2682508 | 3.91 | 17512 |
| 16 | Cell-1 | 1835 | Increased | 2.28 | 2800085 | 6.21 | 35436 |
| 17 | *aldo-keto reductase (contig 572)* | *1834* | *Similar* | *2.24* | *3575686* | *5.79* | *35463* |
| 18 | Hex-2 | 627 | Similar | 1.73 | 851046 | 5.9 | 69062 |
| 19 | Hex-2 | 628 | Similar | 1.67 | 661848 | 5.9 | 69201 |
| 20 | ?? unknown | 1607 | Decreased | −2.32 | 2394470 | 3.88 | 36111 |
| 21 | Angiotensin converting enzyme | 475 | Decreased | −2.38 | 413431 | 4.9 | 93824 |
| 22 | Cell-1 | 2147 | Decreased | −2.43 | 20546481 | 6.43 | 27850 |
| 23 | Cell-1 | 2259 | Decreased | −2.46 | 13142836 | 5.39 | 23318 |
| 24 | Cyclophilin | 2996 | Decreased | −2.66 | 2582515 | 8.64 | 9925 |
| 25 | Cell-1 | 469 | Decreased | −2.68 | 307876 | 4.85 | 93824 |
| 26 | Cell-1 | 2145 | Decreased | −2.78 | 17425842 | 6.43 | 27850 |

While other proteins, as noted in Table 3, may ultimately prove to be relevant to lignocellulose digestion, the efforts here focused on the aldo-keto reductases (AKRs). Specifically, two AKR peptides (spots 1820 and 1829) had the highest lignin alkali induction of around about 5-fold, and a third AKR peptide was up-regulated 2.24-fold by lignin alkali. The 19 sequenced AKR peptides (SEQ ID NOS.: 1-19), as shown in FIG. 17B, are a near-full-length match for a full-length cDNA (SEQ ID NO.: 20) sequenced previously from a R. flavipes host gut cDNA library (FIG. 18) (contig 572; Tartar et al., (2009) *Biotech. Biofuels* 2: 25). The translated AKR cDNA is shown in FIG. 19, along with sequenced peptides. The predicted mass for the full-length amino acid sequence is 37.8 kDa with a pI=6.2; whereas, the predicted mass and pI of the sequence encoded from the second start codon are 36 kDa and 5.7, respectively. The mass and pI values for the sequenced protein spots ranged from 35.5-35.6 kDa with pI values of 5.45-5.79; thus, it is likely that the native protein sequence begins at the second methionine start codon.

The same AKR transcript was also obtained through quantitative pyrosequencing efforts (contig 00057) from the eighteenth most highly sampled transcript in the pyrosequencing study. Such high gut expression levels indicate the AKR protein to be physiologically important. Indeed, AKRs are enzymes with established links in the literature to metabolism of phenolic compounds such as those that occur in lignin.

Example 13

β-glu cellulase gene RfBGluc was PCR-amplified from the clone (GenBank FL635576; ADK12988.1) using the following primers: forward, 5'-<u>GTCGAC</u>ATGAGGTTACAGACGGTTTGC-3' (SEQ ID NO.: 58) (Sal1 sites underlined, start codon shown in bold); reverse, 5'-<u>CTGCAG</u>TTAGTGATGATGGTGATGATGG-TCTAGGAAGCGTTCTGGAA-3' (SEQ ID NO.: 59) (Pst1 site underlined, stop codon shown in bold and 6× histidine-coding nucleotides italicized). The PCR amplicon encoded the full-length RfBGluc ORF sequence (amino acids 1 to 495) and 6× histidine tag at the C-terminus and was cloned into Sal1-Pst1 sites of Bac-to-Bac transfer vector pFastBac1.

Baculovirus was prepared using Bac-to-Bac system in Sf9 cells according to manufacturer protocol and injected into *Trichoplusia ni* larvae.

Example 14

GHF11 contig sequence was based on overlapping est-sequences FL642851.1, FL644625.1, FL644617.1, FL641536.1 of the *Reticulitermes flavipes* symbiont library termite gut metagenome cDNA. Baculovirus was prepared using homologous recombination system in Sf9 cells according to manufacturer protocols and injected into *Trichoplusia ni* larvae.

Example 15

GHF9 Cell-1 was PCR-amplified from *R. flavipes* cDNA with forward primer 5'-CTAG<u>TCTAGA</u>CTAG *ATG* AAGATACTCCTTGCTATTGCATTAATGTTGT-CAACAGTAATGTGG GTGTCAACAGCTGCTTAC-GACTATAAG-3' (SEQ ID NO.: 60) (XbaI site underlined, start codon in bold, heterologous signal sequence italicized); reverse, 5'-TTTCCTTTT<u>GCGGCCGC</u>TTAGTGATGAT-GGTGATGATGCACGCCAGCCTTGAGGAG-3' (SEQ ID NO.: 61) (NotI site underlined, stop codon in bold, 6×His italicized). The PCR amplicon encoded the ORF for the Cell-1 with the exchanged signal sequence for *Bombyx mori* (silk moth) hormone bombyxin A-6 (GENE ID: 100169714 Bbx-a6) signal sequence and the C-terminal 6×His tag, and was cloned into XbaI-NotI sites of the pVL1393 transfer vector.

Baculovirus was prepared using homologous recombination system in Sf9 cells according to manufacturer protocol and injected into *Trichoplusia ni* larvae.

Example 16

Laccase6 and 12 genes were PCR-amplified form clones (GenBank GQ421909 and GQ421911) using forward primer 5'-<u>tctaga</u>ATGTTGCCTTGCGTCCTGCTTG-3' (SEQ ID NO.: 62) (XbaI sites underlined, start codon in bold) and reverse 5'-<u>cggccg</u>TTAGTGATGATGGTGATGATG-acctcc-GTTGGTGTTCACGGGAGGTGT-3' (SEQ ID NO.: 63) (EagI sites underlined, His-6 and Gly-2 italicized and stop codon in bold). The PCR amplicons encoded full-length RfLac1 and RfLac2 plus the C-terminal His-tag, and were cloned into XbaI-EagI sites of the pVL1393 transfer vector.

Baculoviruses were prepared using homologous recombination system in Sf9 cells according to manufacturer protocol and injected into *Trichoplusia ni* larvae.

What is claimed:

1. A system for generating a fermentable product from a lignified plant material, the system consisting of a synergistically cooperating series of isolated catalytically active polypeptides, wherein said isolated catalytically active polypeptides are termite-encoded cellulase Cell-1, termite-encoded cellulase β-glucosidase GHF1, termite symbiont-encoded cellulase GHF7-3, and an aldo-keto-reductase, wherein the cellulase Cell-1 has at least 90% sequence similarity with the amino acid sequence according to SEQ ID NO: 39 or 40; the cellulase β-glucosidase GHF1 has at least 90% sequence similarity with the amino acid sequence according to SEQ ID NO: 42 or 43; the cellulase GHF7-3 has at least 90% sequence similarity with the amino acid sequence according to SEQ ID NO: 45, 48, or 50; and the aldo-keto-reductase has at least 90% sequence similarity with the amino acid sequence according to SEQ ID NO: 28 or 29.

2. The system of claim 1, wherein the catalytically active polypeptides are expressed from a recombinant expression vector or plurality of vectors.

3. The system of claim 2, wherein the recombinant expression vector or plurality of vectors are expressed from a eukaryotic cell-based recombinant expression system.

4. The system of claim 1, wherein the fermentable product is a sugar from a lignified plant material.

5. A method of converting a lignified plant material to a fermentable product, the method comprising the steps of:
    (a) obtaining a system of synergistically cooperating polypeptides according to claim 1; and
    (b) incubating the system with a source of lignified plant material under conditions allowing the polypeptides to synergistically cooperate to produce a fermentable product from the lignified plant material.

* * * * *